United States Patent [19]

Morriello et al.

[11] Patent Number: 5,721,250
[45] Date of Patent: *Feb. 24, 1998

[54] DI- AND TRI-SUBSTITUTED PIPERIDINES, PYRROLIDINES AND HEXAHYDRO-1H-AZEPINES PROMOTE RELEASE OF GROWTH HORMONE

[75] Inventors: Gregori J. Morriello, Belleville; Lihu Yang, Edison; Arthur A. Patchett, Westfield, all of N.J.

[73] Assignee: Merck & Co. Inc., Rahway, N.J.

[*] Notice: The term of this patent shall not extend beyond the expiration date of Pat. No. 5,492,916.

[21] Appl. No.: 600,646

[22] Filed: Feb. 13, 1996

Related U.S. Application Data

[63] Continuation-in-part of Ser. No. 323,988, Oct. 17, 1994, Pat. No. 5,492,916, which is a continuation-in-part of Ser. No. 173,449, Dec. 23, 1993, abandoned.

[51] Int. Cl.$^6$ .................... A61K 31/445; C07D 401/02; C07D 401/14; C07D 409/02
[52] U.S. Cl. .................... 514/318; 514/323; 546/193; 546/201
[58] Field of Search .................... 546/193, 199, 546/201, 202, 205, 209, 210; 548/127, 128, 205, 214, 253, 306.1, 467, 468; 514/318, 319, 322, 323, 324, 326, 362, 363, 365, 372, 392, 414

[56] References Cited

U.S. PATENT DOCUMENTS

| | | | |
|---|---|---|---|
| 3,239,345 | 3/1966 | Hodge et al. | 514/450 |
| 4,036,979 | 7/1977 | Asato | 514/443 |
| 4,411,890 | 10/1983 | Momany | 514/17 |
| 4,782,139 | 11/1988 | Dimarchi et al. | 530/407 |
| 5,137,872 | 8/1992 | Seely et al. | 514/12 |
| 5,164,368 | 11/1992 | Recker | 514/12 |
| 5,206,235 | 4/1993 | Fisher et al. | 514/213 |
| 5,283,241 | 2/1994 | Bochis et al. | 514/183 |
| 5,284,841 | 2/1994 | Chu et al. | 514/183 |
| 5,310,767 | 5/1994 | Fisher et al. | 514/215 |
| 5,317,017 | 5/1994 | Ok et al. | 514/211 |
| 5,492,916 | 2/1996 | Morriello et al. | 514/318 |
| 5,492,920 | 2/1996 | Chen et al. | 514/323 |
| 5,494,919 | 2/1996 | Morriello et al. | 514/323 |
| 5,606,054 | 2/1997 | Fisher et al. | 540/521 |
| 5,614,364 | 3/1997 | Tuggle et al. | 435/6 |

FOREIGN PATENT DOCUMENTS

| | | |
|---|---|---|
| 0 144 230 A3 | 6/1985 | European Pat. Off. . |
| WO 94/07486 | 4/1994 | WIPO . |
| WO 94/08583 | 4/1994 | WIPO . |
| WO 94/13696 | 6/1994 | WIPO . |
| WO 94/19367 | 9/1994 | WIPO . |
| WO 95/13069 | 5/1995 | WIPO . |

OTHER PUBLICATIONS

Sakamoto, et al., Chem. Abstracts, 113 (9) 73,560u (1990).
Horwell, et al., Chem. Abstracts, 113(15) 132,771p (1990).
Ammann, et al., Am. J. Physiology, vol. 265, pp. E770–776 (1993) "IGF-I and pamidronate increase bone mineral density in ovariectomized adult rats".
R.G. Smith, et al., Science, Reprint Series, 11 Jun. 1993, vol. 260, pp. 1640–1643 "A Nonpeptidyl Growth Hormone Secretagogue".

Primary Examiner—Ceila Chang
Attorney, Agent, or Firm—J. Eric Thies; David L. Rose

[57] ABSTRACT

The present invention is directed to certain novel compounds identified as di- and tri-substituted piperidines, pyrrolidines, and hexahydro-1H-azepines of the general structural formula:

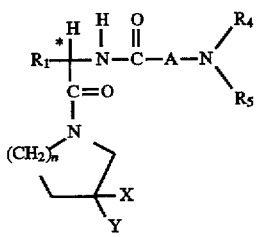

wherein $R_1$, $R_4$, $R_5$, A, X, Y, and n are as defined herein. These compounds promote the release of growth hormone in humans and animals. This property can be utilized to promote the growth of food animals to render the production of edible meat products more efficient, and in humans, to treat physiological or medical conditions characterized by a deficiency in growth hormone secretion, such as short stature in growth hormone deficient children, and to treat medical conditions which are improved by growth hormone. Growth hormone releasing compositions containing such di and tri substituted piperidines, pyrrolidines, and hexahydro-1H-azepines as the active ingredient thereof are also disclosed.

3 Claims, No Drawings

DI-AND TRI-SUBSTITUTED PIPERIDINES, PYRROLIDINES AND HEXAHYDRO-1H-AZEPINES PROMOTE RELEASE OF GROWTH HORMONE

CROSS REFERENCE TO RELATED APPLICATIONS

This application is a continuation-in-part of application Ser. No. 08/323,988, filed Oct. 17, 1994, issuing as U.S. Pat. No. 5,492,916 on Feb. 20, 1996, which is a continuation-in-part of application Ser. No. 08/173,449, filed Dec. 23, 1993, now abandoned.

BACKGROUND OF THE INVENTION

Growth hormone, which is secreted from the pituitary, stimulates growth of all tissues of the body that are capable of growing. In addition, growth hormone is known to have the following basic effects on the metabolic processes of the body: (1) Increased rate of protein synthesis in all cells of the body; (2) Decreased rate of carbohydrate utilization in cells of the body; (3) Increased mobilization of free fatty acids and use of fatty acids for energy. A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering GRF or a peptidal compound which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recombinant growth hormone has become available which, while no longer carrying any risk of disease transmission, is still a very expensive product which must be given by injection or by a nasal spray. Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. Non peptidal growth hormone secretagogues with a benzolactam structure are disclosed in e.g., U.S. Pat. Nos. 5,206,235, 5,283,241, 5,284,841, 5,310,737 and 5,317,017. Other growth hormone secretagogues are disclosed e.g., in PCT Patent Publications WO 94/13696, WO 94/19367, and WO 95/09633. The instant compounds are low molecular weight peptide analogs for promoting the release of growth hormone which have good stability in a variety of physiological environments and which may be administered parenterally, nasally or by the oral route.

SUMMARY OF THE INVENTION

The instant invention is directed to certain di- and tri-substituted piperidine, pyrrolidine and hexahydro-1H-azepine compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food or wool production where the stimulation of growth hormone will result in a larger, more productive animal. Thus, it is an object of the instant invention to describe the di- and tri-substituted piperidine, pyrrolidine and hexahydro-1H-azepine compounds. It is a further object of this invention to describe procedures for the preparation of such compounds. A still further object is to describe the use of such compounds to increase the secretion of growth hormone in humans and animals. A still further object of this invention is to describe compositions containing the di- and tri-substituted piperidine, pyrrolidine and hexahydro-1H-azepine compounds for the use of treating humans and animals so as to increase the level of growth hormone secretions. Further objects will become apparent from a reading of the following description.

DESCRIPTION OF THE INVENTION

The novel di- and tri- substituted piperidines, pyrrolidines and hexahydro-1H-azepines of the instant invention are described by structural Formula I:

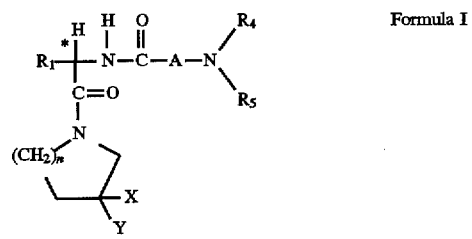

Formula I wherein:

$R_1$ is selected from the group consisting of: $C_1$–$C_{10}$ alkyl, aryl, aryl($C_1$–$C_6$ alkyl), ($C_3$–$C_7$ cycloalkyl)($C_1$–$C_6$ alkyl)-, ($C_1$–$C_5$ alkyl)-K—($C_1$–$C_5$ alkyl)-, aryl($C_0$–$C_5$ alkyl)-K—($C_1$–$C_5$ alkyl)-, and ($C_3$–$C_7$ cycloalkyl) ($C_0$–$C_5$ alkyl)-K—($C_1$–$C_5$ alkyl)-, where K is O, S(O)$_m$, N($R_2$)C(O), C(O)N($R_2$), OC(O), C(O)O, —CR$_2$=CR$_2$—, or —C≡C—, where aryl is selected from: phenyl, naphthyl, indolyl, azaindole, pyridyl, benzothienyl, benzofuranyl, thiazolyl, and benzimidazolyl, and $R_2$ and alkyl may be further substituted by 1 to 9 halogen, S(O)$_m$R$_{2a}$, 1 to 3 of OR$_{2a}$ or C(O)OR$_{2a}$, and aryl may be further substituted by 1 to 3 of $C_1$–$C_6$ alkyl, 1 to 3 of halogen, 1 to 2 of OR$_2$, methylenedioxy, —S(O)$_m$R$_2$, 1 to 2 of —CF$_3$, —OCF$_3$, nitro, —N(R$_2$)C(O)(R$_2$), —C(O)OR$_2$, —C(O)N(R$_2$) (R$_2$), -1H-tetrazol-5-yl, —SO$_2$N(R$_2$)(R$_2$), —N(R$_2$)SO$_2$ phenyl, or —N(R$_2$)SO$_2$R$_2$;

$R_2$ is selected from: hydrogen, $C_1$–$C_6$ alkyl, and $C_3$–$C_7$ cycloalkyl, and where two $C_1$–$C_6$ alkyl groups are present on one atom, they may be optionally joined to form a $C_3$–$C_8$ cyclic ring, optionally including oxygen, sulfur or NR$_{3a}$, where R$_{3a}$ is hydrogen, or $C_1$–$C_6$ alkyl, optionally substituted by hydroxyl;

X is selected from: hydrogen, —C≡N, —(CH$_2$)$_q$N(R$_2$) C(O)R$_2$, —(CH$_2$)qN(R$_2$)C(O)(CH$_2$)$_t$aryl, —(CH$_2$)$_q$N (R$_2$)SO$_2$(CH$_2$)$_t$aryl, —(CH$_2$)$_q$N(R$_2$)SO$_2$R$_2$, —(CH$_2$)$_q$N(R$_2$)C(O)N(R$_2$)(CH$_2$)$_t$aryl, —(CH$_2$)$_q$N(R$_2$)C(O)N(R$_2$)(R$_2$), —(CH$_2$)$_q$C(O)N(R$_2$)(R$_2$), —(CH$_2$)$_q$C(O)N(R$_2$)(CH$_2$)$_t$aryl, —(CH$_2$)$_q$C(O)OR$_2$, —(CH$_2$)$_q$C(O)O(CH$_2$)$_t$aryl, —(CH$_2$)$_q$OR$_2$, —(CH$_2$)$_q$OC(O)R$_2$, —(CH$_2$)$_q$OC(O)(CH$_2$)$_t$aryl, —(CH$_2$)$_q$OC(O)N(R$_2$)(CH$_2$)$_t$aryl, —(CH$_2$)$_q$OC(O)N(R$_2$)(R$_2$), —(CH$_2$)$_q$C(O)R$_2$, —(CH$_2$)$_q$C(O) (CH$_2$)$_t$aryl, —(CH$_2$)$_q$N(R$_2$)C(O)OR$_2$, —(CH$_2$)$_q$N(R$_2$)SO$_2$N(R$_2$)(R$_2$), —(CH$_2$)$_q$S(O)$_m$R$_2$, and —(CH$_2$)$_q$S(O)$_m$(CH$_2$)$_t$aryl, where an R$_2$, (CH$_2$)$_q$ and (CH$_2$)$_t$ group may be optionally substituted by 1 to 2 C$_1$–C$_4$ alkyl, hydroxyl, C$_1$–C$_4$ lower alkoxy, carboxyl, CONH$_2$, S(O)$_m$CH$_3$, carboxylate C$_1$–C$_4$ alkyl esters, or 1H-tetrazol-5-yl, and aryl is phenyl, naphthyl, pyridyl, thiazolyl, or 1H-tetrazol-5-yl groups which may be optionally substituted by 1 to 3 halogen, 1 to 3 —OR$_2$, —CON(R$_2$)(R$_2$), —C(O)OR$_2$, 1 to 3 C$_1$–C$_4$ alkyl, —S(O)$_m$R$_2$, or 1H-tetrazol-5-yl;

Y is selected from: hydrogen, C$_1$–C$_{10}$ alkyl, —(CH$_2$)$_t$aryl, —(CH$_2$)$_q$(C$_3$–C$_7$ cycloalkyl), —(CH$_2$)$_q$—K—(C$_1$–C$_6$ alkyl), —(CH$_2$)$_q$—K—(CH$_2$)$_t$aryl, —(CH$_2$)$_q$—K—(CH$_2$)$_t$(C$_3$–C$_7$ cycloalkyl containing O, NR2, S), and —(CH$_2$)$_q$—K—(CH$_2$)$_t$(C$_3$–C$_7$ cycloalkyl), where K is O, S(O)$_m$, C(O)NR$_2$, CH=CH, C≡C, N(R$_2$)C(O), C(O)NR$_2$, C(O)O, or OC(O), and where the alkyl, R$_2$, (CH$_2$)$_q$ and (CH$_2$)$_t$ groups may be optionally substituted by C$_1$–C$_4$ alkyl, hydroxyl, C$_1$–C$_4$ lower alkoxy, carboxyl, —CONH$_2$ or carboxylate C$_1$–C$_4$ alkyl esters, and aryl is phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, thiopheneyl, quinolinyl, pyrazinyl, or isothiazolyl which is optionally substituted by 1 to 3 halogen, 1 to 3 —OR$_2$, —C(O)OR$_2$, —C(O)N(R$_2$)(R$_2$), nitro, cyano, benzyl, 1 to 3 C$_1$–C$_4$ alkyl, —S(O)$_m$R$_2$, or 1H-tetrazol-5-yl, with the proviso that if X is hydrogen, Y is other than hydrogen;

R$_4$ and R 5 are independently hydrogen, C$_1$–C$_6$ alkyl, or substituted C$_1$–C$_6$ alkyl where the substituents may be 1 to 5 halo, 1 to 3 hydroxy, 1 to 3 C$_1$–C$_{10}$ alkanoyloxy, 1 to 3 C$_1$–C$_6$ alkoxy, phenyl, phenyloxy, 2-furyl, C$_1$–C$_6$ alkoxycarbonyl, S(O)$_m$(C$_1$–C$_6$ alkyl), or R$_4$ and R$_5$ may be taken together to form —(CH$_2$)$_d$—L$_a$(CH$_2$)$_e$— where L$_a$ is —C(R$_2$)$_2$—, O, S(O)$_m$ or N(R$_2$), d and e are independently 1 to 3 and R$_2$ is as defined above;

A is:

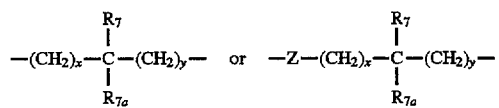

where x and y are independently 0, 1, 2 or 3;

Z is N—R$_{6a}$ or O, where R$_{6a}$ is hydrogen or C$_1$–C$_6$ alkyl;

R$_7$ and R$_{7a}$ are independently hydrogen, C$_1$–C$_6$ alkyl, trifluoromethyl, phenyl, or substituted C$_1$–C$_6$ alkyl where the substituents are imidazolyl, phenyl, indolyl, p-hydroxyphenyl, OR$_2$, S(O)$_m$R$_2$, C(O)OR$_2$, C$_3$–C$_7$ cycloalkyl, N(R$_2$)(R$_2$), C(O)N(R$_2$)(R$_2$), or R$_7$ and R$_{7a}$ may independently be joined to one or both of R$_4$ and R$_5$ groups to form an alkylene bridge between the terminal nitrogen and the alkyl portion of the R$_7$ or R$_{7a}$ groups, wherein the bridge contains 1 to 5 carbons atoms, or R$_7$ and R$_{7a}$ can be joined to one another to form C$_3$–C$_7$ cycloalkyl;

m is 0, 1, or 2;

n is 1, 2, or 3;

q is 0, 1, 2, 3, or 4;

t is 0, 1, 2, or 3;

and pharmaceutically acceptable salts and individual diastereomers thereof.

In the above structural formula and throughout the instant specification, the following terms have the indicated meanings:

When n is 1 a pyrrolidine ring is formed, when n is 2 a piperidine ring is formed, and when n is 3 the ring is designated a hexahydro-1-H-azepine.

The alkyl groups specified above are intended to include those alkyl groups of the designated length in either a straight or branched configuration and if two carbon atoms or more they may include a double or a triple bond. Exemplary of such alkyl groups are methyl, ethyl, propyl, isopropyl, butyl, sec-butyl, tertiary butyl, pentyl, isopentyl, hexyl, isohexyl, allyl, propargyl, and the like.

The alkoxy groups specified above are intended to include those alkoxy groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

The term "halogen" is intended to include the halogen atom fluorine, chlorine, bromine and iodine.

The term "aryl" within the present invention, unless otherwise specified, is intended to include aromatic rings, such as carbocyclic and heterocyclic aromatic rings selected the group consisting of: phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, thiopheneyl, quinolinyl, pyrrazinyl, or isothiazolyl, which may be optionally substituted by 1 to 3 of C$_1$–C$_6$ alkyl, 1 to 3 of halogen, 1 to 2 of OR$_2$, methylenedioxy, —S(O)$_m$R$_2$, 1 to 2 of —CF$_3$, —OCF$_3$, nitro, —N(R$_2$)C(O)(R$_2$), —C(O)OR$_2$, —C(O)N(R$_2$)(R$_2$), -1H-tetrazol-5-yl, —SO$_2$N(R$_2$)(R$_2$), —N(R$_2$)SO$_2$phenyl, or —N(R$_2$)SO$_2$R$_2$, wherein R$_2$ is as defined herein.

Certain of the above defined terms may occur more than once in the above formula and upon such occurrence each term shall be defined independently of the other.

Preferred compounds of the instant invention include those of Formula Ia:

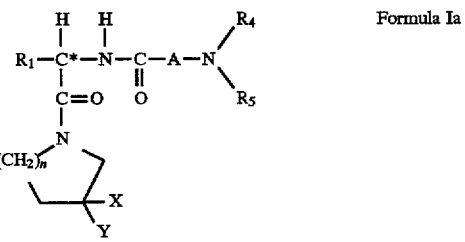

Formula Ia wherein:

R$_1$ is selected from the group consisting of: C$_1$–C$_{10}$ alkyl, aryl (C$_1$–C$_4$ alkyl)-, C$_3$–C$_6$ cycloalkyl (C$_1$–C$_4$ alkyl)-, (C$_1$–C$_4$ alkyl)-K—(C$_1$–C$_2$ alkyl)-, aryl (C$_0$–C$_2$ alkyl)-K—(C$_1$–C$_2$ alkyl)-, and (C$_3$–C$_7$ cycloalkyl)(C$_0$–C$_2$ alkyl)-K—(C$_1$–C$_2$ alkyl)-, where K is O, S(O)$_m$, OC(O), or C(O)O, and the alkyl groups may be further substituted by 1 to 7 halogen, S(O)$_m$R$_2$, 1 to 3 OR$_2$ or C(O)OR$_2$, and aryl is phenyl, naphthyl, indolyl, pyridyl, benzimidazolyl, azaindoleyl, benzothienyl or benzofuranyl which may be further substituted by 1–2 C$_1$–C$_4$ alkyl, 1 to 2 halogen, 1 to 2 —OR$_2$, —S(O)$_m$R$_2$, or —C(O)OR$_2$;

$R_2$ is hydrogen, $C_1$–$C_6$ alkyl, or $C_3$–$C_7$ cycloalkyl, and where two $C_1$–$C_6$ alkyl groups are present on one atom they may be optionally joined to form a $C_4$–$C_7$ cyclic ring optionally including oxygen, sulfur or $NR_{3a}$;

$R_{3a}$ is hydrogen, or $C_1$–$C_4$ alkyl;

X is selected from: hydrogen, —(CH$_2$)qN(R$_2$)C(O)R$_2$, —(CH$_2$)qN(CR$_2$)C(O)(CH$_2$)$_t$aryl, —(CH$_2$)qN(R$_2$)C(O)OR$_2$, —(CH$_2$)qN(R$_2$)SO$_2$(CH$_2$)$_t$aryl, —(CH$_2$)qN(R$_2$)SO$_2$R$_2$, —(CH$_2$)qN(R$_2$)C(O)N(R$_2$)(CH$_2$)$_t$aryl, —(CH$_2$)qN(R$_2$)C(O)N(R$_2$)OR$_2$), —(CH$_2$)qC(O)N(R$_2$)(R$_2$), —(CH$_2$)$_q$C(O)N(R$_2$)(CH$_2$)$_t$aryl, —(CH$_2$)qC(O)OR$_2$, —(CH$_2$)qC(O)O(CH$_2$)$_t$aryl, —(CH$_2$)qOC(O)R$_2$, —(CH$_2$)qOC(O)(CH$_2$)$_t$aryl, —(CH$_2$)qS(O)$_m$R$_2$, and —(CH$_2$)$_q$S(O)$_m$(CH$_2$)$_t$aryl, where an R$_2$ group may be optionally substituted by hydroxyl, carboxyl, CONH$_2$, S(O)$_m$CH$_3$, carboxylate $C_1$–$C_4$ alkyl esters, or tetrazole, and aryl is phenyl, naphthyl, pyridyl or 1-H-tetrazolyl which may be optionally substituted by 1 to 2 halogen, 1 to 2 —OR$_2$, —CONH$_2$, —C(O)OR$_2$, 1 to 3 $C_1$–$C_4$ alkyl, —S(O)$_m$R$_2$, or 1H-tetrazole-5-yl;

Y is selected from: hydrogen, $C_1$–$C_8$ alkyl, (CH$_2$)$_t$aryl, —(CH$_2$)$_q$(C$_5$–C$_6$ cycloalkyl), —(CH$_2$)$_q$—K—(C$_1$–C$_6$ alkyl), —(CH$_2$)$_q$—K—(CH$_2$)$_t$aryl, —(CH$_2$)$_q$—K—(CH$_2$)$_t$(C$_3$–C$_7$ cycloalkyl containing O, NR$_2$, or S), and —(CH$_2$)q—K—(CH$_2$)$_t$(C$_5$–C$_6$ cycloalkyl), where K is O or S(O)$_m$ and where the alkyl groups may be optionally substituted by hydroxyl, carboxyl, CONH$_2$, carboxylate $C_1$–$C_4$ alkyl esters or 1H-tetrazole-5-yl and aryl is phenyl, naphthyl, pyridyl, 1-H-tetrazolyl, thiazolyl, imidazolyl, indolyl, pyrimidinyl, thiadiazolyl, pyrazolyl, oxazolyl, isoxazolyl, or thiopheneyl which is optionally substituted by 1 to 3 halogen, 1 to 3 —OR$_2$, —C(O)OR$_2$, —C(O)N(R$_2$)(R$_2$), cyano, 1 to 2 $C_1$–$C_4$ alkyl, benzyl, —S(O)$_m$R$_2$, or 1H-tetrazol-5-yl, with the proviso that if X is hydrogen, Y is other than hydrogen;

$R_4$ and $R_5$ are independently hydrogen, $C_1$–$C_6$ alkyl, or substituted $C_1$–$C_6$ alkyl where the substituents may be 1 to 5 halo, 1 to 3 hydroxyl, S(O)$_m$(C$_1$–C$_6$ alkyl) or phenyl;

A is:

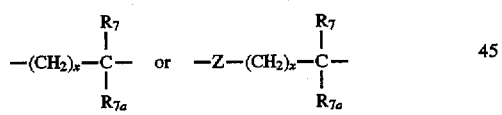

where x is 0 or 1;

Z is N-R$_6$a or O, where R$_6$a is hydrogen or $C_1$–$C_6$ alkyl;

$R_7$ and $R_{7a}$ are independently hydrogen $C_1$–$C_6$ alkyl, trifluoromethyl, phenyl, substituted $C_1$–$C_6$ alkyl where the substituents are imidazolyl, phenyl, indolyl, p-hydroxyphenyl, OR$_2$, S(O)mR$_2$, C(O)OR$_2$, $C_5$–$C_7$ cycloalkyl, —N(R$_2$)(R$_2$), —C(O)N(R$_2$)(R$_2$); or R$_7$ and R$_{7a}$ can independently be joined to one of R$_4$ or R$_5$ to form alkylene bridges between the terminal nitrogen and the alkyl portion of R$_7$ or R$_{7a}$ groups to form 5 or 6 membered rings; or R$_7$ and R$_{7a}$ can be joined to one another to form a $C_3$ cycloalkyl;

n is 2;

m is 0, 1, or 2;

q is 0, 1, 2, or 3;

t is 0, 1, 2, or 3;

and pharmaceutically acceptable salts and individual diastereomers thereof.

More preferred compounds of the instant invention include those of Formula Ib:

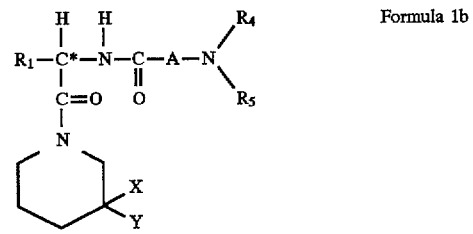

Formula Ib wherein:

$R_1$ is selected from the group consisting of: $C_1$–$C_{10}$ alkyl, aryl ($C_1$–$C_3$ alkyl)-, ($C_3$–$C_7$ cycloalkyl)($C_1$–$C_3$ alkyl)-, and aryl ($C_0$–$C_1$ alkyl)-K—($C_1$–$C_2$ alkyl)-, where K is O or S(O)$_m$ and the aryl is phenyl, pyridyl, naphthyl, indolyl, azaindolyl, or benzimidazolyl which is optionally substituted by 1–2 $C_1$–$C_4$ alkyl, 1 to 2 halogen, 1 to 2 OR$_2$, S(O)$_m$R$_2$, or C(O)OR$_2$;

$R_2$ is hydrogen, $C_1$–$C_6$ alkyl, or $C_3$–$C_7$ cycloalkyl, and where two $C_1$–$C_6$ alkyl groups are present on one atom they may be optionally joined to form a $C_5$–$C_7$ cyclic ring optionally including oxygen, sulfur or $NR_{3a}$;

$R_{3a}$ is hydrogen, or $C_1$–$C_4$ alkyl;

X is selected from: hydrogen, —(CH$_2$)qN(R$_2$)C(O)R$_2$, —(CH$_2$)qN(R$_2$)C(O)(CH$_2$)$_t$aryl, —(CH$_2$)qN(R$_2$)SO$_2$(CH$_2$)$_t$aryl, —(CH$_2$)qN(R$_2$)SO$_2$R$_2$, —(CH$_2$)$_q$N(R$_2$)C(O)N(R$_2$)(CH$_2$)$_t$aryl, —(CH$_2$)$_q$N(R$_2$)C(O)N(R$_2$)(R$_2$), —(CH$_2$)qC(O)N(R$_2$)(R$_2$), —(CH$_2$)qN(R$_2$)C(O)OR$_2$, —(CH$_2$)qC(O)N(R$_2$)(CH$_2$)$_t$aryl, —(CH$_2$)qC(O)OR$_2$, —(CH$_2$)$_q$C(O)O(CH$_2$)$_t$aryl, —(CH$_2$)qOC(O)R$_2$, —(CH$_2$)qOC(O)(CH$_2$)$_t$aryl, —(CH$_2$)qS(O)$_m$R$_2$, and —(CH$_2$)qS(O)$_m$(CH$_2$)$_t$aryl, where an R$_2$ group may be optionally substituted by hydroxyl, carboxyl, —CONH$_2$, —S(O)$_m$CH$_3$, carboxylate $C_1$–$C_4$ alkyl esters or tetrazole and aryl is phenyl, naphthyl or pyridyl which may be further substituted by 1–2 halogen, 1 to 2 OR$_2$, C(O)OR$_2$, 1 to 3 $C_1$–$C_4$ alkyl, S(O)$_m$R$_2$, or 1H-tetrazole-5-yl;

Y is selected from: hydrogen, $C_1$–$C_8$ alkyl, (CH$_2$)$_t$aryl, -(CH$_2$)$_q$C$_5$–$C_7$ cycloalkyl, —(CH$_2$)$_q$—K—(C$_1$–C$_6$ alkyl), —(CH$_2$)$_q$—K—(CH$_2$)$_t$aryl, and —(CH$_2$)$_q$—K—(CH$_2$)$_t$(C$_5$–C$_6$ cycloalkyl), where K is S(O)$_m$ and where the alkyl groups may be optionally substituted by hydroxyl, carboxyl, CONH$_2$, carboxylate $C_1$–$C_4$ alkyl esters or 1H-tetrazole-5-yl and aryl is phenyl, napthyl, pyridyl, thiazolyl, thiopheneyl, pyrazolyl, oxazolyl, isoxazolyl or imidazolyl which may be optionally substituted by 1 to 2 halogen, 1 to 2 OR$_2$, 1 to 2 —N(R$_2$)(R$_2$), CO(OR$_2$), 1 to 2 $C_1$–$C_4$ alkyl, S(O)$_m$R$_2$, or 1H-tetrazol-5-yl, with the proviso that if X is hydrogen, Y is other than hydrogen;

$R_4$ and $R_5$ are independently hydrogen, $C_1$–$C_4$ alkyl, or substituted $C_1$–$C_3$ alkyl where the substituents may be 1 to 2 hydroxyl;

A is

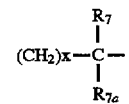

where x is 0, or 1;

$R_7$ and $R_{7a}$ are independently hydrogen, $C_1$–$C_6$ alkyl, phenyl, substituted $C_1$–$C_6$ alky wherein the substituent is imidixolyl, phenyl, indolyl, p-hydroxyphenyl, $OR_2$, $S(O)_mR_2$, or $R_7$ and $R_{7a}$ may be joined to one another to form a $C_3$ cycloalkyl;

m is 0, 1, or 2;

q is 0, 1, 2, or 3;

t is 0, 1, 2, or 3;

and pharmaceutically acceptable salts and individual diastereomers thereof.

Still more preferred compounds of the instant invention include those of Formula Ic:

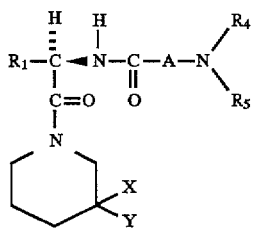

Formula Ic wherein:

$R_1$ is selected from the group consisting of:

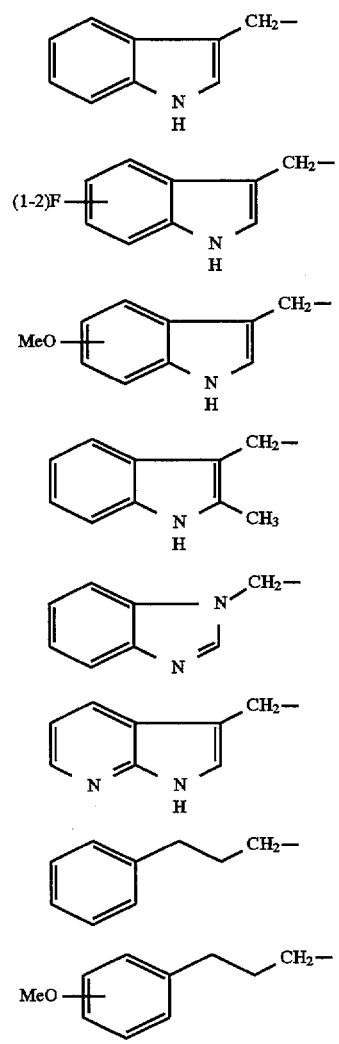

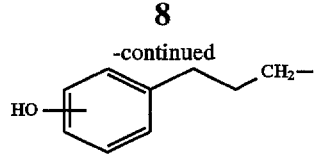

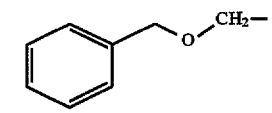

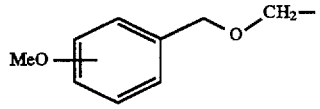

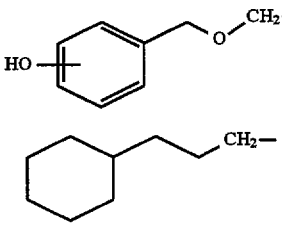

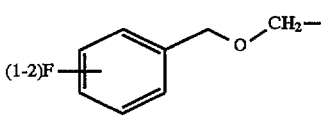

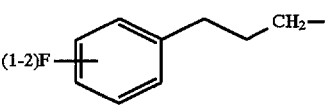

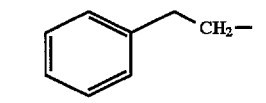

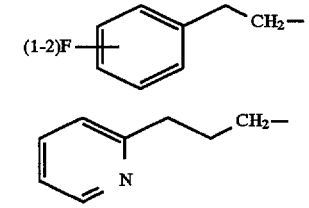

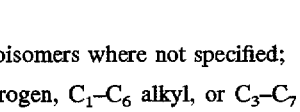

or their regioisomers where not specified;

$R_2$ is hydrogen, $C_1$–$C_6$ alkyl, or $C_3$–$C_7$ cycloalkyl and where two $C_1$–$C_6$ alkyl groups are present on one atom they may be optionally joined to form a $C_5$–$C_7$ cyclic ring optionally including oxygen, sulfur or $NR_{3a}$;

$R_{3a}$ is hydrogen, or $C_1$–$C_4$ alkyl;

X is selected from the group consisting of: hydrogen,

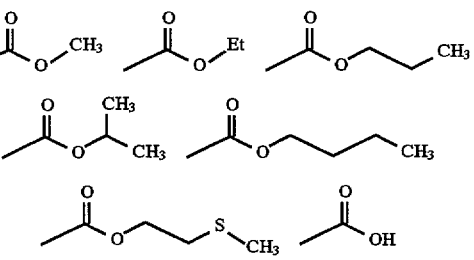

-continued
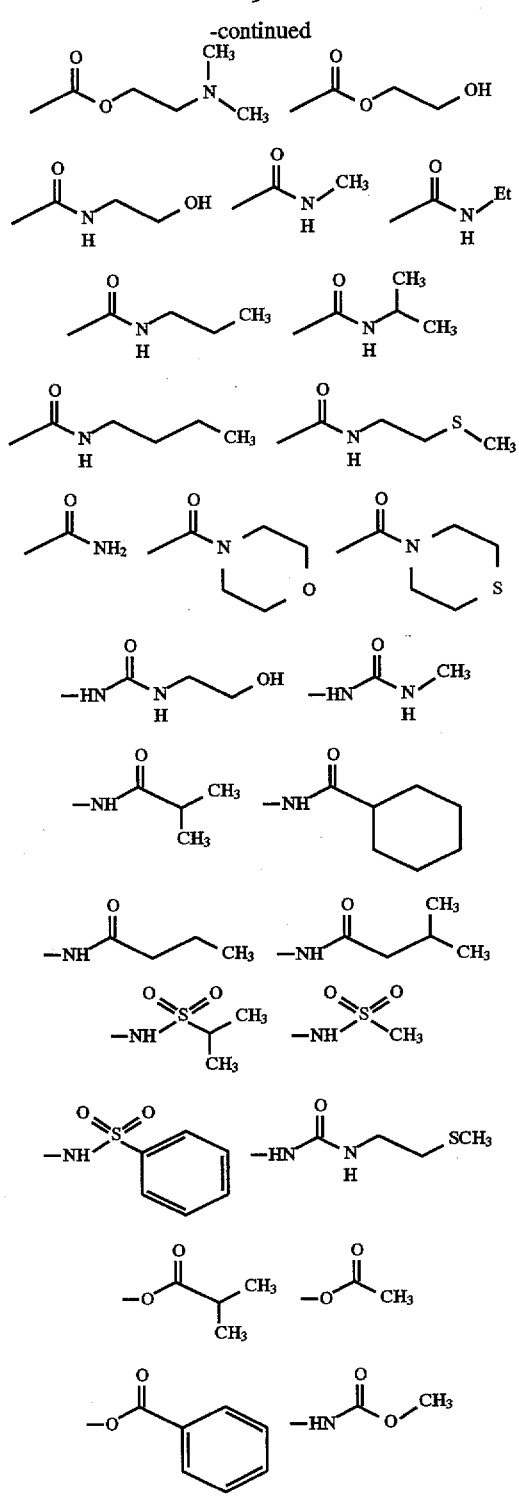
Y is selected from the group consisting of: hydrogen,
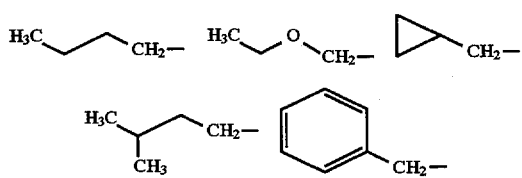
-continued
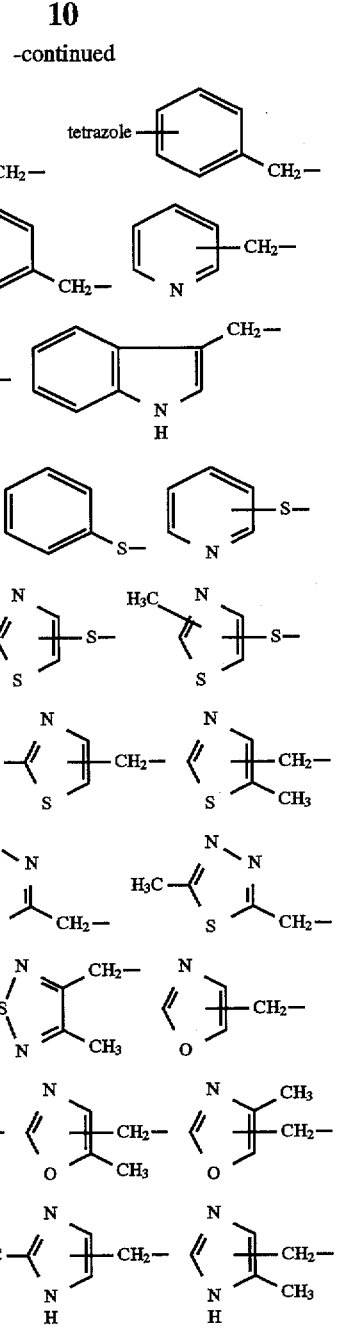
or their regioisomers whereof where not specified, with the proviso that if
X is hydrogen, Y is other than hydrogen;
A is selected from the group consisting of:
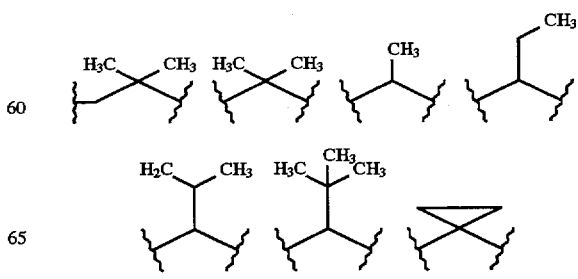

-continued
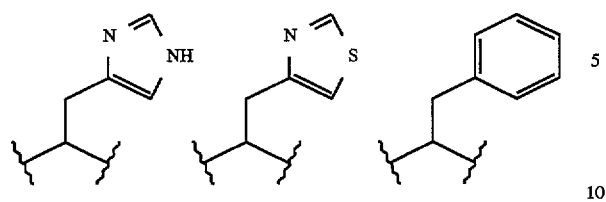
R₄ and R₅ are independently selected from the group consisting of:
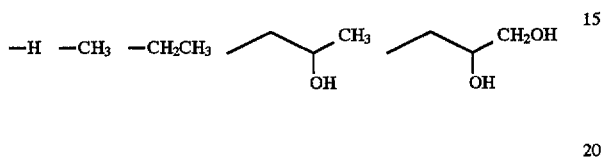
and pharmaceutically acceptable salts and individual diastereomers thereof.
Specific compounds of the instant invention include the following:
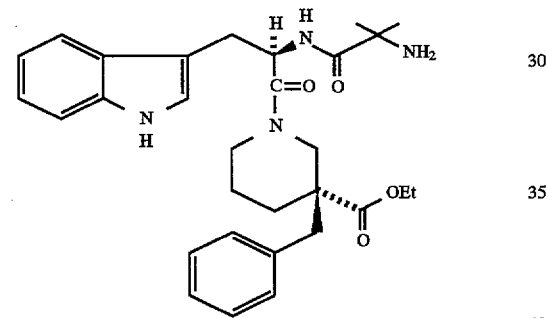
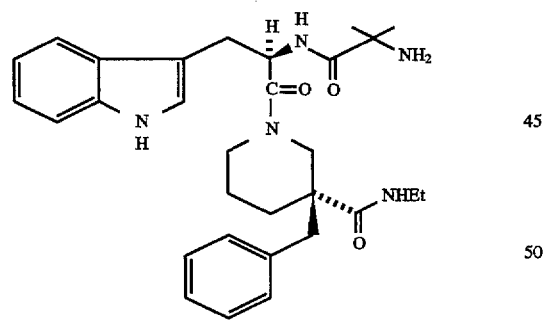
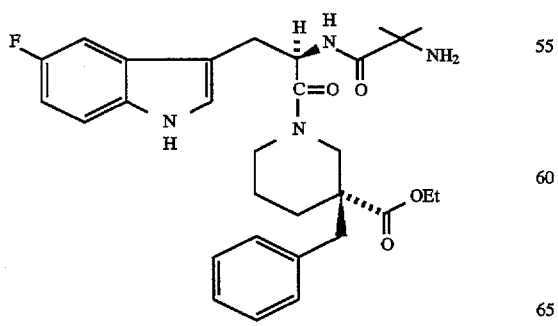
-continued
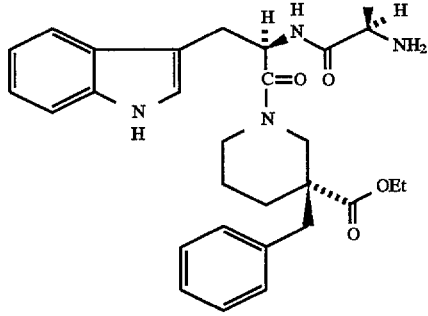
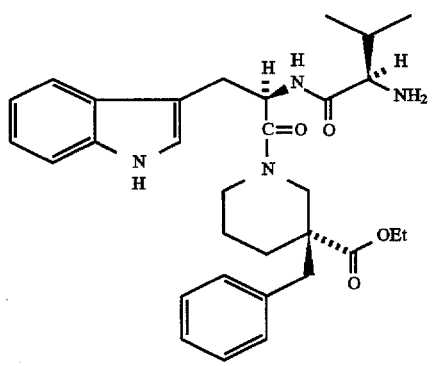
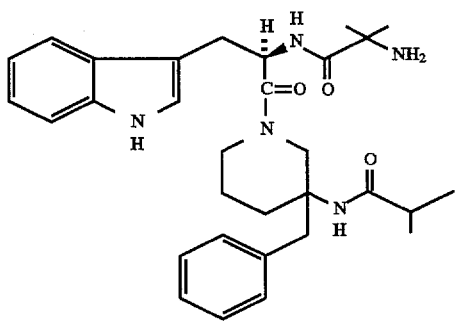
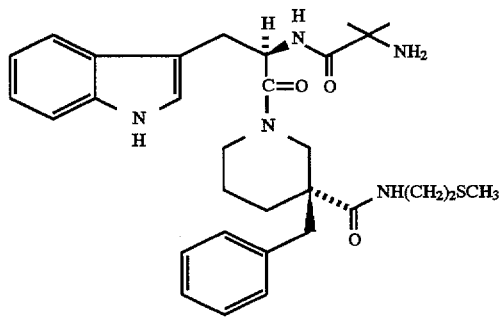
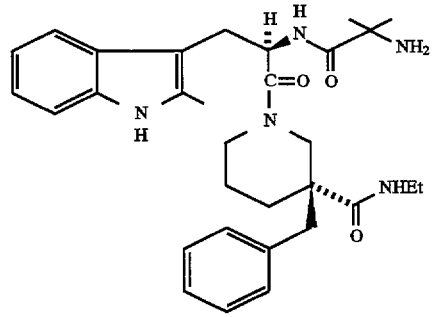

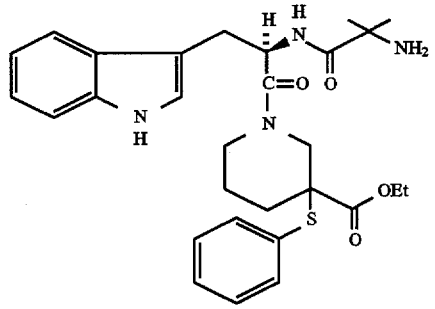
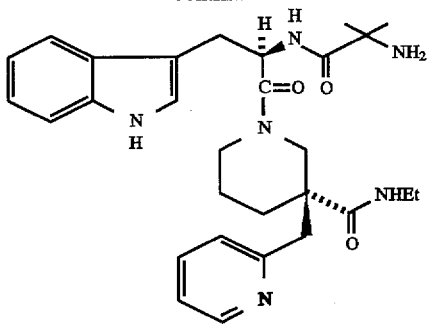
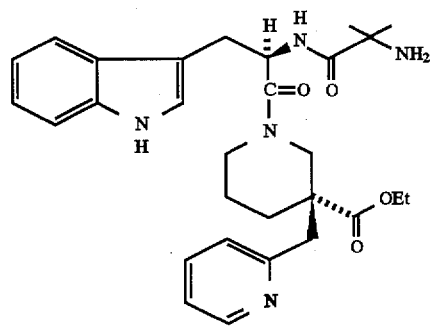
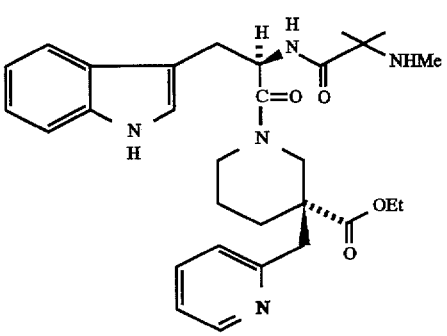
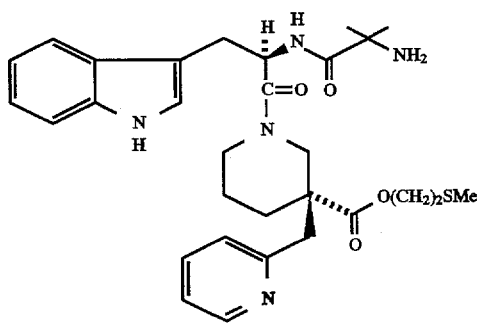
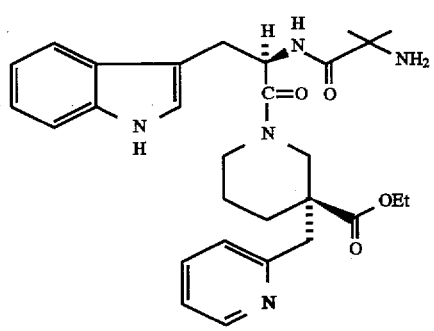
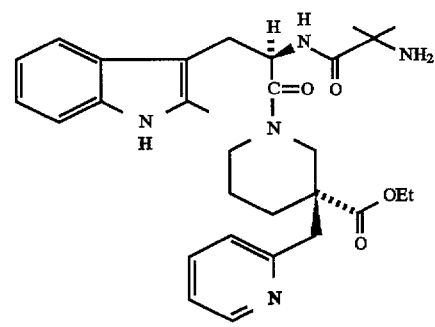
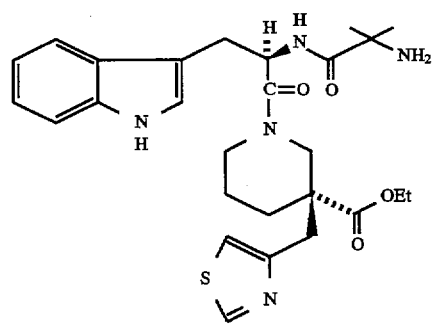
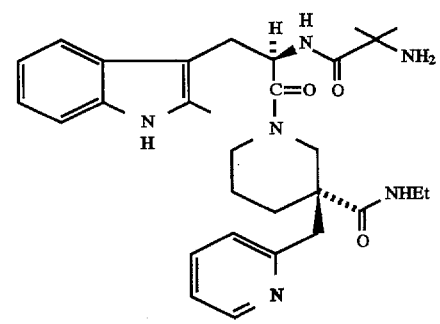
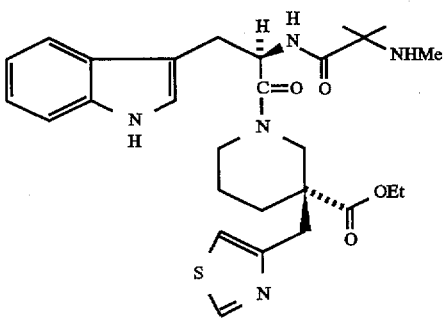

-continued
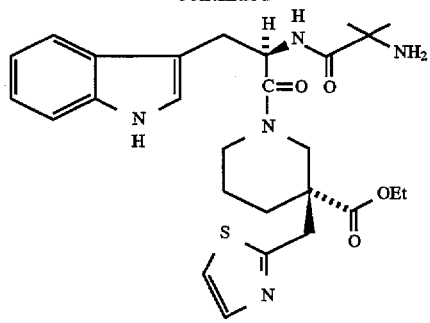
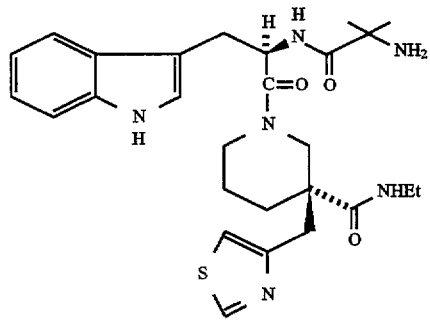
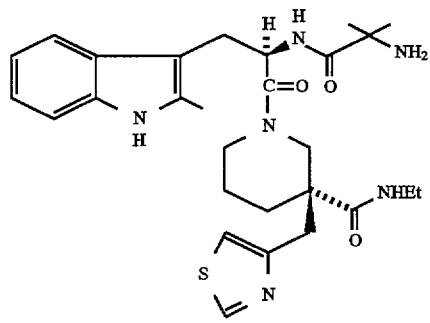
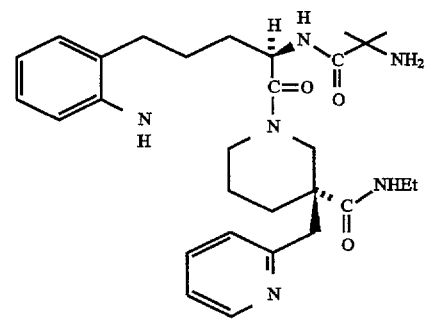
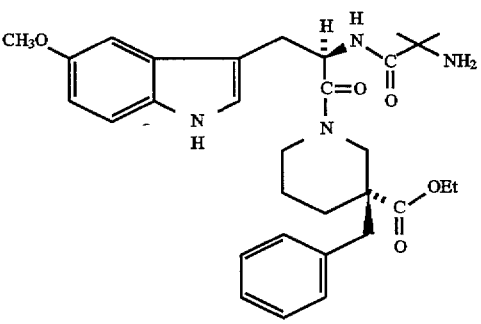
-continued
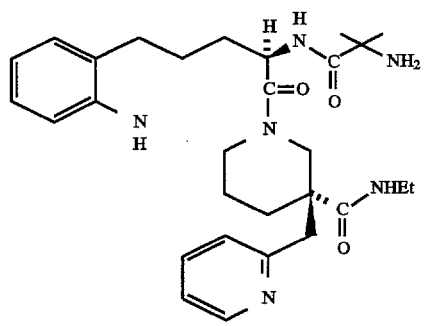
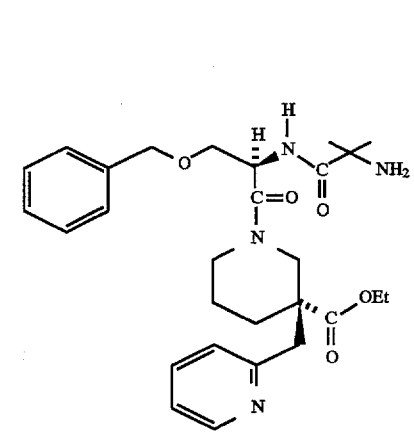
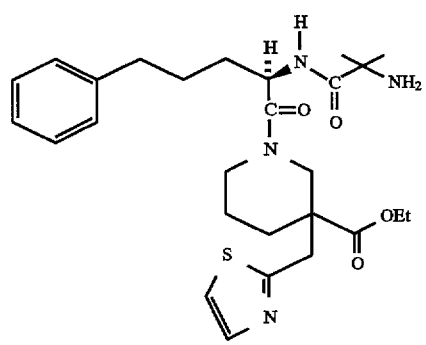
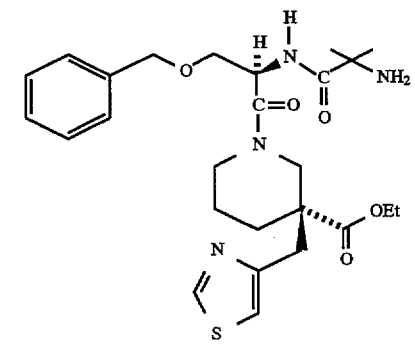

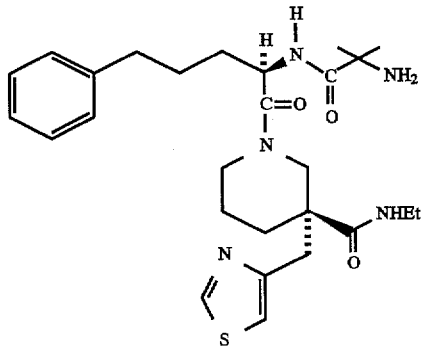
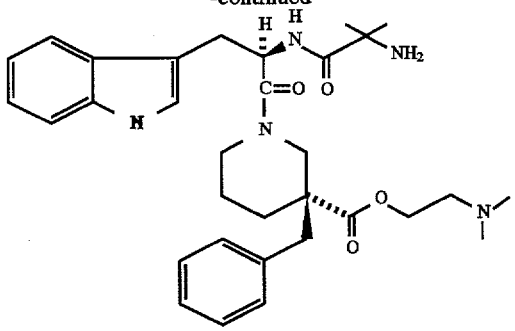
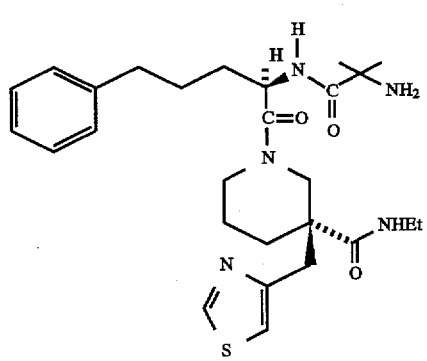
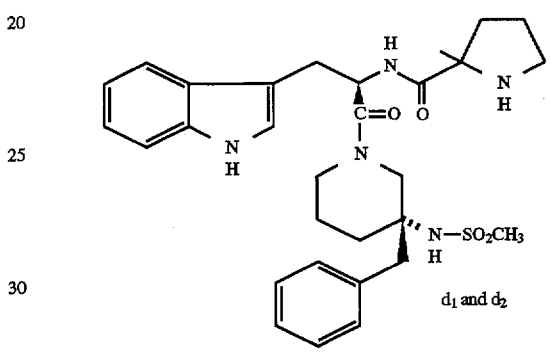
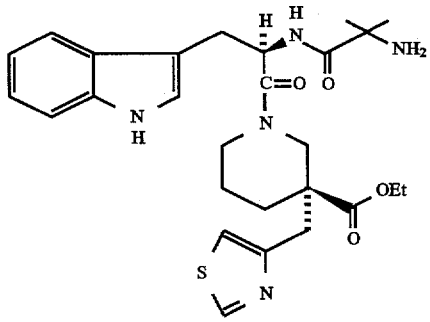
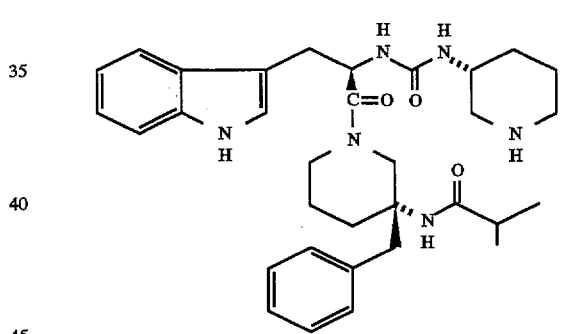
and their pharmaceutically acceptable salts and individual diasteromers thereof where not otherwise specified.
Additional specific compounds of the instant invention include the following:
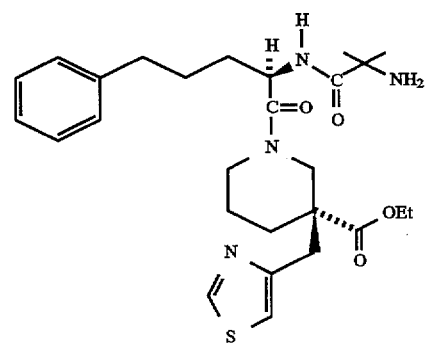
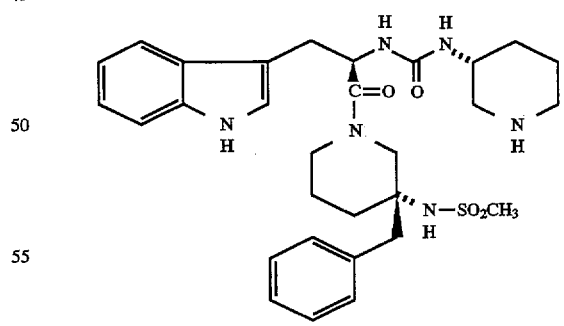

-continued
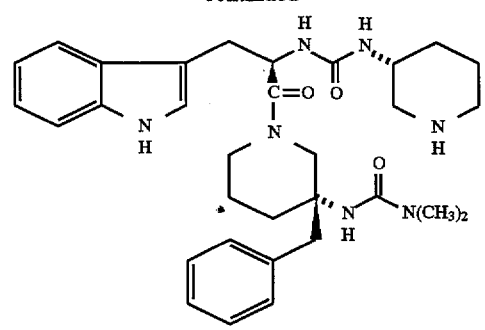
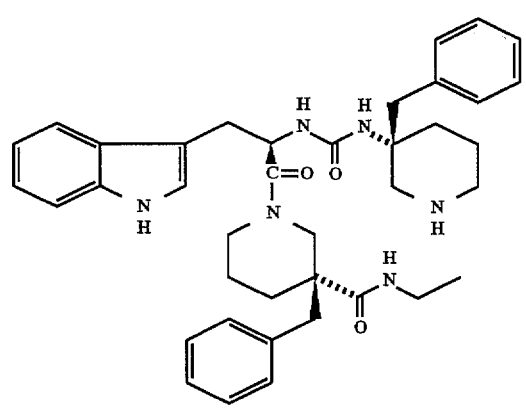
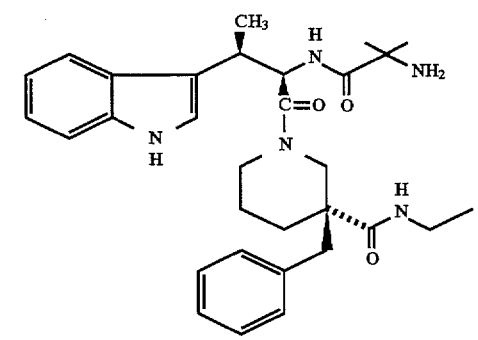
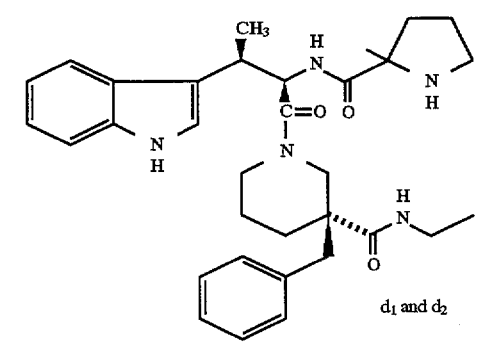
d₁ and d₂
-continued
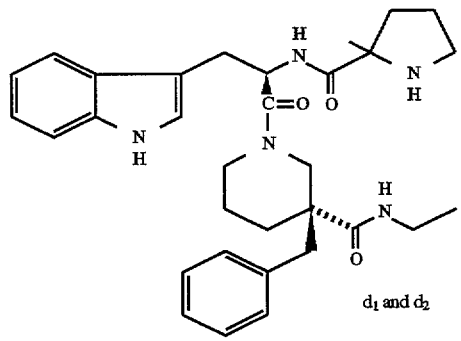
d₁ and d₂
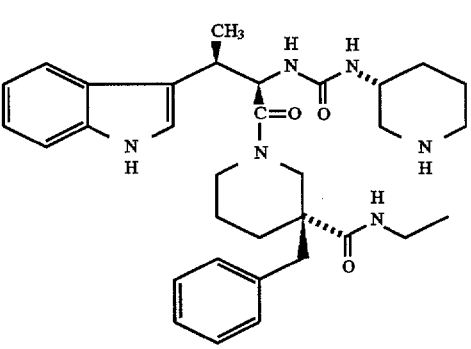
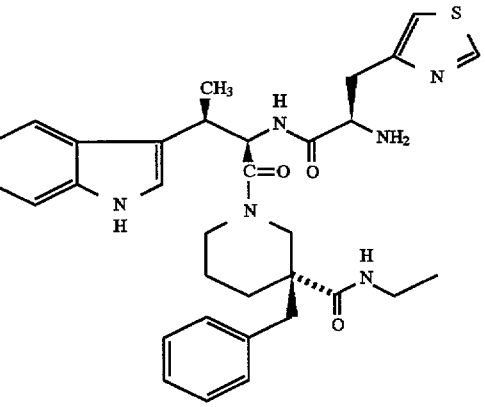
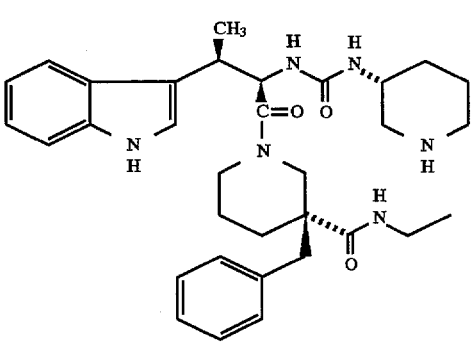

21
-continued
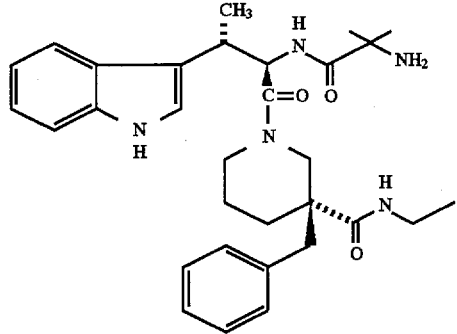
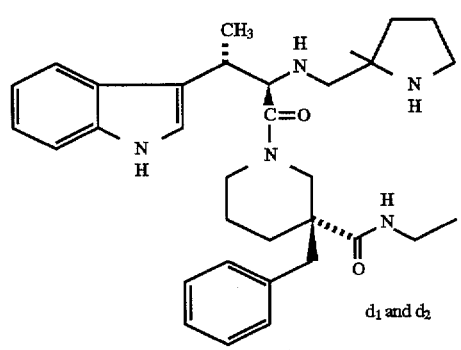
d₁ and d₂
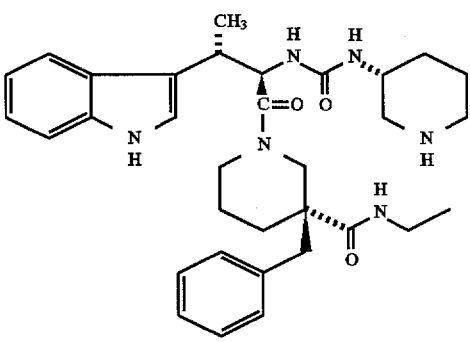
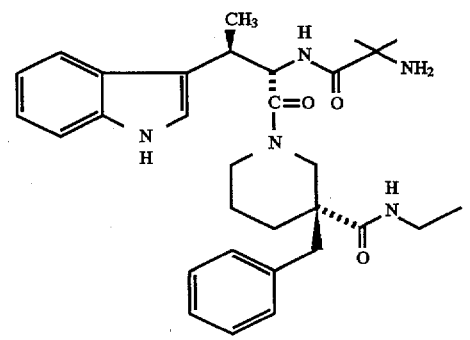
22
-continued
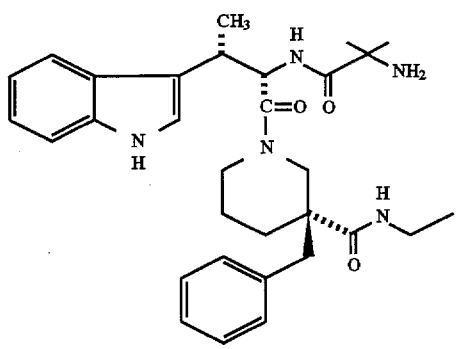
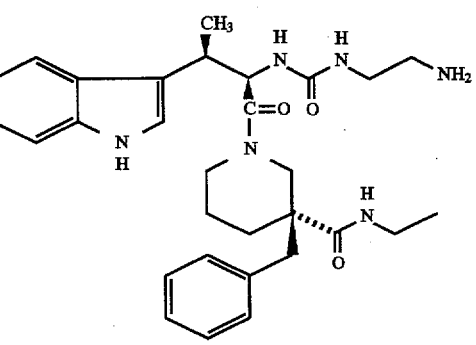
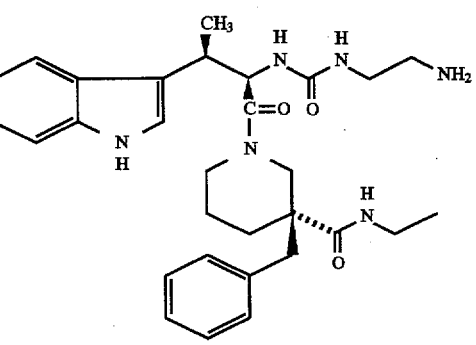
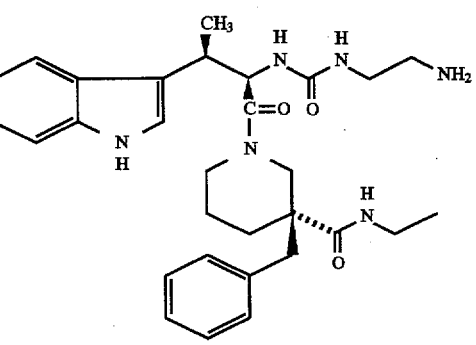

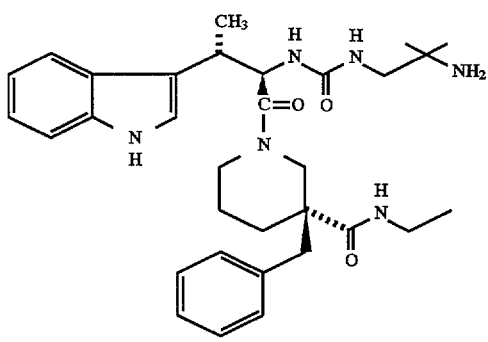

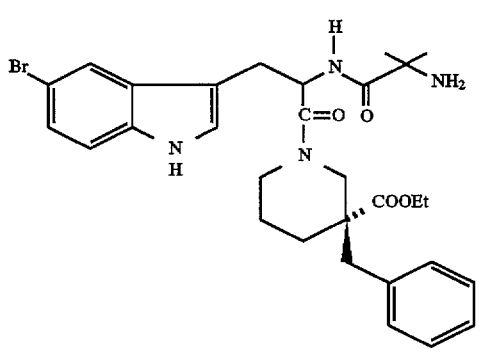

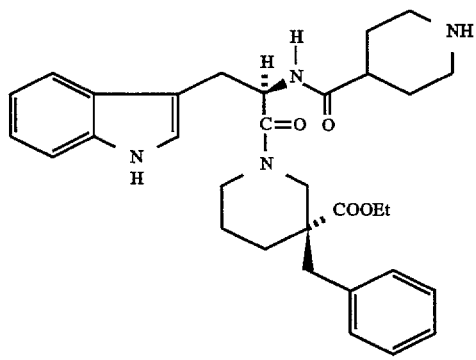

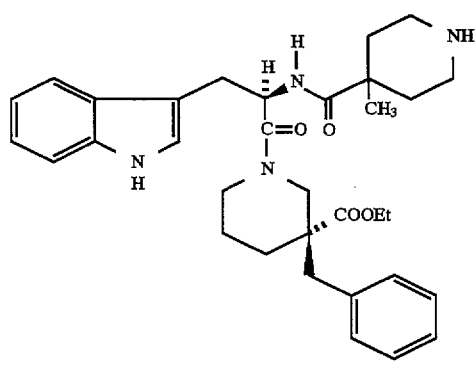

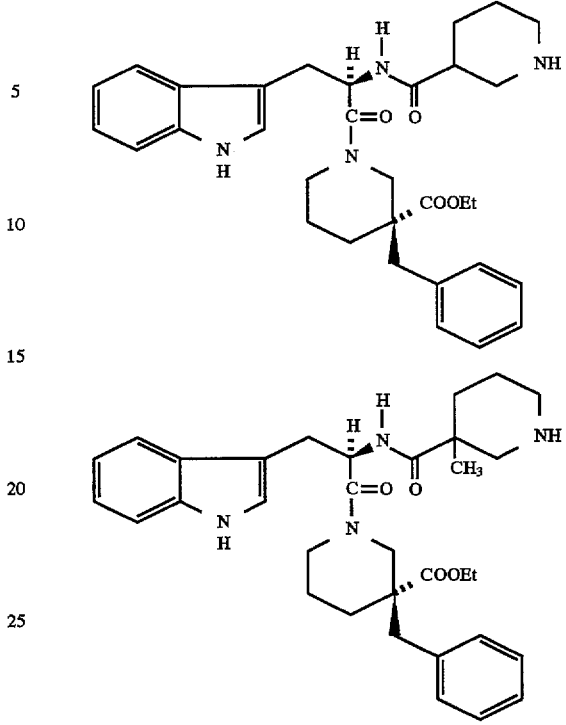

and pharmaceutically acceptable salts and individual diastereomers thereof where not otherwise specified.

Throughout the instant application, the following abbreviations are used with the following meanings:

| | |
|---|---|
| Bu | butyl |
| Bn | benzyl |
| BOC, Boc | t-butyloxycarbonyl |
| BOP | Benzotriazol-1-yloxy tris(dimethylamino)-phosphonium hexafluorophosphate |
| calc. | calculated |
| CBZ, Cbz | Benzyloxycarbonyl |
| DCC | Dicyclohexylcarbodiimide |
| DMF | N,N-dimethylformamide |
| DMAP | 4-Dimethylaminopyridine |
| EDC | 1-(3-dimethylaminopropyl)-3-ethylcarbodi-imide hydrochloride |
| EI-MS | Electron ion-mass spectroscopy |
| Et | ethyl |
| eq. | equivalent(s) |
| FAB-MS | Fast atom bombardment-mass spectroscopy |
| HOBT, HOBt | Hydroxybenztriazole |
| HPLC | High pressure liquid chromatography |
| KHMDS | Potassium bis(trimethylsilyl)amide |
| LAH | Lithium aluminum hydride |
| LHMDS | Lithium bis(trimethylsilyl)amide |
| Me | methyl |
| MF | Molecular formula |
| MHz | Megahertz |
| MPLC | Medium pressure liquid chromatography |
| NMM | N-Methylmorpholine |
| NMR | Nuclear Magnetic Resonance |
| Ph | phenyl |
| Pr | propyl |
| prep. | prepared |
| TFA | Trifluoroacetic acid |
| THF | Tetrahydrofuran |
| TLC | Thin layer chromatography |
| TMS | Tetramethylsilane |

The compounds of the instant invention all have at least two asymmetric centers when both X and Y are groups other than hydrogen and are different from each other. Additional asymmetric centers may be present depending upon the nature of the various substituents on the molecule. Each such asymmetric center will independently produce two optical isomers and it is intended that all of the possible optical isomers and diastereomers in mixture and as pure or partially purified compounds are included within the ambit of this invention. In the case of the asymmetric carbon atom represented by an asterisk in Formula I, it has been found that compounds are more active as growth hormone secretagogues and, therefore preferred, in which the nitrogen substituent is above and the hydrogen atom is below the plane of the structure as represented in Formula II. An equivalent representation places $R_1$ and the N-substituent in the plane of the structure with the C=O group above. This configuration corresponds to that present in a D-amino acid. In most cases, this is also designated an R-configuration, although this will vary according to the value of $R_1$ used in making R- or S-stereochemical assignments. In the case of the asymmetric center which bears the X and Y groups, in most cases, both R- and S-configurations are consistent with useful levels of growth hormone secretagogue activity. In addition configurations of many of the most preferred compounds of this invention are indicated. When the carbon atom in Formula I bearing an asterisk is of a defined and usually a D-configuration, two diastereomers result according to the absolute configuration at the carbon atom bearing the X and Y groups.

Surprisingly, certain compounds possessing both the L-configuration and a Beta-alkyl group, in particular, a Beta-methyl group, have also been found exhibit high activity as growth hormone secretagogues.

Diastereomers may arise from the presence of asymmetric centers in the present compounds. They are designated diastereomer 1 ($d_1$) and diastereomer 2 ($d_2$) and, if desired, their independent syntheses or chromatographic separations may be achieved as described herein. Their absolute stereochemistry may be determined by the x-ray crystallography of crystalline products or crystalline intermediates which are derivatized, if necessary, with a reagent containing an asymmetric center of known absolute configuration.

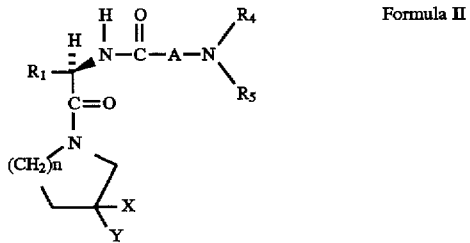

Formula II

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic, methane sulfonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

The preparation of compounds of Formula I of the present invention may be carried out in sequential or convergent synthetic routes. Syntheses detailing the preparation of the compounds of Formula I in a sequential manner are presented in the following reaction schemes.

The phrase "standard peptide coupling reaction conditions" is used repeatedly here, and it means coupling a carboxylic acid with an amine using an acid activating agent such as EDC, DCC, and BOP in a inert solvent such as dichloromethane in the presence of a catalyst such as HOBT. The uses of protective groups for amine and carboxylic acid to facilitate the desired reaction and minimize undesired reactions are well documented. Conditions required to remove protecting groups which may be present and can be found in Greene, T, and Wuts, P. G. M., *Protective Groups in Organic Synthesis*, John Wiley & Sons, Inc., New York, N.Y. 1991. CBZ and BOC were used extensively in the synthesis, and their removal conditions are known to those skilled in the art. For example, removal of CBZ groups can be achieved by a number of methods known in the art; for example, catalytic hydrogenation with hydrogen in the presence of a nobel metal or its oxide such as palladium on activated carbon in a protic solvent such as ethanol. In cases where catalytic hydrogenation is contraindicated by the presence of other potentially reactive functionality, removal of CBZ groups can also be achieved by treatment with a solution of hydrogen bromide in acetic acid, or by treatment with a mixture of TFA and dimethylsulfide. Removal of BOC protecting groups is carried out in a solvent such as methylene chloride or methanol or ethyl acetate, with a strong acid, such as trifluoroacetic acid or hydrochloric acid or hydrogen chloride gas.

The protected amino acid derivatives 1 are, in many cases, commercially available, where the protecting group L is, for example, BOC or CBZ groups. Other protected amino acid derivatives 1 can be prepared by literature methods (Williams, R. M. *Synthesis of Optically Active α-Amino Acids*, Pergamon Press: Oxford, 1989). Many of the piperidines, pyrrolidines, and hexahydro-1H-azepines of Formula 2 are either commercially available or known in the literature and others can be prepared following literature methods described for analogous compounds. Some of these methods are illustrated in the subsequent schemes. The skills required in carrying out the reaction and purification of the resulting reaction products are known to those in the art. Purification procedures includes crystallization, normal phase or reverse phase chromatography.

SCHEME 1

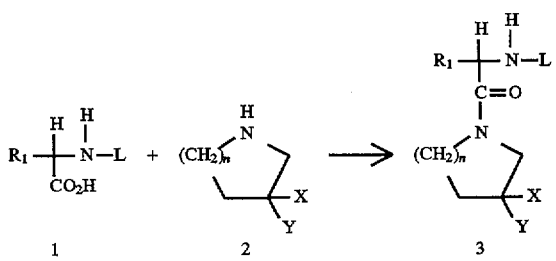

Intermediates of Formula 3 may be synthesized as described in Scheme 1. Coupling of amine of Formula 2, whose preparations are described later if they are not commercially available, to protected amino acids of Formula 1, wherein L is a suitable protecting group, is conveniently carried out under standard peptide coupling conditions.

SCHEME 2

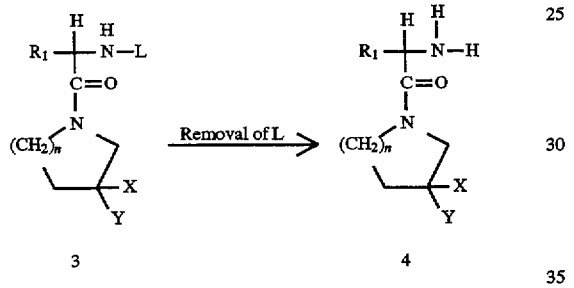

Conversion of 3 to intermediate 4 can be carried out as illustrated in Scheme 2 by removal of the protecting group L (CBZ, BOC, etc.)

Intermediates of Formula 5, wherein A is $-(CH_2)_x-C(R_7)(R_{7a})-(CH_2)_y-$ may be prepared as shown in Scheme 3 by coupling intermediates of Formula 4 to amino acids of Formula 5 under the standard peptide coupling reaction conditions. The amino acids 5, as amino acid 1, are either commercially available or can be synthesized by routine methods. Also if $R_4$ or $R_5$ is a hydrogen then the protected amino acids 6 are employed in the coupling reaction, wherein L is a protecting group as defined above. The removal of L in 7 to afford I, where $R_4$=H, can be carried out as noted above.

SCHEME 4

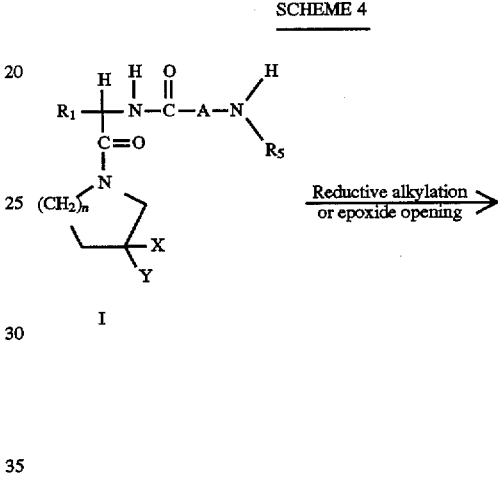

SCHEME 3

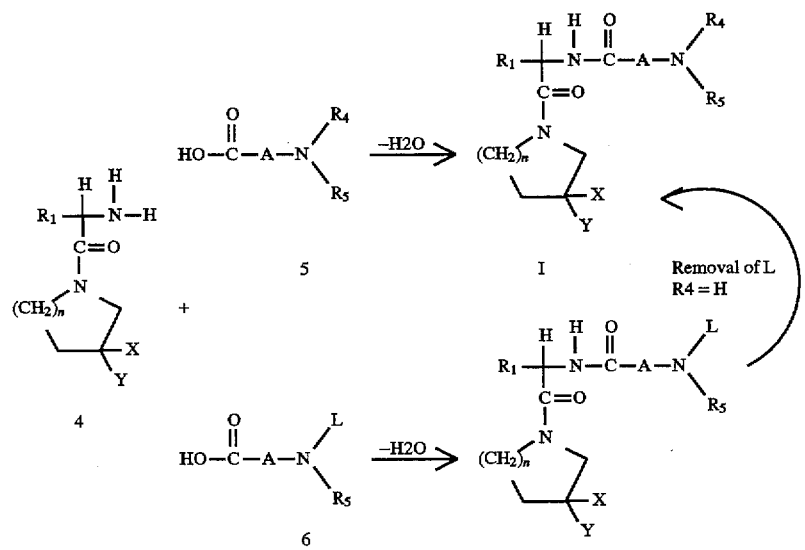

SCHEME 4 -continued

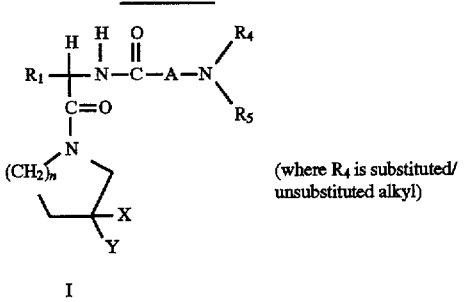

(where R₄ is substituted/unsubstituted alkyl)

Compounds of Formula I wherein $R_4$ and/or $R_5$ is a hydrogen may be further elaborated to new Compounds I (with most preferred side chains $R_4=CH_2—CH(OH)—CH_2X$, wherein X=H or OH) which are substituted on the amino group as depicted in Scheme 4. Reductive alkylation of I with an aldehyde is carried out under conditions known in the art; for example, by catalytic hydrogenation with hydrogen in the presence of platinum, palladium, or nickel catalysts or with chemical reducing agents such as sodium cyanoborohydride in a protic solvent such as methanol or ethanol in the present of catalytic amount of acid. Alternatively, a similar transformation can be accomplished via an epoxide opening reaction.

SCHEME 6

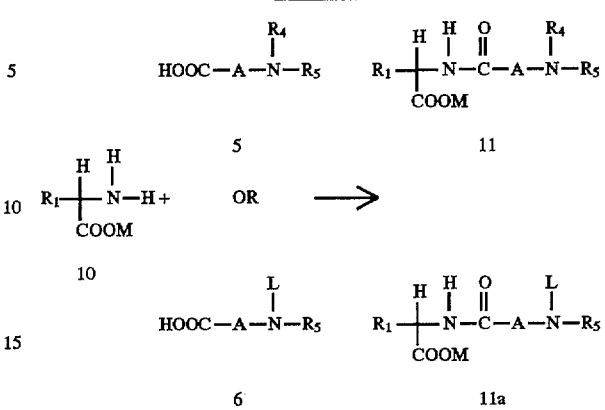

The compounds of general Formula I of the present invention may also be prepared in a convergent manner as described in reaction Schemes 6, 7 and 8.

The carboxylic acid protected amino acid derivatives 10 are, in many cases, commercially available where M=methyl, ethyl, or benzyl esters. Other ester protected amino acids can be prepared by classical methods familiar to those skilled in the art. Some of these methods include the reaction of the amino acid with an alcohol in the presence of an acid such as hydrochloric acid or p-toluenesulfonic acid and azeotropic removal of water. Other reactions includes the reaction of a protected amino acid with a diazoalkane, or with an alcohol and an acid activating agent such as EDC, DCC in the presence of a catalyst such as DMAP and removal of the protecting group L.

Intermediates of Formula 11 or 11a, may be prepared as shown in Scheme 6 by coupling of amino acid ester 10 to amino acids of Formula 6 or 7. When a urea or carbamate linkage is present in 11 or 11a, it can be introduced as illustrated in Scheme 5.

SCHEME 5

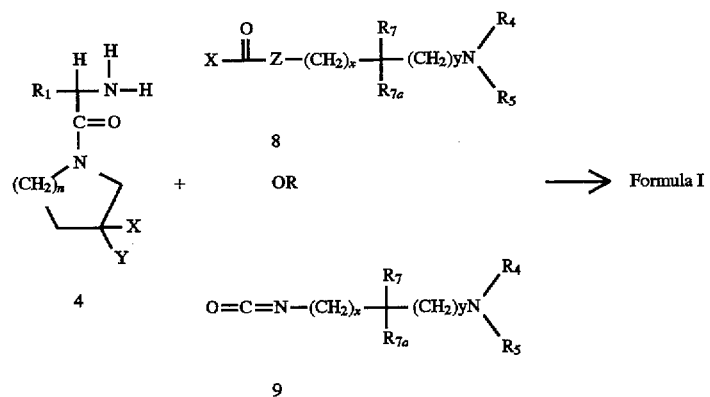

Compounds of Formula I, wherein A is $Z—(CH_2)_x—C(R_7)(R_{7a})—(CH_2)_y$ and Z is $N—R_6$ or O may be prepared as shown in Scheme 5 by reacting 4 with reagents 8, wherein X is a good leaving group such as Cl, Br, I, or imidazole. Alternatively, 4 may be reacted with an isocyanate of Formula 9 in an inert solvent such as 1,2-dichloroethane to provide compounds of Formula I where Z is NH.

SCHEME 7

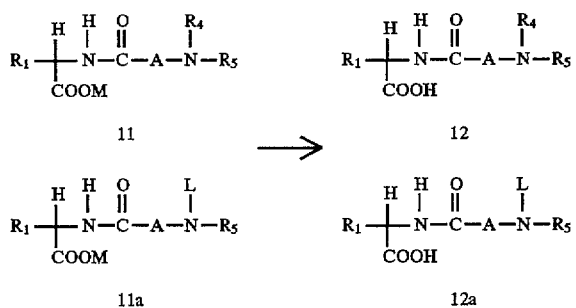

Conversion of the ester 11 or 11a to intermediate acids 12 or 12a may be achieved by a number of methods known in the art as described in Scheme 7; for example, methyl and ethyl esters can be hydrolyzed with lithium hydroxide in a protic solvent like aqueous methanol. In addition, removal of benzyl group can be accomplished by a number of reductive methods including hydrogenation in the presence of palladium catalyst in a protic solvent such as methanol. An allyl ester can be cleaved with tetrakis-triphenylphosphine palladium catalyst in the presence of 2-ethylhexanoic acid in a variety of solvents including ethyl acetate and dichloromethane (see *J. Org. Chem.*, 42, 587 (1982)).

SCHEME 8

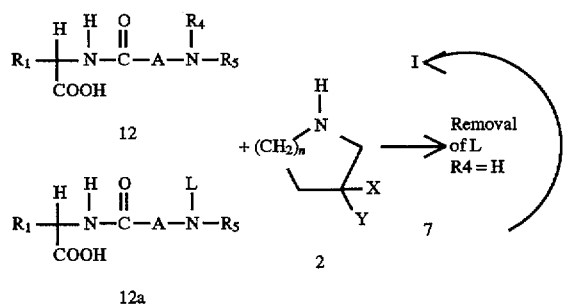

Acid 12 or 12a may then be elaborated to I or to I bearing protecting group L (Compound I) as described in Scheme 8. Coupling of piperidines pyrrolidines or hexahydro-1H-azepines of Formula 2 to acids of Formula 12 or 12a, is conveniently carried out under the standard peptide coupling reaction conditions. Transformation of 7 to I is achieved by removal of the protecting group L. When $R_4$ and/or $R_5$ is H, substituted alkyl groups may be optionally added to the nitrogen atom as described in Scheme 4.

SCHEME 9

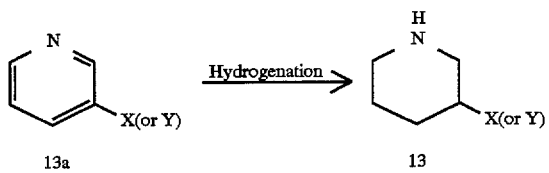

3-Monosubstituted piperidines of formula 13 can be prepared by the reduction of pyridine derivatives or their salts by hydrogenation in a suitable organic solvent such as water, acetic acid, alcohol, e.g. ethanol, or their mixture, in the presence of a noble metal catalyst such as platinum or an oxide thereof on a support such as activated carbon, and conveniently at room temperature and atmospheric pressure or under elevated temperature and pressure. 3-Monosubstituted piperidines can also be prepared by modification of the X or Y moiety of the existing 3-monosubstituted piperidines.

SCHEME 9A

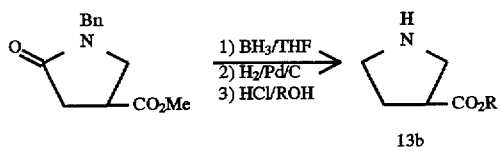

3-Monosubstituted pyrrolidines are commercially available or can be conveniently prepared by literature procedures. Shown in Scheme 9A is an example of the preparation of these compounds via pyrrolidine-3-carboxylic acid ester. The commercially available compound methyl 1-benzyl-4-oxo-3-pyrrolidinecarboxylate is reduced by borane (*J. Chem. Soc.*, 24, 1618–1619). Removal of the benzyl group by catalytic hydrogenolysis followed by ester exchange in an appropriate alcohol medium such as ethyl alcohol in the presence of acid gave the compound 13b. The ester functionality may be further modified through conventional chemistry to other groups as defined by X. 3-Monosubstituted pyrrolidines may also be prepared by catalytic hydrogenation of 3-substituted pyrroles.

SCHEME 9B

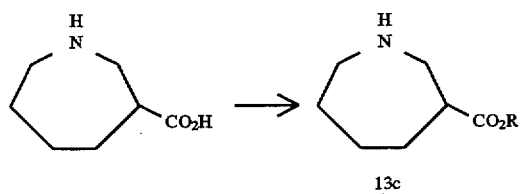

Hexahydro-1H-azepines are commercially available or may be prepared by the literature procedure. Hexahydro- 1H-azepine-3-carboxylic acid (Krogsgaard-Larsen, P. et al., *Acta. Chem. Scand.*, B32, 327, (1978)) is esterified in an alcohol solvent in the presence of acid. The ester functionality may be further modified through conventional chemistry to other groups within the definition of X.

SCHEME 10

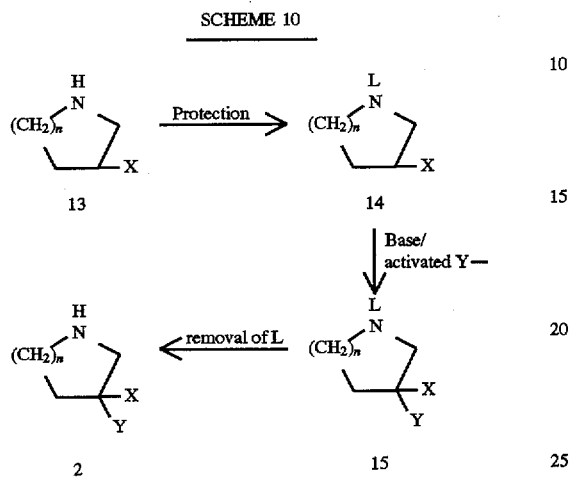

Illustrated in Scheme 10 is a general way to prepare disubstituted piperidines, pyrrolidines, and hexahydro-1H-azepines. Compounds of Formula 13 wherein X is an electron withdrawing group such as —CN, —CO$_2$R$_8$, where R$_8$ is alkyl, aryl, and (C$_1$–C$_4$alkyl)aryl are known compounds or may be prepared by methods analogous to those used for the preparation of such known compounds. The secondary amine of compounds of Formula 13 may be first protected by a protecting group L such as BOC and CBZ using the conventional techniques. Introduction of the Y substitution can be achieved by first reacting compounds of Formula 14 with a strong base such as lithium bis(trimethylsilyl)amide, lithium diisopropylamide following by addition of alkylating or acylating reagents such as alkyl halides, aryl alkyl halides, acyl halides, and haloformates in a inert solvent such as THF at temperatures from −100° to room temperature. Thio derivatives where the sulfur is attached directly to an alkyl or an aryl group can be prepared similarly by reacting with a disulfide. The halides used in these reactions are either commercially available or known compounds in the literature or may be prepared by methods analogous to those used for the preparation of known compounds. The protecting group L in compounds of formula 15 may be removed with conventional chemistry to give compounds of Formula 2.

SCHEME 11

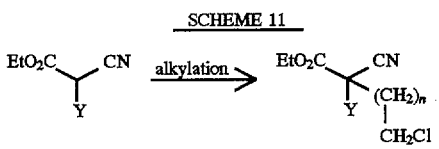

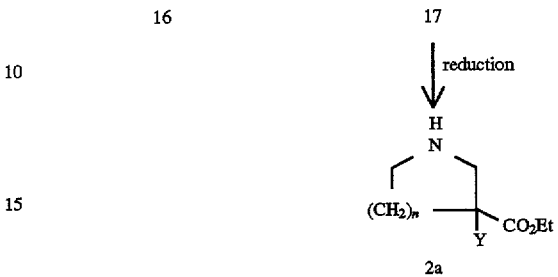

Alternative ways of preparing compounds of Formula 2 include construction of the ring itself (Jacoby, R. L. et al, *J. Med. Chem.*, 17, 453–455, (1974)). Alkylation of the cyanoacetates of general formula 16, which are commercially available or may be prepared from literature procedures, with alkyl dihalides such as 1-bromo-2-chloroethane or 1-bromo-3-chloropropane yields the chloride 17. Reduction of the nitriles by borane or by hydrogenation using Raney Ni as a catalyst gives the corresponding primary amines, which upon refluxing in ethanol to give compounds of Formula 2a.

SCHEME 12

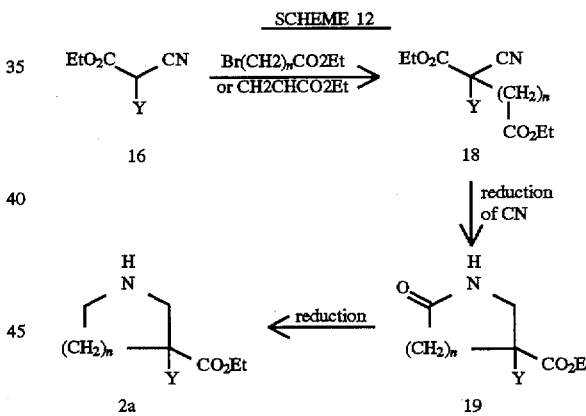

Alternatively, the cyanoacetates of general formula 16 may be alkylated with an ethoxycarbonylalkyl bromide or reacted with ethyl acrylate to give compounds of Formula 18. Reduction of the nitriles 18 by borane or by hydrogenation using Raney Ni as a catalyst gives the corresponding primary amines, which upon refluxing in ethanol gives lactam 19. Reduction of the lactam 19 by borane gives compounds of Formula 2a.

SCHEME 13

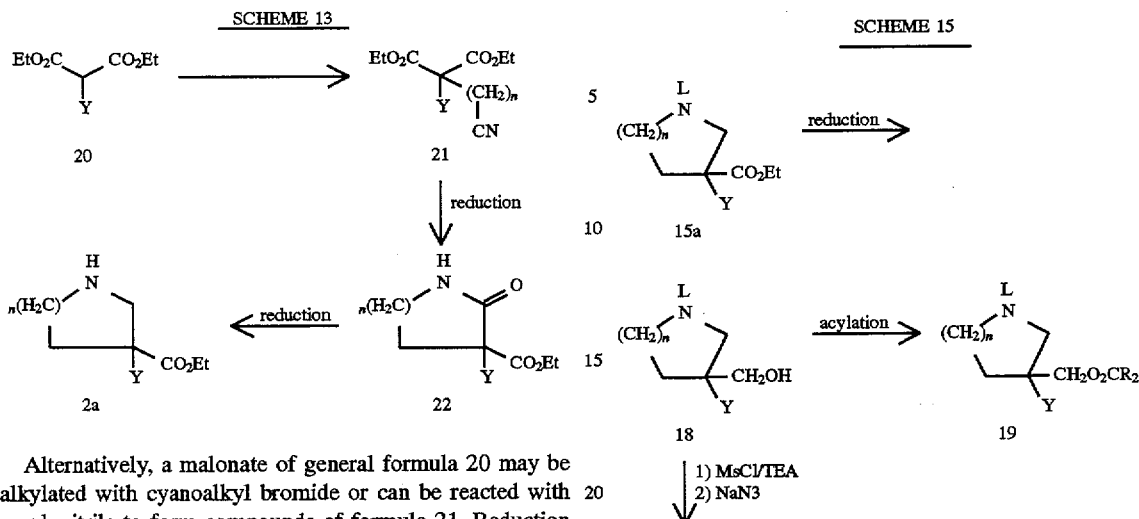

Alternatively, a malonate of general formula 20 may be alkylated with cyanoalkyl bromide or can be reacted with acrylonitrile to form compounds of formula 21. Reduction of the nitriles 21 by borane or by hydrogenation using Raney Ni as a catalyst gives the corresponding primary amines, which upon refluxing in ethanol gives lactam 22. Reduction of the lactam 22 by borane gives compounds of formula 2a.

SCHEME 14

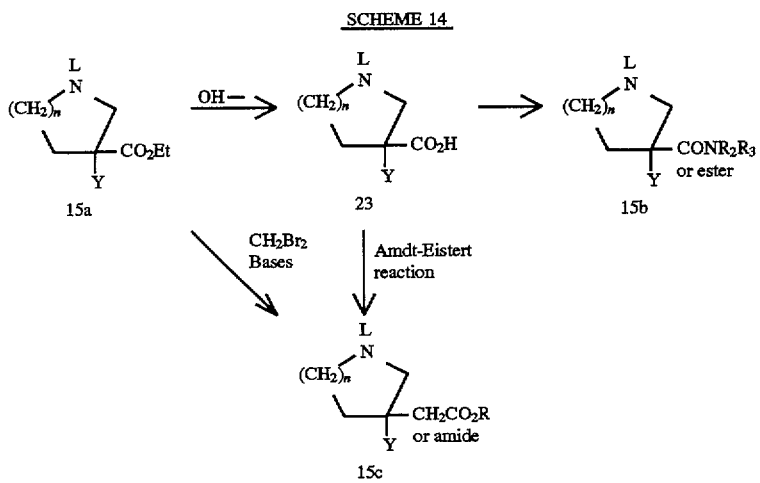

The X, Y functionalities in compounds of general structure 15 may be further elaborated to groups not accessible by direct alkylation. For example in Compound 15 when X=CO$_2$Et the ester (provided that this is the only ester group in the molecule) can be saponified to the carboxylic acid, which can be further derivatized to amides or other esters. The carboxylic acid can be converted into its next higher homologue, or to a derivative of the homologous acid, such as amide or ester by an Arndt-Eistert reaction. Alternatively, the ester can be directly homologated by the protocol using ynolate anions described by C. J. Kowalski and R. E. Reddy in *J. Org. Chem.*, 57, 7194–7208 (1992). The resulting acid and/or ester may be converted to the next higher homologue, and so on and so forth. The protecting group L may be removed through conventional chemistry.

SCHEME 15

(scheme shown at top right of page)

-continued
SCHEME 15

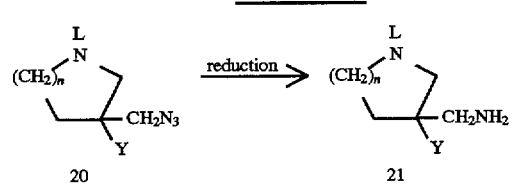

The ester in 15a may be reduced to an alcohol 18 in a suitable solvent such as THF or ether with a reducing agent such as DIBAL-H and conveniently carried out at temperatures from −100° C. to 0° C. The alcohol may be acylated to Compound 19 in a suitable solvent such as dichloromethane using an acyl halide or acid anhydride in the presence of a base such as triethyl amine (TEA). The hydroxy group in may also be converted to a good leaving group such as mesylate and displaced by a nucleophile such as cyanide, a thiol or an azide. Reduction of the azide in compounds of Formula 20 to an amine 21 can be achieved by hydrogenation in the presence of a noble metal such as palladium or its oxide or Raney nickel in a protic solvent such as ethanol. The nitrile can be reduced to afford the homologous amine. The amine of Formula 21 may be further elaborated to amides, ureas sulfonamides as defined by X through conventional chemistry. The protecting group L may be removed through conventional chemistry.

SCHEME 16

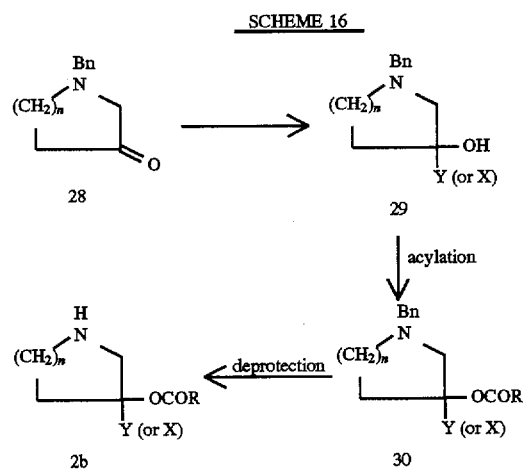

In cases where oxygen is directly attached to the ring, a convenient method involves the addition reaction by an activated form of an alkyl, aryl, alkylaryl group, such as lithium reagent, Grignard reagents, and the like with a ketone of general formula 28, which is commercially available. Further derivatization of the resulting hydroxy group by acylation, sulfonylation, alkylation, and the like gives compounds as defined by Y or X through conventional chemistry. Removal of the benzyl protective group may be carried out under the usual conditions to give compounds of general formula 2b. Shown in Scheme 16 is a general example of acylations.

SCHEME 17

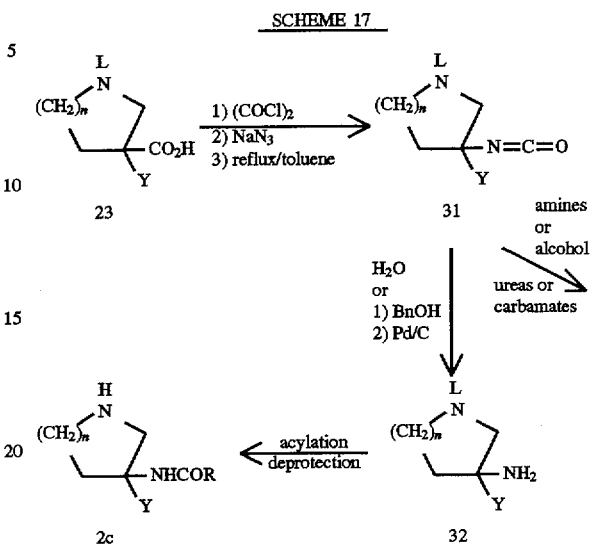

In cases where a nitrogen-substituted group is directly attached to the ring, a convenient method is to use the Curtius rearrangement on the acid 23 to afford the isocyanate 31. Addition of amines or alcohols give ureas or carbamates respectively which can be deprotected to remove L to give special cases of compounds of formula 2. Conversion of the isocyanate to amine by hydrolysis gives compound 32. Further derivatization of the resulting amine group by acylation, sulfonylation, alkylation, and the like to give compounds as defined by Y or X can be done through conventional chemistry. Removal of the protective group L may be carried out under the usual conditions to give compounds of general formula 2c. Shown in Scheme 17 is a general example of acylations.

SCHEME 18

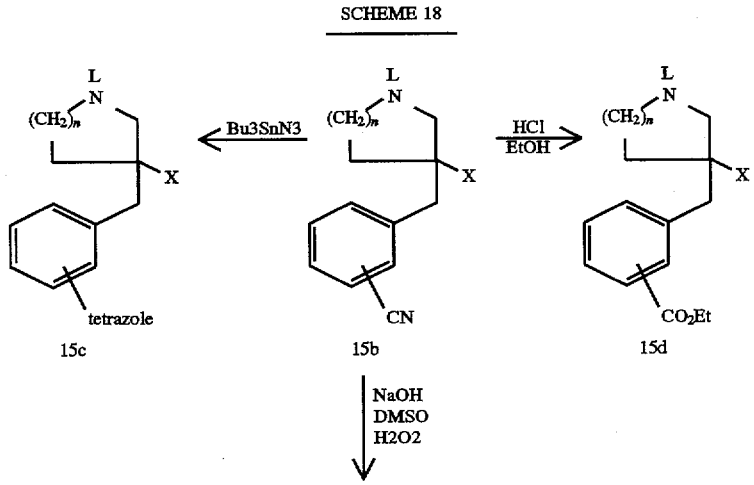

SCHEME 18 -continued

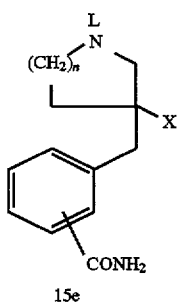

15e

For compounds that are not readily obtainable by direct alkylation as shown in Scheme 10, modifications of easily obtainable compounds of general formula 15 may be conducted to achieve the desired substitution through conventional chemistry. For example, compounds with Y being hydroxybenzyl may be prepared by demethylation of the corresponding compound wherein Y is methoxybenzyl. Similarly, compounds with Y being aminobenzyl may be prepared by reduction of the corresponding compound wherein Y is nitrobenzyl. Shown in Scheme 18 is an example of a procedure that uses nitrile as a starting point for the preparation of compounds with different substitutions. Removal of the protective group L gives compounds of general formula 2 as described in Scheme 10.

Compounds of the general formula 2 prepared in this way are racemic when X and Y are not identical. Resolution of the two enatiomers can be conveniently achieved by classical crystallization methods by using a chiral acid such as L- or D-tartaric acid, (+) or (−)-10-camphorsulfonic acid in a suitable solvent such as acetone, water, alcohol, ether, acetate or their mixture. Alternatively, the racemic amine 2 can be reacted with a chiral auxiliary such as (R) or (S)-O-acetylmandelic acid followed by chromatographic separation of the two diastereomers, and removal of the chiral auxiliary by hydrolysis. Alternatively asymmetric alkylation can also be utilized for the synthesis of optically active intermediate by introducing a removable chiral auxiliary in X or in place of L with subsequent chromatographic separation of diastereomers.

In cases where a sulfide is present in the molecule, it may be oxidized to a sulfoxide or to a sulfone with oxidizing agents such as sodium periodate, m-chloroperbenzoic acid or Oxone® in an solvent such as dichloromethane, alcohol or water or their mixtures.

The compounds of the present invention may also be prepared from a variety of substituted natural and unnatural amino acids of formulas 46. The preparation of many of these acids is described in U.S. Pat. No. 5,206,237. The preparation of these intermediates in racemic form is accomplished by classical methods familiar to those skilled in the art (Williams, R. M. "Synthesis of Optically Active α-Amino Acids" Pergamon Press: Oxford, 1989; Vol. 7). Several methods exist to resolve (DL)-

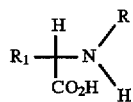

46 amino acids. One of the common methods is to resolve amino or carboxyl protected intermediates by crystallization of salts derived from optically active acids or amines.

Alternatively, the amino group of carboxyl protected intermediates may be coupled to optically active acids by using chemistry described earlier. Separation of the individual diastereomers either by chromatographic techniques or by crystallization followed by hydrolysis of the chiral amide furnishes resolved amino acids. Similarly, amino protected intermediates may be converted to a mixture of chiral diastereomeric esters and amides. Separation of the mixture using methods described above and hydrolysis of the individual diastereomers provides (D) and (L) amino acids. Finally, an enzymatic method to resolve N-acetyl derivatives of (DL)-amino acids has been reported by Whitesides and coworkers in *J. Am. Chem. Soc.* 1989, 111, 6354–6364.

When it is desirable to synthesize these intermediates in optically pure form, established methods include: (1) asymmetric electrophilic amination of chiral enolates (*J. Am. Chem. Soc.* 1986, 108, 6394–6395, 6395–6397, and 6397–6399), (2) asymmetric nucleophilic amination of optically active carbonyl derivatives, (*J. Am. Chem. Soc.* 1992, 114, 1906; *Tetrahedron Lett.* 1987, 28, 32), (3) diastereoselective alkylation of chiral glycine enolate synthons (*J. Am. Chem. Soc.* 1991, 113, 9276; *J. Org. Chem.* 1989, 54, 3916), (4) diastereoselective nucleophilic addition to a chiral electrophilic glycinate synthon (*J. Am. Chem. Soc.* 1986, 108, 1103), (5) asymmetric hydrogenation of prochiral dehydroamino acid derivatives ("*Asymmetric Synthesis, Chiral Catalysis*; Morrison, J. D., Ed; Academic Press: Orlando, Fla., 1985; Vol 5), and (6) enzymatic syntheses (*Angew. Chem. Int. Ed. Engl.* 1978, 17, 176).

SCHEME 19

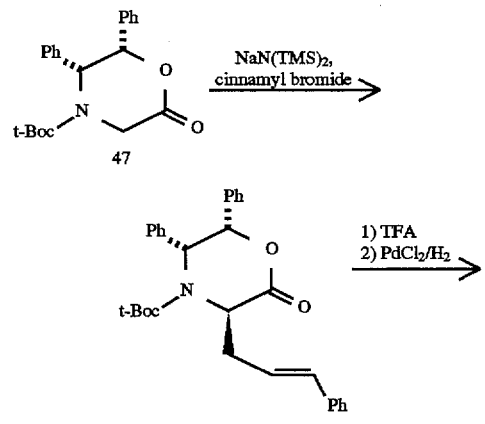

-continued
SCHEME 19

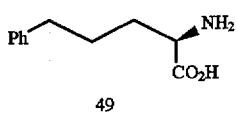

49

For example, alkylation of the enolate of diphenyloxazinone 47 (*J. Am. Chem. Soc.* 1991, 113, 9276) with cinnamyl bromide in the presence of sodium bis(trimethylsilyl)amide proceeds smoothly to afford which is converted into the desired (D)-2-amino-5-phenylpentanoic acid 49 by removing the N-t-butyloxycarbonyl group with trifluoroacetic acid and hydrogenation over a $PdCl_2$ catalyst (Scheme 19).

SCHEME 20

50       51

Intermediates of formula 46 which are O-benzyl-(D)-serine derivatives 51 are conveniently prepared from suitably substituted benzyl halides and N-protected-(D)-serine 50. The protecting group L is conveniently a BOC or a CBZ group. Benzylation of 64 can be achieved by a number of methods well known in the literature including deprotonation with two equivalents of sodium hydride in an inert solvent such as DMF followed by treatment with one equivalent of a variety of benzyl halides (Synthesis 1989, 36) as shown in Scheme 20.

The O-alkyl-(D)-serine derivatives may also be prepared using an alkylation protocol. Other methods that could be utilized to prepare (D)-serine derivatives of formula 51 include the acid catalyzed benzylation of carboxyl protected intermediates derived from 50 with reagents of formula $ArCH_2OC(=NH)CCl_3$ (O. Yonemitsu et al., *Chem. Pharm. Bull.* 1988, 36, 4244). Alternatively, alkylation of the chiral gylcine enolates (*J. Am. Chem. Soc.* 1991, 113, 9276; *J. Org. Chem.* 1989, 54, 3916) with $ArCH_2OCH_2X$ where X is a leaving group affords 51. In addition D,L-O-aryl(alkyl) serines may be prepared and resolved by methods described above.

It is noted that in some cases the order of carrying out the foregoing reaction schemes may be varied to facilitate the reaction or to avoid unwanted reaction products.

The utility of the compounds of the present invention as growth hormone secretagogues may be demonstrated by methodology known in the art, such as an assay disclosed by Smith, et al., *Science*, 260, 1640–1643 (1993) (see text of FIG. 2 therein). In particular, all of the compounds prepared in the following examples had activity as growth hormone secretagogues in the aforementioned assay. Such a result is indicative of the intrinsic activity of the present compounds as growth hormone secretagogues.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive peptides, e.g., bombesin, the neurokinins; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, to improve feed efficiency and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise an anabolic agent in addition to at least one of the compounds of Formula I or another composition which exhibits a different activity, e.g., an antibiotic growth permittant or an agent to treat osteoporosis or in combination with a corticosteroid to minimize the latter's catabolic side effects or with other pharmaceutically active materials wherein the combination enhances efficacy and minimizes side effects.

Growth promoting and anabolic agents include, but are not limited to, TRH, diethylstilbesterol, amino acids, estrogens, β-agonists, theophylline, anabolic steroids, enkephalins, E series prostaglandins, retinoic acid, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the compounds of this invention is in combination with other growth hormone secretagogues such as the growth hormone releasing peptides GHRP-6, GHRP-1 as described in U.S. Pat. No. 4,411,890 and publications WO 89/07110, WO 89/07111 and B-HT920 as well as hexarelin and GHRP-2 as described in WO 93/04081 or growth hormone releasing hormone (GHRH, also designated GRF) and its analogs or growth hormone and its analogs or somatomedins including IGF-1 and IGF-2 or α-adrenergic agonists such as clonidine or serotonin 5HTID agonists such as sumitriptan or agents which inhibit somatostatin or its release such as physostigmine and pyridostigmine. In particular, the compounds of this invention may be used in combination with growth hormone releasing factor, an analog of growth hormone releasing factor, IGF-1, or IGF-2. For example, a compound of the present invention may be used in combination with IGF-1 for the treatment or prevention of obesity. In addition, a compound of this invention may be employed in conjunction with retinoic acid to improve the condition of musculature and skin that results from intrinsic aging.

The present invention is further directed to a method for the manufacture of a medicament for stimulating the release of growth hormone in humans and animals comprising combining a compound of the present invention with a pharmaceutical carrier or diluent.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses may be summarized as follows: stimulating growth hormone release in elderly humans; treating growth hormone deficient adults; prevention of catabolic side effects of glucocorticoids; treatment of osteoporosis; stimulation of the immune system, acceleration of wound healing; accelerating bone fracture repair; treatment of growth retardation; treating acute or chronic renal failure or insufficiency; treatment of physiological short stature, including growth hormone deficient children; treating short stature associated with chronic illness; treating obesity and growth retardation associated with obesity; treating growth retardation associated with Prader-Willi syndrome and Turner's syndrome; accelerating the recovery and reducing hospitalization of burn patients or following major surgery such as gastrointestinal surgery; treatment of intrauterine growth retardation, and skeletal dysplasia; treatment of hypercortisonism and Cushing's syndrome; treatment of peripheral neuropathies; replacement of growth hormone in stressed patients; treatment of osteochondrodysplasias, Noonans syndrome, sleep disorders, schizophrenia, depression, Alzheimer's disease, delayed wound healing, and psychosocial deprivation; treatment of pulmonary dysfunction and ventilator dependency; prevention or treatment of congestive heart failure, improving pulmonary function, restoring systolic and diastolic function, increasing myocardial contractility, decreasing peripheral total vascular resistance, diminishing or preventing loss of body weight and enhancing recovery following congestive heart failure; increasing appetite; attenuation of protein catabolic response after a major operation; treating malabsorption syndromes; reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction and to prevent and treat gastric and duodenal ulcers; stimulation of thymic development and preventtion of the age-related decline of thymic function; adjunctive therapy for patients on chronic hemodialysis; treatment of immunosuppressed patients and to enhance antibody response following vaccination; increasing the total lymphocyte count of a human, in particular, increasing the $T_4/T_8$-cell ratio in a human with a depressed $T_4/T_8$-cell ratio resulting, for example, from infection, such as bacterial or viral infection, especially infection with the human immunodeficiency virus; treatment of syndromes manifested by non-restorative sleep and musculoskeletal pain, including fibromyalgia syndrome or chronic fatigue syndrome; improvement in muscle strength, mobility, maintenance of skin thickness, metabolic homeostasis, renal hemeostasis in the frail elderly; stimulation of osteoblasts, bone remodelling, and cartilage growth; stimulation of the immune system in companion animals and treatment of disorders of aging in companion animals; growth promotant in livestock; and stimulation of wool growth in sheep. Further, the instant compounds are useful for increasing feed efficiency, promoting growth, increasing milk production and improving the carcass quality of livestock. Likewise, the instant compounds are useful in a method of treatment of diseases or conditions which are benefited by the anabolic effects of enhanced growth hormone levels that comprises the administration of an instant compound.

In particular, the instant compounds are useful in the prevention or treatment of a condition selected from the group consisting of: osteoporosis; catabolic illness; immune deficiency, including that in individuals with a depressed $T_4/T_8$ cell ratio; bone fracture, including hip fracture; musculoskeletal impairment in the elderly; growth hormone deficiency in adults or in children; short stature in children; obesity; sleep disorders; cachexia and protein loss due to chronic illness such as AIDS or cancer; and treating patients recovering from major surgery, wounds or burns, in a patient in need thereof.

In addition, the instant compounds may be useful in the treatment of illnesses induced or facilitated by corticotropin releasing factor or stress- and anxiety-related disorders, including stress-induced depression and headache, abdominal bowel syndrome, immune suppression, HIV infections, Alzheimer's disease, gastrointestinal disease, anorexia nervosa, hemorrhagic stress, drug and alcohol withdrawal symptoms, drug addiction, and fertility problems.

It will be known to those skilled on the art that there are numerous compounds now being used in an effort to treat the diseases or therapeutic indications enumerated above. Combinations of these therapeutic agents some of which have also been mentioned above with the growth hormone secretagogues of this invention will bring additional, complementary, and often synergistic properties to enhance the growth promotant, anabolic and desirable properties of these various therapeutic agents. In these combinations, the therapeutic agents and the growth hormone secretagogues of this invdose ranges from independently present in dose ranges from one one-hundredth to one times the dose levels which are effective when these compounds and secretagogues are used singly.

Combined therapy to inhibit bone resorption, prevent osteoporosis and enhance the healing of bone fractures can be illustrated by combinations of bisphosphonates and the growth hormone secretagogues of this invention. The use of bisphosphonates for these utilities has been reviewed, for example, by Hamdy, N. A. T. Role of Bisphosphonates in Metabolic Bone Diseases. *Trends in Endocrinol. Metab.*, 4, 19–25 (1993). Bisphonates with these utilities include alendronate, tiludronate, dimethyl-APD, risedronate, etidronate, YM-175, clodronate, pamidronate, and BM-210995. According to their potency, oral daily dosage levels of the bisphosphonate of between 0.1 mg and 5 g and daily dosage levels of the growth hormone secretagogues of this invention of between 0.01 mg/kg to 20 mg/kg of body weight are administered to patients to obtain effective treatment of osteoporosis.

In the case of alendronate daily oral dosage levels of 0.1 mg to 50 mg are combined for effective osteoporosis therapy with 0.01 mg/kg to 20 mg/kg of the growth hormone secretagogues of this invention.

Osteoporosis and other bone disorders may also be treated with compounds of this invention in combination with calcitonin, estrogens, raloxifene and calcium supplements such as calcium citrate or calcium carbonate.

Anabolic effects especially in the treatment of geriatric male patients are obtained with compounds of this invention in combination with anabolic steroids such as oxymetholone, methyltesterone, fluoxymesterone and stanozolol.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, and elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 10 mg/kg. of body weight daily are administered to patients and animals, e.g., mammals, to obtain effective release of growth hormone. Preferably, the dosage level will be about 0.001 to about 25 mg/kg per day; more preferably about 0.01 to about 10 mg/kg per day.

The following examples are provided for the purpose of further illustration only and are not intended to be limitations on the disclosed invention.

INTERMEDIATE 1

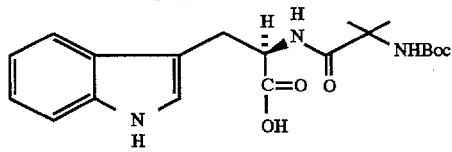

Step A:

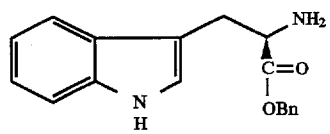

To a solution of the commercially available N-t-BOC-D-tryptophan (25.0 g, 82.2 mmol), benzyl alcohol (10.2 mL, 98.6 mmol), and DMAP (100 mg) in dichloromethane (200 mL) at 0° C., was added EDC (17.4 g, 90.4 mmol) in several portions over a one hour period. The reaction mixture was stirred at room temperature for six hours and was poured into water (200 mL), and the organic layer was separated. The organic solution was washed with a mixture of brine and 3N hydrochloric acid, dried over anhydrous magnesium sulfate, filtered and concentrated to give a thick oil, which solidified upon standing.

To a solution of this oil in 30 mL of dichloromethane was added 20 mL of TFA and stirred for 1 h. The reaction mixture was concentrated, neutralized carefully with saturated aqueous sodium bicarbonate solution, and extracted with dichloromethane (2×100 mL). The combined organic solution was washed with brine (100 mL), passed through a short column of silica gel eluting with 5–10% methanol in dichloromethane to give 23.2 g of the amine as an oil after evaporation.

Step B:

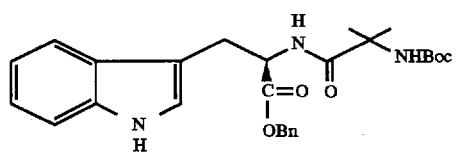

To a solution of the above product, HOBT (10.6 g, 78.8 mmol) and N-BOC-α-methyl alanine (19 g, 94.5 mmol) in 200 mL of dichloromethane, was added EDC (19.5 g, 0.102 mol) in several portions at 0° C. After 5 minutes, the clear reaction mixture became milky. After stirring at room temperature overnight, the reaction mixture was poured into 200 mL of water and the organic layer was separated. The organic solution was washed with brine, and with a brine and saturated sodium bicarbonate solution, dried over anhydrous magnesium sulfate, filtered and concentrated to give a thick oil, which was purified by flash chromatography eluting with 10–40% ethyl acetate in hexane to give the desired material (28.7 g).

$^1$H NMR (CDCl$_3$, 200 MHz) δ 8.48 (br.s, 1H), 7.54 (br.d, 1H), 7.38–7.23 (m, 3H), 7.19 (br.d, 2H), 7.15–7.00 (m, 1H), 6.90 (d, 1H), 6.86 (d, 1H), 5.06 (br.s, 2H), 4.95 (ddd, 1H), 3.30 (2dd, 2H), 1.40 (s, 15H)

Step C:

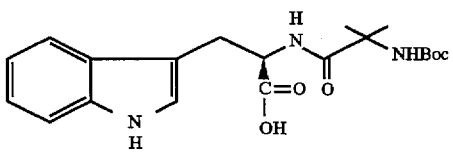

A solution of the material from Step B (28.7 g) in 200 mL of ethanol was stirred at RT under a H₂ balloon for 20 minutes in the presence of 10% palladium on carbon (2 g). The catalyst was filtered off through a pad of celite and washed with ethyl acetate. The filtrate was concentrated to give the acid as a slightly pink foam (23.3 g).

¹H NMR (CD₃OD, 400 MHz) δ 7.56 (d, J=8 Hz, 1H), 7.31 (dd, J=J=1,8 Hz, 1H), 7.09 (s, 1H), 7.07 (dt, J=1, 7 Hz, 1H), 6.98 (dt, J=1, 7 Hz, 1H), 4.69 (t, J=6 Hz, 1H), 3.34–3.23 (m, 2H), 1.35 (s, 3H), 1.34 (s, 9H), 1.29 (s, 3H).

FAB-MS calc. for $C_{20}H_{27}N_3O_5$: 389; Found 390 (M+H), 290 (M+H–100 (BOC))

INTERMEDIATE 2

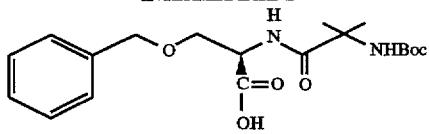

Following the procedures for the preparation of Intermediate 1 using N-t-Boc-O-Benzyl-D-serine in the place of N-t-BOC-D-tryptophan gave Intermediate 2. FAB-MS calc. for $C_{19}H_{28}N_2O_6$: 380; Found 381 (M+H), 325 (M+H–56 (t-Bu)), 281 (M+H–100 (BOC)).

INTERMEDIATE 3

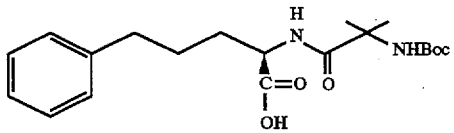

Step A:

(DL)-N-Acetyl-2-amino-5-phenylpentanoic acid

To a solution of sodium (2.3 g, 0.1 mol) in ethanol (60 mL) under nitrogen at room temperature, was added diethyl acetamidomalonate. The mixture was stirred at room temperature for one hour, and then 1-bromo-3-phenylpropane was added dropwisely. After the addition, the mixture was stirred at room temperature for two hours, then refluxed overnight. It was cooled to room temperature and partitioned between water and ethyl acetate. The organic layer was washed with sodium bicarbonate in water, dried over MgSO₄ and evaporated to give an intermediate (32.5 g, 97%).

¹H NMR (CDCl₃, 400 MHz) 7.26–7.10 (m, 5H); 6.75 Cor. s, 1H); 4.19 (q, J=7 Hz, 4H); 2.58 (t, J=7.9 Hz, 2H); 2.39–2.35 (m, 2H); 2.00 (s, 3H); 1.43–1.39 (m, 2H); 1.20 (t, J=7 Hz, 6H).

The product above was suspended in 190 mL of 2.5N NaOH in water and refluxed for two hours. The mixture was cooled to 0° C., and it was carefully neutralized with 6N HCl to pH2. The precipitate was collected using a glass sinter funnel and washed with a small amount of cold water and air dried. The solid was then suspended in 300 mL of water and refluxed for four hours. The solution was cooled and acidified to pH and the solid was collected by filtration (15.3 g, 67%).

¹H NMR (CD3OD, 400 MHz) 7.26–7.12 (m, 5H); 4.90–4.37 (m, 1H); 2.65–2.60 (m, 2H); 1.97 (s, 3H); 1.87–1.82 (m, 1H); 1.73–1.65 (m, 3H).

Step B:

(D)-N-Acetyl-2-amino-5-phenylpentanoic acid

The racemic intermediate from the previous step (10 g, 42.5 mmol) and CoCl3–6H₂O were dissolved in 21 ml of 2N KOH and 200 mL of water at 40° C., and the pH of the solution was adjusted to 8 by the addition of the several drops of 2N KOH. Then acylase I (Aspergillus sp, 0.5 u/mg, from Sigma; 0.9 g) was added with vigorous stirring. The reaction mixture was stirred for one day at 40° C. and the pH was kept at 8 by the addition of a few drops of KOH. The solid which formed was faltered off. The filtrate was acidified by 3N HCl to pH2, and was extracted with ethyl acetate (200 mL×4). The organic extracts were combined and evaporated to give a white solid (4.64 g, 46%)

¹H NMR (CD3OD, 400 MHz) 7.26–7.12 (m, 5H); 4.90–4.37 (m, 1H); 2.65–2.60 (m, 2H); 1.97 (s, 3H); 1.87–1.82 (m, 1H); 1.73–1.65 (m, 3H).

Step C:

(D)-N-t-Boc-2-amino-5-phenylyentanoic acid

The intermediate from step B (4.2 g, 17.8 mmol) was suspended in 2N HCl (100 mL) and refluxed for two hours. The reaction mixture was evaporated in vacuo to remove water and hydrochloric acid to yield a white solid. To a solution of this solid in 50 mL of water, was added 3N NaOH until the pH 11, then di-t-butyl dicarbonate (4.66 g, 21.4 mmol) was added with vigorous stirring. After four hours, the reaction mixture was acidified to pH2 with 3N HCl and it was extracted with ethyl acetate (100 mL×3). The organic extracts were combined and evaporated to give a white solid (6.56 g, crude) which was used without purification. ¹H NMR (CD3OD, 400 MHz) 7.26–7.12 (m, 5H); 4.11–4.08 (m, 1H); 2.65–2.60 (m, 2H); 1.83–1.62 (m, 4H); 1.43 (s, 9H).

Step D:

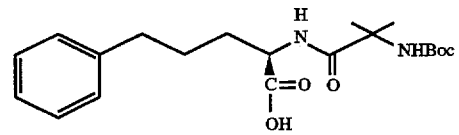

Following the procedures for the preparation of Intermediate 1 using (D)-N-t-Boc-2-amino-5-phenylpentanoic acid in the place of N-t-BOC-D-tryptophan gave Intermediate 3. ¹H NMR (CDCl₃, 400 MHz) 7.24–7.20 (m, 2H), 7.15–7.04 (m, 3H), 4.60–4.55 (m, 1H), 2.62–2.55 (m, 2H), 2.00–1.86 (m, 1H), 1.78–1.60 (m, 3H), 1.50 (s, 6H), 1.30 (s, 9H).

EXAMPLE A1

N-acetyl- Threo-(2R,3S)-β-methyltryptophan R-(+)-α-methylbenzyl amine salt

Racemic N-acetyl β-methyltryptophan was prepared by the method of Snyder and Matteson (J. Am. Chem. Soc. 1957, 79, 2217). Isomer A (100 g) was suspended in 1.25 L of 90/10 acetone water at 20° C. and 50 mL of R-(+)-(α-methylbenzylamine was added in one portion. The suspension cleared briefly before a thick white suspension formed which quickly mined to a solid mass. After aging overnight, an additional 500 mL of acetone was added to facilitate agitation and filtration. The suspension was filtered and the cake washed with 500 mL of acetone and sucked to a damp cake. The solid was suspended in 2.5 L of 90/10 acetone/water and heated to boiling on a steam bath. The white slurry was allowed to cool to 20° C. overnight. The product was collected by filtration, washed with acetone and dried yielding 39.1 g of the tide compound. α=+9.1° (c=1, MeOH). Stereochemical assignments were made by comparison to published compounds: *J. Org. Chem.* 1994, 59, 4239 and *J. Org. Chem.* 1995, 60, 4978.

EXAMPLE A2

N-acetyl-Threo-(2S,3R)-15-methyltryptophan S-(−)-α-methylbenzyl amine salt

The mother liquors from Example A1 were combined and concentrated to ca. 1 L and 400 mL of 1N HCl was added. The resulting suspension was stirred for 1 hr initially at 20° C. then at 0° C. The product was filtered and washed with water until the filtrate was neutral. The product was sucked to a damp cake weighing 79 g. The solid was suspended in 1L of 95% acetone/water and 40 mL of S-(−)-α-methylbenzylamine was added followed by 1 L of 90% acetone/water. After a few minutes a solid mass formed. An additional 500 mL of acetone was added and the mixture heated on a steam bath for ca. 0.5 hr. This was then allowed to stand at 20° C. overnight. The product was collected by filtration, washed with 500 mL of acetone, and sucked to a damp cake. The product was suspended in 2 L of 95% acetone/water and heated on a steam bath to boiling. The white suspension was allowed to cool to 20° C. overnight. The product was collected by filtration, washed with 500 mL of acetone and dried yielding 54 g. α=−9.0° (c=1, MeOH).

EXAMPLE A3

N-acetyl-Erythro(2R,3R)-15-methyltryptophan R-(+)-α-methylbenzyl amine salt 170 g of Isomer B (prepared as described by the reference in Example A1) which was a brittle foam containing ethyl acetate was dissolved in 2.5 L of ethyl acetate containing 100 mL of ethanol. To this was added 60 mL of R-(+)-α-methylbenzylamine. After 10 min, an additional 2 L of ethyl acetate was added and the resulting thick suspension was aged at 20° C. for 3 days. The product was collected by filtration, washed with ethyl acetate and and sucked to a damp cake. The salt was re-slurried four times with hot ethyl acetate containing 2% water (1×2.5 L, 2×6 L, and 1×8 L). The yield of dried product was 43.2 g of salt. α=−19.6° (c=1, MeOH).

EXAMPLE A4

N-acetyl-Erythro(2S,3S)-β-methyltryptophan S-(−)-α-methylbenzyl amine salt

The mother liquors from Example A3 were combined and concentrated to ca. 2 L and washed twice with 500 mL 1N HCl. The washes were back extracted once with ethyl acatate, and the combined ethyl acetate extracts washed twice with brine. The solution was diluted to 6 L with ethyl acatate and 60 mL of S-(−)-α-methylbenzylamine was added. After 10 min the resulting suspension was heated to boiling. The suspension was allowed to cool to ambient temperature with stirring overnight. The product was collected by filtration washed with ethyl acetate and and sucked to a damp cake. The salt was suspended in 6 L of ethyl acetate and suspension was heated to boiling. The suspension was allowed to cool to ambient temperature with stirring overnight. The product was collected by filtration washed with ethyl acetate and dried. The yield of dried product was 65.8 g of salt. α=+19.7° (c=1, MeOH).

EXAMPLE A5

N-acetyl-threo-(2S,3R)-β-methyltryptophan

The salt from Example A2 (53 g) was stirred with 400 mL 1N HCl at 20° C. for 20 min. The suspension was filtered and the cake washed with water until the filtrate was neutral. The wet cake was used directly for the next reaction. A sample was dried affording the title compound. α=−26.4° (c=1, MeOH).

EXAMPLE A6 threo-(2S,3R)-β-methyltryptophan

The wet cake from Example A5 was suspended in with 400 mL of 1N HCl and refluxed for 12 hours. The solution was cooled to 20° C., and half of the solution was used for Example A7. The title compound was isolated by adjusting the pH to 7.0 with sodium hydroxide, cooling the resulting suspension to 0° C., filtering, washing the cake with water and drying. α=−29.3° (c=0.9, H$_2$O).

EXAMPLE A7

N-t-BOC-threo-2(2S,3R)-β-methyltryptophan

The pH of the aqueous solution from Example A6 was adjusted to 7 with sodium hydroxide and cooled to 0° C. 20 g of potassium carbonate, 19 g of di-t-butyldicarbonate, and 150 mL of THF were added. The mixture was allowed to warm slowly to ambient temperature overnight. The reaction was extracted twice with ether, the aqueous acidified with 2N HCl and extracted twice with ethyl acetate. The combined ethyl acetate extracts were washed with brine, dried with MgSO$_4$, filtered and concentrated affording 21.2 g of the title compound.

EXAMPLE A8

N-acetyl-threo-(2R,3S)-β-methyltryptophan

The title compound was prepared essentially following the proceedure of Example A5. α=+26.6° (c=1, MeOH).

EXAMPLE A9 threo-(2R,3S)-β-methyltryptophan

The title compound was prepared essentially following the proceedure of Example A6. α=+30.6° (c=0.9, H$_2$O).

EXAMPLE A10

N-t-BOC-threo-(2R,3R)-β-methyltryptophan

The title compound was prepared essentially following the proceedure of Example A7.

EXAMPLE A11

N-acetyl Erythro(2S,3S)-β-methyltryptophan

The salt from Example A4 (65 g) was stirred with 250 mL 1N HCl and 1.5 L of ethyl acetate at ambient temperature for 5 min. The layers were partitioned and the ethyl acetate layer was washed with 1N HCl, H$_2$O and brine, dried with MgSO₄, filtered and concentrated to afford the title compound as a brittle foam.

EXAMPLE A12

Erythro(2S,3S)-β-methyltryptophan

The product from Example A11 was suspended in with 500 mL of 2N HCl and refluxed for 4 hours. The solution was cooled to 20° C., and half of the solution was used for Example A13. The title compound isolated as a foam by concentrating the solution in vacuo.

EXAMPLE A13

N-t-BOC-Erythro(2S,3S)-β-methyltryptophan

The pH of the aqueous solution from Example A6 was adjusted to 7 with sodium hydroxide and cooled to 0° C. 24 g of potassium carbonate, 22 g of di-t-butyldicarbonate, and 150 mL of THF were added. The mixture was allowed to warm slowly to ambient temperature overnight. The reaction was extracted twice with ether The aqueous acidified with 2N HCl. and extracted twice with ethyl acetate. The combined ethyl acetate extracts were washed with brine, dried with MgSO₄ faltered and concentrated. The solid was redissolved in ether, and the ether removed in vacuo while flushing with hexanes. The resulting slurry was filtered and dried affording 20.1 g of the title compound.

EXAMPLE A14

N-acetyl-threo-(2R,3R)-β-methyltryptophan

The title compound was prepared essentially following the proceedure of Example A11.

EXAMPLE A15 threo-(2R,3R)-β-methyltryptophan

The title compound was prepared essentially following the proceedure of Example A12.

EXAMPLE A16

N-t-BOC-threo-(2R,3R)-β-methlyltryptophan

The title compound was prepared essentially following the proceedure of Example A13.

EXAMPLE 1

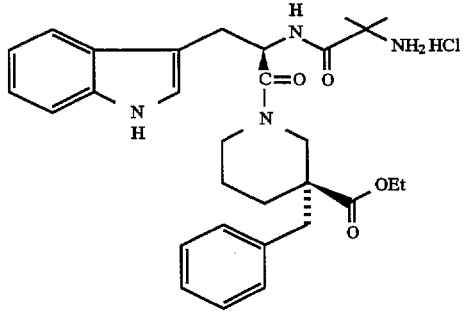

Step A:

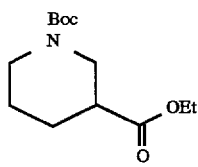

To a stirred solution of ethyl nipecotate (15 g, 95.4 mmol) and DMAP (0.05 eq.) in dichloromethane at 0° C. was added dropwise by an addition funnel di-tert-butyl dicarbonate (21.8 g, 100 mmol) in dichloromethane (200 mL). The mixture was stirred for 2–3 hours. The solution was washed with 3N HCl and saturated sodium chloride, dried over anhydrous magnesium sulfate; then filtered and concentrated to give the desired product (18.7 g, 88%).

Step B:

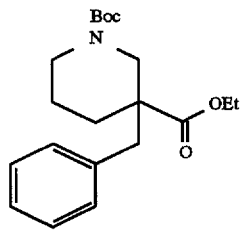

To a stirred solution of ethyl N-t-Boc nipecotate (7 g, 26.90 mmol) in THF (100 mL) at −78° C. under argon was added LHMDS (28 mL, 28 mmol) over a 10 minute period. The solution was allowed to stir an additional 30 minutes at −78° C.; then benzyl bromide (4.8 g, 28 mmol) was added slowly to the solution. The reaction mixture was stirred overnight and allowed to warm to room temperature. The material was concentrated, then diluted with water, and extracted using ethyl acetate (2×200 mL). The organic layer was dried over anhydrous magnesium sulfate, filtered, and concentrated. Purification by silica gel flash column chromatography, eluting with 20% ethyl acetate in hexane, provided the title compound. (8.32 g, 88%).

FAB-MS calc. for $C_{20}H_{29}NO_4$: 347; Found 348 (M+H)

Step C:

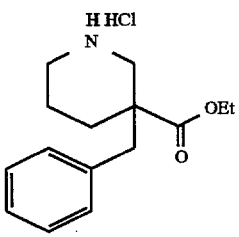

A solution of the intermediate from Step B (8 g, 23.02 mmol) in ethyl acetate (80 mL) was cooled to 0° C. While stirring, hydrogen chloride gas was bubbled into the mixture until saturation occurred. The reaction was stirred for 40 minutes, until TLC analysis indicated that the reaction was complete. The solution was then concentrated to remove the ethyl acetate to afford the product (6.53 g, 99%).

$^1$H NMR (CDCl₃, 400 MHz) δ 7.25–7.19 (m, 3H), 7.04–7.01 (m, 2H), 5.35 (v. br. s, 2H), 4.22–4.10 (m, 2H), 3.44 (d, J=13 Hz, 1H), 3.21 (br. d, J=12.7 Hz, 1H), 2.95 (d,

J=13.5 Hz, 1H), 2.76–2.68 (m, 3H), 2.22 (br. d, J=13 Hz, 1H), 1.73–1.71 (m, 1H), 1.61–1.48 (m, 2H), 1.18 (t, J=7 Hz, 3H).

FAB-MS calc. for $C_{15}H_{21}NO_2$: 247; Found 248 (M+H)

Step D:

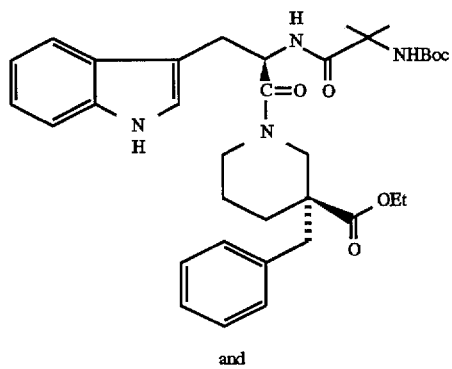

and

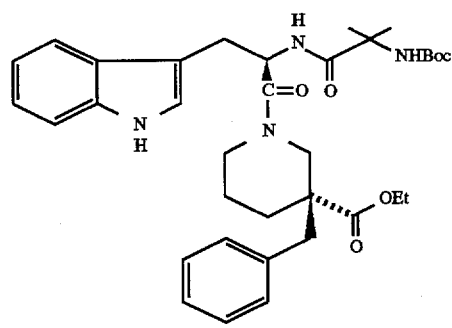

To a solution of the intermediate prepared in the previous step (1.2 g, 4.23 mmol), and Intermedate 1 (1 eq.), HOBT (1 eq.), and N-methyl morpholine (1 eq.) in dichloromethane cooled to 0° C. was added EDC (1.5 eq.). The reaction mixture was stirred at 0° C. overnight. The solution was washed with saturated sodium chloride, dried over anhydrous magnesium sulfate; then filtered and concentrated. Purification by MPLC eluting with 40% ethyl acetate in hexane provided two enantiomerically pure compounds. The compound which came out first from the column was designated as d1 (1.14 g), which has an R-absolute stereochemistry at the 3-position of the nipecotate; and the compound which came out of the column second was designated as d2 (1.08 g), which has an S-absolute stereochemistry (see Example 2 for assignment) at the 3-position of the nipecotate.

d1 FAB-MS calc. for $C_{35}H_{46}N_4O_6$: 618; Found 619 (M+H) d2 FAB-MS calc. for $C_{35}H_{46}N_4O_6$: 618; Found 619 (M+H)

Step E:

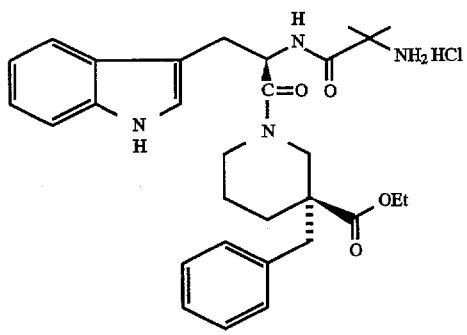

Prepared by the procedure described in Step C from the intermediates d1 from the previous step (1 g) in ethyl acetate (20 mL) and HCl gas at 0° C. for 1.5 hours. Product: 860 mg, 91%.

FAB-MS calc. for $C_{30}H_{38}N_4O_4$: 518; Found 519 (M+H)

EXAMPLE 1A

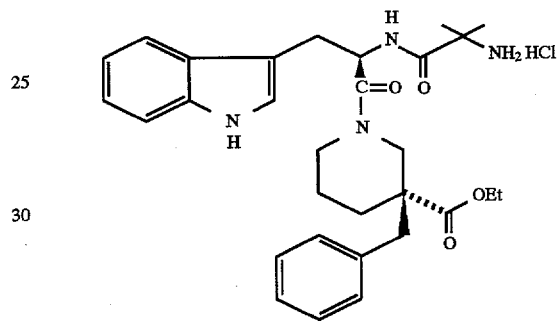

Prepared by the procedure described in Step C of Example 1 from 1 g of the d2 intermediates from the Step D of Example 1 in ethyl acetate (20 mL) by bubbling HCl at 0° C. until saturated and then evaporated after 30 minutes to give the title compound (878 mg, 93%).

FAB-MS calc. for $C_{30}H_{38}N_4O_4$: 518; Found 519 (M+H)
$^1$H NMR (CD$_3$OD, 400 MHz) compound exists in two rotamers in approximately a 5/3 ratio that slowly interconvert relative to the NMR time scale 15 7.60 (d, J=7.9 Hz, 5/8H), 7.55 (d, J=7.9 Hz, 3/8H), 7.34–6.93 (m, 9H), 5.36 (dd, J=5.2 Hz, 9.7 Hz, 3/8H), 5.31 (dd, J=6.7 Hz, 8.8 Hz, 5/8H), 4.23 (br. d, J=13.7 Hz, 3/8H), 4.10–4.00 (m, 6/8H), 4.04–3.98 (m, 3/8H), 3.96–3.82 (m, 10/8H), 3.80 (br. d, J=13.5 Hz, 5/8H), 3.36 (br. d, J=13.3 Hz, 5/8H), 3.29–3.22, 3.17–3.10, (2m, 2H), 3.20 (br. d, J=14.5 Hz, 3/8H), 3.10–2.96 (m, 5/8H), 2.90 (s, 6/8H), 2.60 (d, J=13.4 Hz, 5/8), 2.41 (d, J=13.4 Hz, 5/8H), 2.19–2.12, 1.82–1.70, 1.68–1.60, 1.50–1.40, 1.34–1.25, 1.05–0.95 (6m, 4H),1.55 (s, 9/8H), 1.50 (s, 15/8H), 1.09 (t, J=7.1 Hz, 3H).

The additional intermediates shown in Table I were prepared according to the above established procedures as exemplified in Example 1 steps A through C. The final compounds were prepared according to Example 1 Steps D and E, and Example Ia using Intermediate 1.

TABLE I

ADDITIONAL EXAMPLES

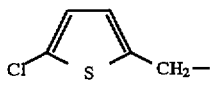

| entry | Y | Intermediate MF FAB-MS(M + 1) | Product MF FAB-MS(M + 1) | isomer[a] |
|---|---|---|---|---|
| 1 | Me | $C_9H_{17}NO_2$ 171($M^+$,EI-MS) | $C_{24}H_{34}N_4O_4$ 443 | d1 d2 |
| 2 | Et | $C_{10}H_{19}NO_2$ 185($M^+$,EI-MS) | $C_{25}H_{36}N_4O_4$ 457 | d1 d2 |
| 3 | n-Pr | $C_{11}H_{21}NO_2$ 199($M^+$,EI-MS) | $C_{26}H_{38}N_4O_4$ 471 | d1 d2 |
| 4 | allyl | $C_{11}H_{19}NO_2$ 198 | $C_{26}H_{36}N_4O_4$ 469 | d1 d2 |
| 5 | n-Bu | $C_{12}H_{23}NO_2$ 213($M^+$,EI-MS) | $C_{27}H_{40}N_4O_4$ 485 | d1 d2 |
| 6 | —CH2OEt | $C_{11}H_{21}NO_3$ 216 | $C_{26}H_{38}N_4O_5$ 487 | RS |
| 7 | cyclohexane-methyl | $C_{15}H_{27}NO_2$ 254 | $C_{30}H_{44}N_4O_4$ 525 | d1 d2 |
| 8 | $Ph(CH_2)_2$— | $C_{16}H_{23}NO2$ 261($M^+$,EI-MS) | $C_{31}H_{40}N_4O_4$ 533 | d1 d2 |
| 9 | $Ph(CH_2)_3$— | $C_{17}H_{25}NO_2$ 275($M^+$,EI-MS) | $C_{32}H_{42}N_4O_4$ 547 | d1 d2 |
| 10 | o-MeOBn— | $C_{16}H_{23}NO_3$ 278 | $C_{31}H_{40}N_4O_5$ 549 | d1 d2 |
| 11 | m-MeOBn— | $C_{16}H_{23}NO_3$ 278 | $C_{31}H_{40}N_4O_5$ 549 | d1 d2 |
| 12 | p-MeOBn— | $C_{16}H_{23}NO_3$ 278 | $C_{31}H_{40}N_4O_5$ 549 | d1 d2 |
| 13 | o-Me—Bn— | $C_{16}H_{23}NO_2$ 262 | $C_{31}H_{40}N_4O_4$ 533 | d1 d2 |
| 14 | m-Me—Bn— | $C_{16}H_{23}NO_2$ 262 | $C_{31}H_{40}N_4O_4$ 533 | d1 d2 |
| 15 | p-Me—Bn— | $C_{16}H_{23}NO_2$ 262 | $C_{31}H_{40}N_4O_4$ 533 | d1 d2 |
| 16 | o-Cl—Bn— | $C_{15}H_{20}NO_2Cl$ 282,284(3:1) | $C_{30}H_{37}N_4O_4Cl$ 554,556(3:1) | d1 d2 |
| 17 | m-Cl—Bn— | $C_{15}H_{20}NO_2Cl$ 282,284(3:1) | $C_{30}H_{37}N_4O_4Cl$ 554,556(3:1) | d1 d2 |
| 15 | p-Cl—Bn— | $C_{15}H_{20}NO_2Cl$ 282,284(3:1) | $C_{30}H_{37}N_4O_4Cl$ 554,556(3:1) | d1 d2 |
| 16 | 2,6-di-Cl—Bn— | $C_{15}H_{19}NO_2Cl_2$ 316,318,320 | $C_{30}H_{36}N_4O_4Cl_2$ 587,589,591 | |
| 17 | p-Br—Bn— | $C_{15}H_{20}NO_2Br$ 326,328(1:1) | $C_{30}H_{37}N_4O_4Br$ 597,599(1:1) | d1 d2 |
| 18 | m-Br—Bn— | $C_{15}H_{20}NO_2Br$ 326,328(1:1) | $C_{30}H_{37}N_4O_4Br$ 597,599(1:1) | d1 d2 |
| 19 | o-nitro-Bn— | $C_{15}H_{20}N_2O_4$ 293 | $C_{30}H_{37}N_5O_6$ 564 | d1 d2 |
| 20 | m-nitro-Bn— | $C_{15}H_{20}N_2O_4$ 293 | $C_{30}H_{37}N_5O_6$ 564 | d1 d2 |
| 21 | p-nitro-Bn— | $C_{15}H_{20}N_2O_4$ 293 | $C_{30}H_{37}N_5O_6$ 564 | d1 d2 |
| 22 | 1-naphthylmethyl | $C_{19}H_{23}NO_2$ 298 | $C_{34}H_{40}N_4O_4$ 569 | d1 d2 |
| 23 | (chlorothiophene-CH2—) | $C_{13}H_{18}NO_2SCl$ 288,290(3:1) | $C_{28}H_{35}N_4O_4SCl$ 559,561(3:1) | d1 d2 |
| 24 | $BnO_2C$— | $C_{16}H_{21}NO_4$ 292 | $C_{31}H_{38}N_4O_6$ 563 | RS |
| 25 | $EtO_2C$— | $C_{11}H_{19}NO_4$ 230 | $C_{26}H_{36}N_4O_6$ 501 | RS |
| 26 | p-Ph—Bn— | $C_{21}H_{25}NO_4$ | $C_{36}H_{42}N_4O_4$ | d1 |

TABLE I-continued

ADDITIONAL EXAMPLES

| entry | Y | Intermediate MF FAB-MS(M + 1) | Product MF FAB-MS(M + 1) | isomer[a] |
|---|---|---|---|---|
| | | 324 | 595 | d2 |
| 27 | (methylenedioxy-chloro-benzyl, CH₂—) | $C_{16}H_{20}NO_4Cl$ 326,328(3:1) | $C_{31}H_{37}N_4O_6Cl$ 597,599(3:1) | d1 d2 |
| 28 | (phthalimidomethyl, N—CH₂—) | $C_{17}H_{20}N_2O_4$ 317 | $C_{32}H_{37}N_5O_6$ 588 | d1 d2 |

[a] In this and in subsequent tables for isomer designation: R or S means the stereochemistry at the carbon atom to which X and Y are attached, RS means it is a mixture of the two isomers at this center; d1 or d2 means the two diastereomers were separated and are as defined in Example 1 step D.

The additional examples shown in Table Ia were prepared according to Example 1 Steps D and E, using Intermediate 1 and commercially available intermediates.

TABLE Ia

ADDITIONAL EXAMPLES

| entry | X | Product MF FAB-MS(M + 1) | isomer |
|---|---|---|---|
| 1 | —OH | $C_{20}H_{28}N_4O_3$ 373 | RS |
| 2 | —CH2OH | $C_{21}H_{30}N_4O_3$ 387 | RS |
| 3 | —CO2Et | $C_{23}H_{32}N_4O_4$ 429 | RS |
| 4 | CO2Bn | $C_{28}H_{34}N_4O_4$ 491 | RS |
| 5 | CONMe2 | $C_{23}H_{33}N_5O_3$ 428 | RS |

The additional Products shown in Table Ib were prepared according to Example 1 Steps D and E, using Intermediate 3 and some of the intermediates shown in Table 1.

TABLE Ib

ADDITIONAL EXAMPLES

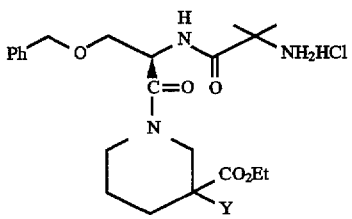

| entry | Y | Product MF FAB-MS(M + 1) | isomer |
|---|---|---|---|
| 1 | Bn | C30H41N3O4 508 | R |
| 2 | Bn | C30H41N3O4 508 | S |
| 3 | Ph(CH₂)₂ | C31H43N3O4 522 | d1 d2 |
| 4 | Ph(CH₂)₃ | C32H45N3O4 536 | d1 d2 |
| 5 | 1-naphthylmethyl | C34H43N3O4 558 | RS |
| 6 | ![thiophene-Cl] | C28H38N3O4SCl 548,550(3:1) | RS |
| 7 | p-Ph—Bn— | C36H45N3O4 584 | RS |
| 8 | BnO₂C— | C31H41N3O6 552 | RS |
| 9 | ![methylenedioxy-Cl-benzyl] | C31H40N3O6Cl 586,588(3:1) | d1 d2 |

The additional products shown in Table Ic were prepared according to Example 1 Steps D and E, using Intermediate 2 and some of the intermediates shown in Table I.

TABLE Ic

ADDITIONAL EXAMPLES

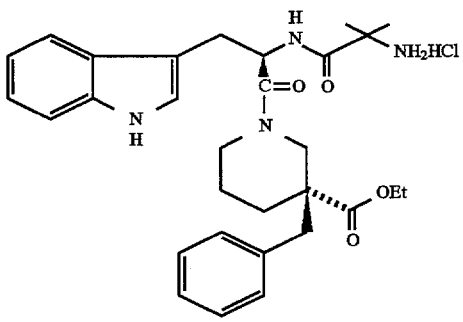

| entry | Y | MF FAB-MS(M + 1) | isomer |
|---|---|---|---|
| 1 | Bn | C29H39N3O5 510 | R |
| 2 | Bn | C29H39N3O5 510 | S |
| 3 | Et | C24H37N3O5 448 | RS |

TABLE Ic-continued

ADDITIONAL EXAMPLES

| entry | Y | MF FAB-MS(M + 1) | isomer |
|---|---|---|---|
| 4 | Ph(CH₂)₂ | C30H41N3O5 524 | d1 d2 |
| 5 | Ph(CH₂)₃ | C31H43N3O5 538 | d1 d2 |
| 6 | H | C22H33N3O5 420 | RS |

EXAMPLE 2

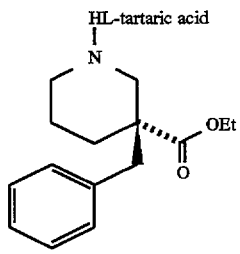

Step A:

The intermediate from Example 1, Step C (50.8 g) was dissolved in dichloromethane and it was washed with 3N NaOH. The aqueous layer was extracted with dichloromethane and the combined solution was dried (MgSO₄) and evaporated to give the free amine as an oil. The ethyl 3-benzyl nipecotate and D-tartaric acid (31 g) were dissolved in 880 mL of water/acetone (1:4) solution with heating. The solution was left in the refrigerator overnight and the crystals which were formed were filtered off. Recrystallization in 470 mL of water/acetone (1:4) at room temperature gave the ethyl 3-(R)-benzyl nipecotate D-tartaric acid salt (21 g).

The structure of this compound was determined by X-Ray crystallographic analysis. With the configuration of D-tartaric acid known to be S,S, the configuration of the chiral site in this ethyl 3-benzylnipecotate salt was determined to be R.

The combined mother liquor was evaporated and to it was added 3N NaOH and dichloromethane, the mixture was stirred for 30 minutes and the organic layer was separated. The aqueous was extracted twice with dichloromethane and the combined organic extracts were dried over MgSO₄ and evaporated to give 24.4 g of the S-isomer enriched compound. It was crystallized with L-tartaric acid (14.8 g) in 400 mL of water/acetone (1:4) at room temperature to give ethyl 3 (S)-benzyl nipecotate L-tartaric acid salt (27.3 g).

¹H NMR (CD₃OD, 400 MHz) δ 7.31–7.22 (m, 3H), 7.12–7.09 (m, 2H), 4.40 (s, 2 H, from tartaric acid), 4.30–4.10 (m, 2H), 3.49 (br. d, J=13 Hz, 1H), 3.06 (d, J=13.6 Hz, 1H), 2.98 (d, J=13 Hz, 1H), 2.92 (dt, J=3.3 Hz, 13 Hz, 1H), 2.82 (d, J=13.6 Hz, 1H), 2.30 (d, J=12.4 Hz, 1 H), 1.88 (td, J=3 Hz, 14.5 Hz, 1H), 1.69 (dt, J=3 Hz, 13 Hz, 1H), 1.63–1.51 (m, 1H), 1.25b (q, J=7.1 Hz, 3H).

Step B:

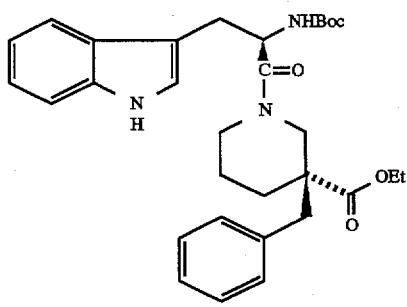

Ethyl 3(S)-benzyl nipecotate L-tartaric acid salt (39.74 g) was suspended in 70 mL of 3N NaOH and 70 mL of water, followed by extraction with dichloromethane. The extracts were combined, dried, and evaporated to give a thick oil. To a stirred solution of the oil, N-t-Boc D-TrpOH (30.43 g) and HOBt (13.5 g) in dichloromethane (200 mL) at 0° C, was added EDC (23 g) in several portions. The mixture was stirred overnight and it was poured into water and 3N HCl and was extracted with dichloromethane. The organic layer was washed with brine, saturated sodium bicarbonate, dried over MgSO₄ and evaporated to give a crude product (67.7 g), which was used without further purification.

FAB-MS calc. for $C_{31}H_{39}N_3O_5$: 533; Found 534 (M+H)

Step C:

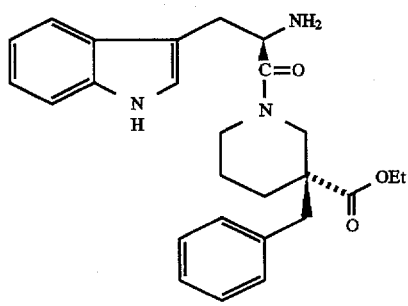

To a solution of the intermediate from the previous step (67.7 g crude) in ethyl acetate (100 mL) at 0° C., was bubbled HCl gas until it was saturated. The reaction mixture was stirred at 0° C. for 30 minutes and was evaporated to remove excess HCl and ethyl acetate. The residue was suspended in dichloromethane and was washed with a mixture of 3N NaOH (70 mL) and water (100 mL). The organic layer was dried (MgSO₄), evaporated to a small volume and used in next step without further purification.

FAB-MS calc. for $C_{26}H_{31}N_3O_3$: 433; Found 434 (M+H)

Step D:

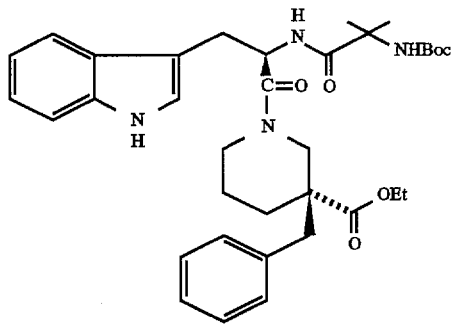

A solution containing the intermediate obtained in the last step, N-Boc-α-Me-AlaOH (20.3 g), and DMAP (200 mg) in dichloromethane (100 mL) was stirred at room temperature and to it was added EDC (24 g) in several portions. The reaction mixture was stirred for 3 hours and was worked up by diluting it with dichloromethane and washing with 3N HCl, brine, and saturated sodium bicarbonate solution. The organic layer was dried over MgSO₄, and evaporated to give a thick oil. This oil was passed through a pad of silica gel, eluting with 60% ethyl acetate in hexane to remove some very polar impurities, to give the desired compound (54.2 g)

FAB-MS calc. for $C_{35}H_{46}N_4O_6$: 618; Found 619 (M+H)

Step F:

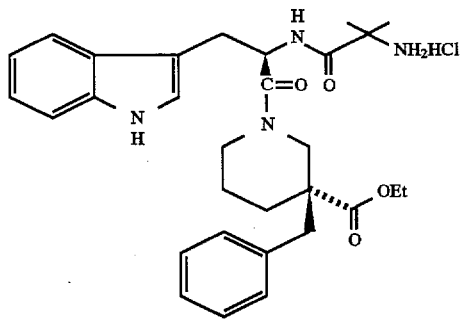

To a solution of the intermediate from the previous step (54.2 g) in ethyl acetate (100 mL) at 0° C., was bubbled HCl gas until it was saturated. The reaction mixture was stirred at 0° C. for 15 minutes and was evaporated to remove excess HCl and ethyl acetate. The residue was first dissolved in dichloromethane (100 mL) and then ethyl acetate (300 mL) was added. The mixture was stirred overnight and the solid was collected by filtration to give the title compound (34 g). Further evaporation of the mother liquor to a small volume gave the second crop of product (10.1 g).

MS and NMR identical with Example 1A.

The additional products shown in Table II were prepared according to Example 2, Steps B through F, using the readily available Boc protected amino acids instead of N-t-Boc-D-TrpOH.

TABLE II

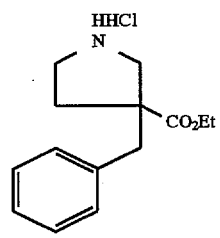

| entry | R | Product MF FAB-MS(M + 1) |
|---|---|---|
| 1 | 4-F | C30H37N4O4F 537 |
| 2 | 5-F | C30H37N4O4F 537 |
| 3 | 6-F | C30H37N4O4F 537 |
| 4 | 1-Me | C31H40N4O4 533 |
| 5 | 5-MeO | C31H40N4O5 549 |
| 6 | 5-HO | C30H38N4O5 535 |
| 7 | 6-MeO | C31H40N4O5 549 |

EXAMPLE 3

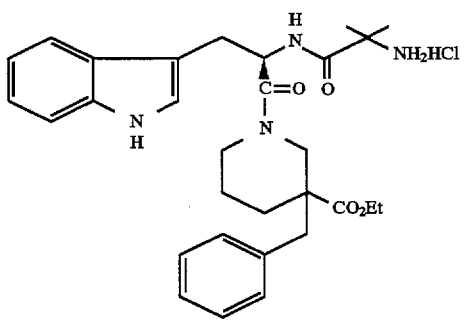

Step A:

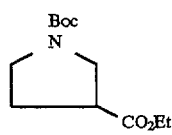

To a stirred solution of ethyl 3-pyrrolidinecarboxylate hydrochloride (J. Chem. Soc., 24, 1618–1619; 10 g, 69.8 mmol), triethylamine (7.75 mL) and DMAP (857 mg) in dichloromethane (40 mL), was slowly added di-t-butyl dicarboxylate (18.3 g, 83.7 mmol) and the resulting mixture was stirred at room temperature for three days. The mixture was then concentrated, washed with 3N HCl and dried and evaporated to give the intermediate.

Step B:

Prepared by the procedure described in Example 1, Step B from the intermediate obtained from previous step (500 mg, 2.05 mmol), KHMDS (512 mg, 2.57 mmol) and benzyl bromide (371 mg, 2.16 mmol). Purification by silica gel flash column eluting with 5–20% ethyl acetate in hexane provided the title compound (385 mg, 56%).

Step C:

Prepared by the procedure described in Example 1, Step C from the intermediate from the previous step (385 mg, 1.16 mmol) in ethyl acetate (5 mL) and HCl gas at 0° C. for 15 minutes (306 mg, 98%).

Step D:

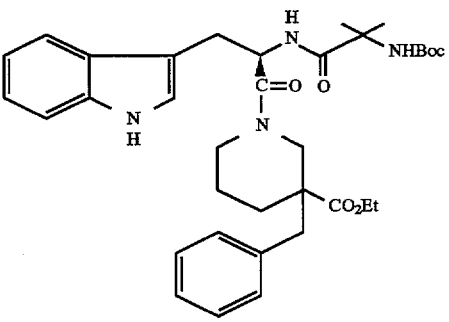

Prepared by the procedure described in Example 1, Step D from the intermediate prepared in the previous step (138 mg, 0.514 mmol), intermediate 1 (200 mg, 0.514 mmol), HOBT (1 eq.), N-methyl morpholine (1 eq.), and EDC (2 eq.). Purification by MPLC, eluting with ethyl acetate in hexane gave the product (250 mg, 80%)

FAB-MS calc. for $C_{34}H_{44}N_4O_6$: 604; Found 605 (M+H).

Step E:

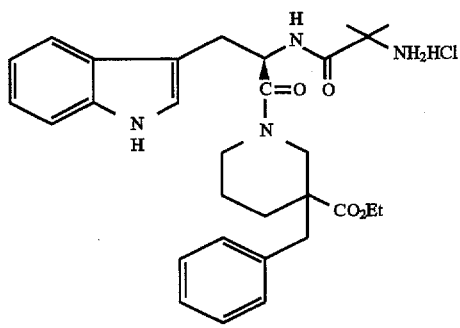

Prepared by the procedure described in Example 1, Step C from the intermediate from the previous step (250 mg, 0.036 mmol) in ethyl acetate (3 mL) and HCl gas at 0° C. for 10 minutes.

FAB-MS calc. for $C_{29}H_{36}N_4O_4$: 504; Found 505 (M+H).

EXAMPLE 4

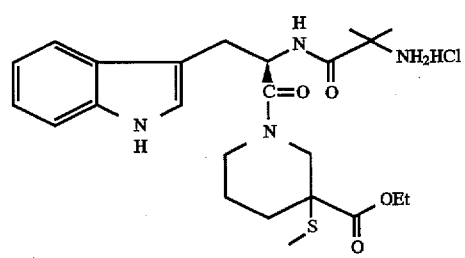

Step A:

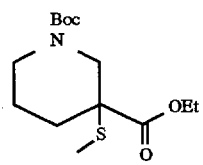

To a stirred solution of ethyl N-t-Boc nipecotate (4 g, 15.7 mmol)) in TI-IF (100 mL) at –78° C. under argon was added LHMDS (1M, mL, 32 mmol) over a 10 minute period. The solution was allowed to stir an additional 30 minutes at –78° C.; then methyl disulfide (1.92 g, 20.37 mmol) was added slowly to the solution. The reaction mixture was stirred overnight and allowed to warm to room temperature. The material was concentrated, then diluted with water, and extracted using ethyl acetate (2×200 mL). The organic layer was dried over anhydrous magnesium surf ate, filtered, and concentrated. Purification by silica gel flash column chromatography eluting with 20% ethyl acetate in hexane provided the title compound.

FAB-MS calc. for $C_{14}H_{25}NO_4S$: 271; Found 272 (M+H)

Step B:

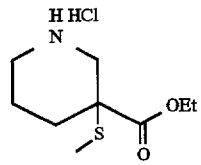

Prepared by the procedure described in Example 1, Step C from the intermediate from the previous step (1 g, 3.3 mmol) in ethyl acetate (25 mL) and HCl gas at 0° C. for 35 minutes to yield the product (783 mg, 99%).

FAB-MS calc. for $C_9H_{17}NO_2S$: 171; Found 271 (M+H)

Step C:

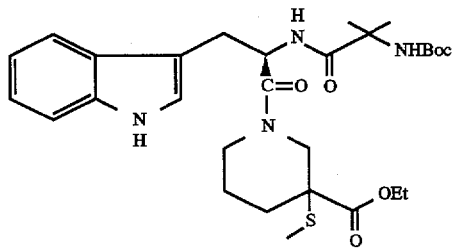

Prepared by the procedure described in Example 1, Step D from the intermediate prepared in the previous step (123 mg, 0.514 mmol), Intermediate 1 (1 eq.), HOBT (1 eq.), NMM (1 eq.), and EDC (197 mg, 1.028 mmol). Purification by MPLC provided diastereomers. The compound which came out first from the column was designated as d1 (109 mg, 37%); and the compound which came out of the column second was designated as d2 (88 mg, 30%), d1 FAB-MS calc. for $C_{29}H_{42}N_4O_6S$: 574; Found 575 (M+H) d2 FAB-MS calc. for $C_{29}H_{42}N_4O_6S$: 574; Found 575 (M+H)

Step D:

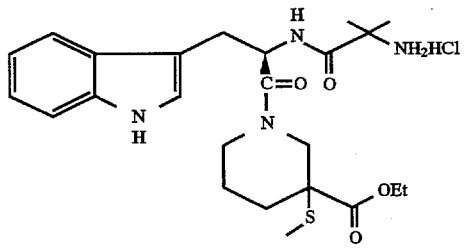

Prepared by the procedure described in Example 1, Step C from the intermediates d 1(80 mg) and d2 (80 mg) separately from the previous step in ethyl acetate (5 mL each) and HCl gas at 0° C. for 20 minutes.

d1: (71 mg, 99%)
d2: (70 mg, 98%)

d1 $^1$H NMR (CD$_3$OD, 400 MHz): The compound exists in two rotamers in approximately a 1:1 ratio. δ 7.71 (d, J=7.2 Hz, 1/2H), 7.56 (d, J=7.2 Hz, 1/2H), 7.38 (d, J=8.0 Hz, 1/2H), 7.33 (d, J=7.5 Hz, 1/2H), 7.14–7.01 (m, 3H), 5.44 (dd, J=6 Hz, 8 Hz, 1/2H), 4.30–4.10 (m, 5/2H), 3.92 (d, J=13.3 Hz, 1/2H), 3.81 (d, J=13.3 Hz, 1/2H), 3.67 (d, J=13.3 Hz, 1/2H), 3.48–3.40 (m, 1/2H), 3.28–3.09 (m, 7/2H), 2.55 (dt, 1/2H), 2.26–2.20 (br. d, 1/2H), 2.05 (s, 3H), 1.80–1.70 (m, 1/2H), 1.67, 1.59, 1.55, 1.43 (4s, 6H), 1.27 (t, J=7.0 Hz, 3/2H), 1.19 (t, J=7.0 Hz, 3/2H), 0.90–0.85 (m, 1/2H).

d2 $^1$H NMR (CD$_3$OD, 400 MHz): The compound exists in two rotamers in approximately a 1:1 ratio. δ 7.77 (d, J=7.5

Hz, 1/2H), 7.56 (d, J=7.9 Hz, 1/2H), 7.35–7.30 (m, 1H), 7.13–6.98 (m, 3H), 5.53 (rid, J=5.5 Hz, 8 Hz, 1/2H), 5.24 (app. t, J=7 Hz, 1/2H), 4.30 (br. d, J=14 Hz, 1/2H), 4.20–4.10 (m, 2H), 3.90–3.85 (m, 1/2H), 3.86 (d, J=13.2 Hz, 1/2H), 3.70 (d, J=13.7 Hz, 1/2H), 3.35–3.10 (m, 4H), 2.30–2.20 (m, 1/2H), 2.12, 2.04 (2s, 3H), 2.04–2.00 (m, 1/2H), 1.80–1.70 (m, 3/2H), 1.54, 1.50, 1.43, 1.26 (4s, 6H), 1.23 (t, J=6.7 Hz, 3H), 0.90–0.84 (m, 1/2H).

d1 FAB-MS calc. for $C_{24}H_{34}N_4O_4S$: 474; Found 475 (M+H)

d2 FAB-MS calc. for $C_{24}H_{34}N_4O_4S$: 474; Found 475 (M+H)

The additional intermediates shown in Table III were prepared according to the above established procedure as exemplified in Example 4 steps A and B. The final compounds were prepared according to Example 4 Steps C and D, using Intermediate 1.

TABLE III

| entry | Intermediate Y | Intermediate MF FAB-MS(M + 1) | Product MF FAB-MS(M + 1) | Product isomer |
|---|---|---|---|---|
| 1 | PhS— | $C_{14}H_{19}NO_2S$ 266 | $C_{29}H_{36}N_4O_4S$ 537 | d1 d2 |
| 2 | BnS— | $C_{15}H_{21}NO_2S$ 280 | $C_{30}H_{38}N_4O_4S$ 551 | d1 d2 |
| 3 | 2-pyridylthio- | $C_{13}H_{18}N_2O_2S$ 267 | $C_{28}H_{35}N_5O_4S$ 538 | RS |
| 4 | (N,CH3 thiazolyl-S—) | | $C_{27}H_{35}N_5O_4S2$ 558 | RS |

EXAMPLE 5

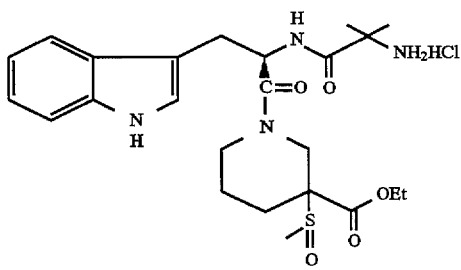

Step A:

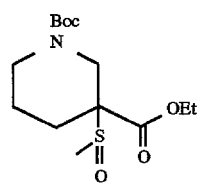

To a stirred solution of $NaIO_4$ (316.5 mg, 1.48 mmol) in water (5 mL) and ethanol (5 mL) was added the intermediate from Example 4, Step A (300 mg, 0.99 mmol). The mixture was stirred for 5 hours at room temperature, then concentrated to remove ethanol. The material was then extracted with ethyl acetate (2×10 mL). The organic layer was dried over magnesium sulfate and concentrated to give the title compound (286 mg, 90.5%).

FAB-MS calc. for $C_{14}H_{25}NO_5S$: 319; Found 320 (M+H)

Step B:

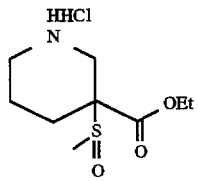

Prepared by the procedure described in Example 1, Step C from the intermediate from the previous step (230 g, 0.72 mmol) in ethyl acetate (10 mL) and HCl gas at 0° C. for 25 minutes (197 mg, 100%).

FAB-MS calc. for $C_9H_{17}NO_3S$: 219; Found 220 (M+H)

Step C:

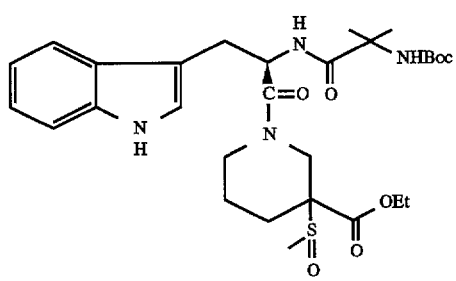

Prepared by the procedure described in Example 1, Step D from the intermediate prepared in the previous step (140 mg, 0.547 mmol), Intermediate 1 (1 eq.), HOBT (1 eq.), N-methyl morpholine (1 eq.), and EDC (210 mg, 1,094 mmol). Purification by MPLC provided a diastereomeric mixture of compounds (177 mg, 55%).

FAB-MS calc. for $C_{29}H_{42}N_4O_7S$: 590; Found 591 (M+H)

Step D:

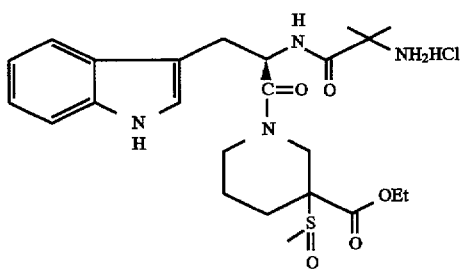

Prepared by the procedure described in Example 1, Step C from the intermediate from the previous step (150 mg, 0.254 mmol) in ethyl acetate (10 mL) and HCl gas at 0° C. for 20 minutes (118 mg, 90%).

FAB-MS calc. for $C_{24}H_{34}N_4O_5S$: 490; Found 491 (M+H)

EXAMPLE 6

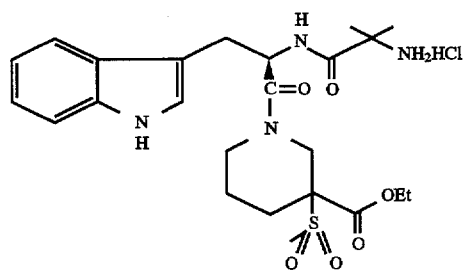

Step A:

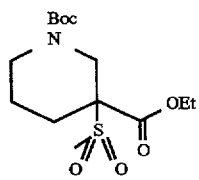

To a stirred solution of Oxone (910 mg, 1.48 mmol) in water (5 mL) and methanol (5 mL) was added the intermediate from Example 4, Step A (300 mg, 0.99 mmol). The mixture was stirred for 4 hours at room temperature, then concentrated to remove methanol. The residue was then extracted with ethyl acetate (2×10 mL). The organic layer was dried over magnesium surfate and concentrated to give the title compound (321 mg, 97%).

FAB-MS calc. for $C_{14}H_{25}NO_6S$: 335; Found 336 (M+H) [Found 236 (M-t-Boc)]

Step B:

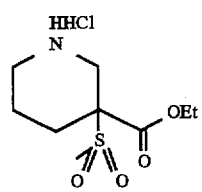

Prepared by the procedure described in Example 1, Step C from the intermediate from the previous step (221 mg, 0.66 mmol) in ethyl acetate (10 mL) and HCl gas at 0° C. for 25 minutes (192 mg, 99%).

FAB-MS calc. for $C_9H_{17}NO_4S$: 235; Found 236 (M+H)

Step C:

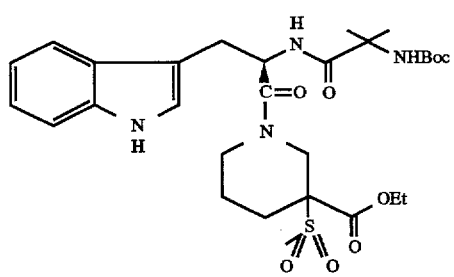

Prepared by the procedure described in Example 1, Step D from the intermediate prepared in the previous step (140 mg, 0.515 mmol), Intermediate 1 (1 eq.), HOBT (1 eq.), N-methyl morpholine (1 eq.), and EDC (197 mg, 1.03 mmol.). Purification by MPLC provided a diastereomeric mixture of compounds (251 mg, 80%).

FAB-MS calc. for $C_{29}H_{42}N_4O_8S$: 606; Found 607 (M+H)

Step D:

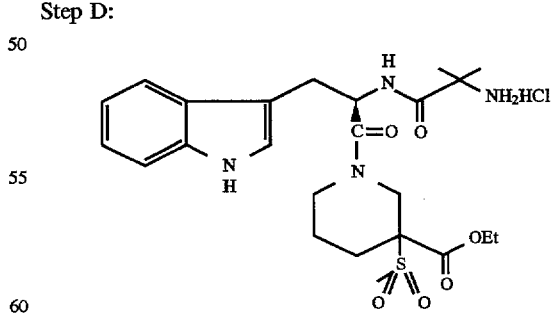

Prepared by the procedure described in Example 1, Step C from the intermediate from the previous step (210 mg, 0.317 mmol) in ethyl acetate (10 mL) and HCl gas at 0° C. for 30 minutes (193 mg, 98.5%) FAB-MS calc. for $C_{24}H_{34}N_4O_6S$: 506; Found 507 (M+H)

EXAMPLE 7

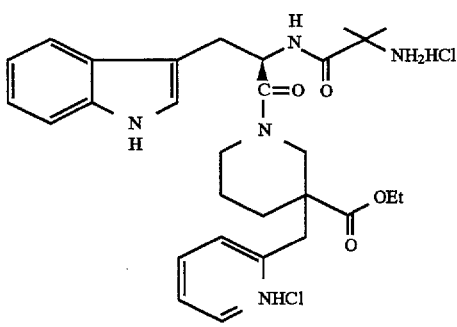

Step A:

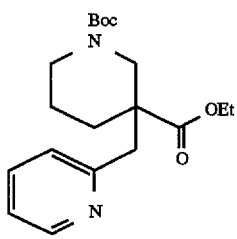

To a stirred solution of ethyl N-t-Boc nipecotate (50 g, 0.196 mol) in THF (600 mL) at −78° C. under argon was added KHMDS (0.5M in toluene, 298 mL, 0.298 mol) over a 30 minute period. The solution was allowed to stir an additional 30 minutes at −78° C. Meanwhile, a suspension of 2-picolyl chloride hydrochloride (25 g) in dichloromethane was washed with a mixture of 3N NaOH and brine to remove the hydrochloride. The organic layer was dried over MgSO$_4$ and evaporated to yield a brown oil and it was added slowly to the solution at −78° C. The reaction mixture was stirred overnight and allowed to warm to room temperature. The material was concentrated, then diluted with water, and extracted using ethyl acetate. The organic layer was dried over anhydrous magnesium sulfate, filtered, and concentrated. Purification by silica gel flash column chromatography eluting with a solvent gradient of 20–80% ethyl acetate in hexane provided the title compound. (54.8 g, 80%). $^1$H NMR (CD$_3$OD, 400 MHz) δ 8.45 (dd, J=1.5 Hz, 5 Hz, 1H), 7.52 (app dt, J=2 Hz, 8 Hz, 1H), 7.07 (dd, J=5 Hz, 6.6 Hz, 1H), 7.05 (d, J=8 Hz, 1H), 4.09–4.04 (br. m, 2H), 3.92 (br. d, 1H), 3.46 (br. m, 1H), 3.30–3.10 (br. m, 1H), 3.06 (d, J=13.7 Hz, 1H), 2.95 (d, J=13.7 Hz, 1H), 2.01–1.91 (br. m, 1H), 1.63–1.50 (br. m, 3H), 1.36 (v. br. s, 9H), 1.13 (t, 7.1 Hz, 3H). FAB-MS calc. for C$_{19}$H$_{28}$N$_2$O$_4$: 348; Found 349 (M+H)

Step B:

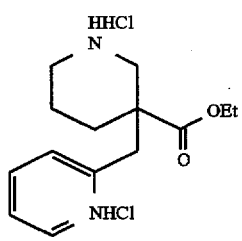

Prepared by the procedure described in Example 1, Step C from the intermediate from the previous step (6.36 g, 18.2 mmol) in ethyl acetate (100 mL) and HCl at 0° C. for 45 minutes (6.10 g, 100%.) FAB-MS calc. for C$_{14}$H$_{20}$N$_2$O$_2$: 248; Found 249 (M+H)

Step C:

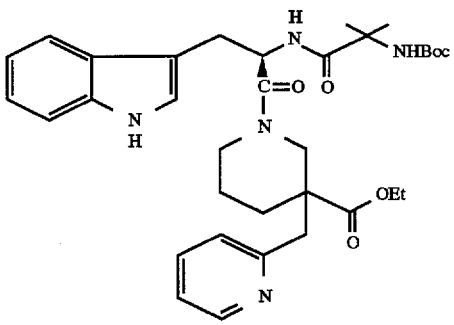

Prepared by the procedure described in Example 1, Step D from the compound prepared in the previous step (500 mg, 1.556 mmol), Intermediate 1(1 eq.), HOBT (1 eq.), N-methyl morpholine (2 eq.), and EDC (597 mg, 3.11 mmol). Purification by MPLC eluting with ethyl acetate provided the title compound (883 mg, 91.5%).

FAB-MS calc. for C$_{34}$H$_{45}$N$_5$O$_6$: 619; Found 620 (M+H)

Step D:

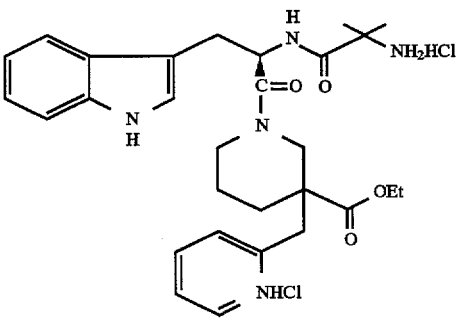

Prepared by the procedure described in Example 1, Step C from the intermediate from the previous step (250 mg, 0.404 mmol) in ethyl acetate (25 mL) and HCl gas at 0° C. for 25 minutes (204 mg, 85%) FAB-MS calc. for C$_{29}$H$_{37}$N$_5$O$_4$: 519; Found 520 (M+H)

The additional intermediates shown in Table IV were prepared according to the above established procedure as exemplified in Example 7 step A and B. The final compounds were prepared according to Example 7 Steps C and D, using Intermediate 1.

TABLE IV

[Intermediate structure: piperidine with NH, CO2Et and Y substituent on 3-position]

[Product structure: tryptophan derivative with piperidine bearing CO2Et and Y, coupled to an aminoisobutyryl group with NH2·HCl]

| entry | Y | Intermediate MF FAB-MS(M + 1) | Product MF FAB-MS(M + 1) | isomer |
|---|---|---|---|---|
| 1 | 3-picolyl | $C_{14}H_{20}N_2O_2$ 249 | $C_{29}H_{37}N_5O_4$ 520 | RS |
| 2 | 4-picolyl | $C_{14}H_{20}N_2O_2$ 249 | $C_{29}H_{37}N_5O_4$ 520 | RS |
| 3 | 2-quinoline-methyl | $C_{18}H_{22}N_2O_2$ 298 | $C_{33}H_{39}N_5O_4$ 569 | RS |
| 4 | [benzimidazol-2-ylmethyl] | $C_{16}H_{21}N_3O_2$ 288 | $C_{31}H_{38}N_6O_4$ 559 | d1 d2 |
| 5 | [N-benzyl-imidazol-2-ylmethyl] | $C_{19}H_{25}N_3O_2$ 328 | $C_{34}H_{42}N_6O_4$ 599 | RS |
| 6 | [3-methylpyridin-2-ylmethyl] | $C_{15}H_{22}N_2O_2$ 263 | $C_{30}H_{39}N_5O_4$ 534 | RS |

The additional compounds shown in Table IVa were prepared according to Example 7 Steps C and D, using some of the intermediates shown in Table IV and Intermediate 3 instead of Intermediate 1.

TABLE IVa

ADDITIONAL EXAMPLES

[Structure: Ph-(CH2)3-CH(NH-)-C(=O)-N-piperidine(CO2Et, Y); NH connected to C(CH3)2-NH2·HCl via C=O]

| entry | Y | MF FAB-MS(M + 1) | isomer |
|---|---|---|---|
| 1 | 2-picolyl | $C_{29}H_{40}N_4O_4$ 509 | d1 d2 |
| 2 | 3-picolyl | $C_{29}H_{40}N_4O_4$ 509 | d1 d2 |
| 3 | 4-picolyl | $C_{29}H_{40}N_4O_4$ 509 | d1 d2 |
| 4 | [quinolin-2-ylmethyl] | $C_{33}H_{42}N_4O_4$ 559 | RS |

TABLE IVa-continued

ADDITIONAL EXAMPLES

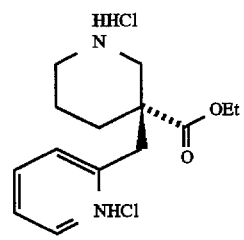

| entry | Y | MF FAB-MS(M + 1) | isomer |
|---|---|---|---|
| 5 | (benzimidazol-2-yl)-CH₂— | C31H41N5O4 548 | d1 d2 |
| 6 | (3-methylpyridin-2-yl)-CH₂— | C30H42N4O4 523, 545(M+Na) | d1 d2 |

EXAMPLE 8

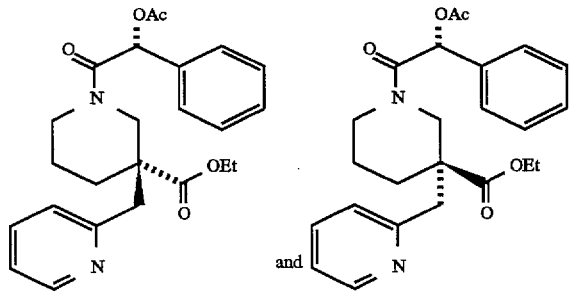

Step A:

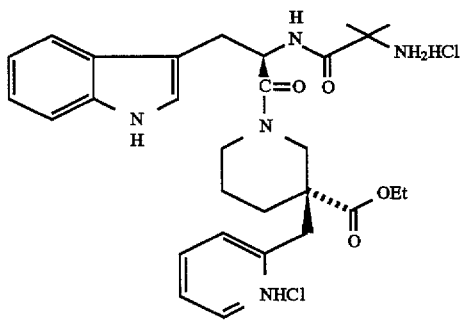

Prepared by the procedure described in Example 1, Step D from the intermediate (6 g, 18.67 mmol) prepared in Example 7, Step B, and using (R)-(−)-(O)-acetyl mandelic acid (1 eq.), HOBT (1 eq.), N-methyl morpholine (2 eq.), and EDC (7.16 g, 37.34 mmol). Purification by MPLC eluting with 80% ethyl acetate in hexane provided two enantiomerically pure compounds. The isomer which came out of the column first was designated as d1 (3.92 g, 99%) and the isomer which came out of the column second as d2 (3.69 g, 93%)

FAB-MS calc. for $C_{24}H_{28}N_2O_5$ Found 425. The structure of intermediate d1 was determined by x-ray crystallography. Given the absolute stereochemistry of (R)-O-acetylmandelic acid, the stereochemistry at the piperidine 3-position was assigned (S)- in $d_1$.

Step B:

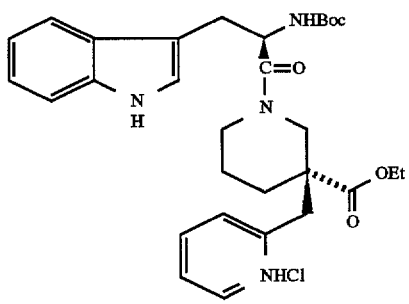

The intermediate d1 from the previous step (2.91 g, 6.86 mmol) in ethanol (30 mL) and concentrated HCl (25 mL) was refluxed for five hours. The reaction mixture was evaporated in vacuo and the residue was purified by silica gel flash column chromatography eluting with a solvent gradient of 1:10:90 to 2:20:80 ammonium hydroxide:methanol:chloroform to provide the compound (d1, 1.52 g, 70%). $^1$H NMR (CD$_3$OD, 400 MHz) δ 8.84 (app. d, J=6 Hz, 1H), 8.60 (app. dt, J=1.5 Hz, 8 Hz, 1H), 8.04 (t, J=6 Hz, 1H), 7.94 (d, J=8 Hz, 1H), 4.34–4.27 (m, 1H), 4.23–4.17 (m, 1H), 3.75 (d, J=13 Hz, 1H), 3.46 (d, J=13.3 Hz, 1H), 3.40 (d, J=13.3 Hz, 1H), 3.31–3.29 (m, 2H), 3.20 (d, J=13 Hz, 1H), 3.03 (app dt, J=3.1 Hz, 12.8 Hz, 1H), 2.24 (br. d, 1H), 2.00–1.93 (m, 1H), 1.88 (dd, J=3.7 Hz, 13.5 Hz, 1H), 1.63–1.60 (m, 1H), 1.23 (t, 7.1 Hz, 3H). FAB-MS calc. for $C_{14}H_{20}N_2O_2$: 248; Found 249 (M+H)

Step C:

Prepared by the procedure described in Example 1, Step D from the intermediate prepared in Step B of this example (d1, 1.50 g, 4.67 mmol), N-t-Boc-D-Trp (1 eq.), HOBT (1 eq.), and EDC (1.53 g, 8.00 mmol). Purification by MPLC eluting with ethyl acetate provided the title compound (1.764 g, 71%). FAB-MS calc. for $C_{30}H_{38}N_4O_5$: 534; Found 535 (M+H)

Step D:

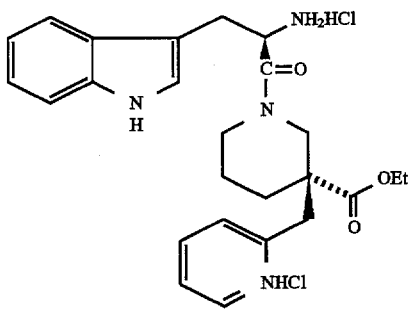

Prepared by the procedure described in Example 3, Step C from the intermediate from the previous step (1,658 g, 3.11 mmol) in ethyl acetate (50 mL) and HCl gas at 0° C. for 35 minutes (1.56 g, 99%).

FAB-MS calc. for $C_{25}H_{30}N_4O_3$: 434; Found 435 (M+H)

Step E:

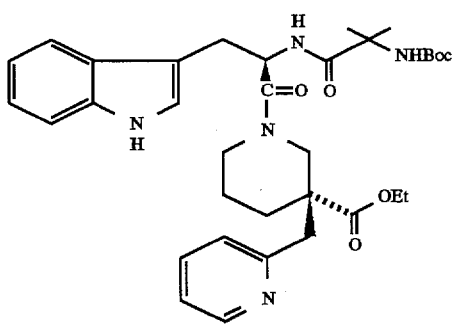

Prepared by the procedure described in Example 1, Step D from the intermediate prepared in Step D of this example (1.5 g, 2.96 mmol), N-t-Boc-α-methylalanine (1.1 eq.) DMAP (0.15 eq.), N-methyl morpholine (1 eq.), and EDC (1.135 g, 5.92 mmol). Purification by MPLC provided the title compound. (1.488 g, 81%)

FAB-MS calc. for $C_{34}H_{45}N_5O_6$: 619; Found 620 (M+H)

Step F:

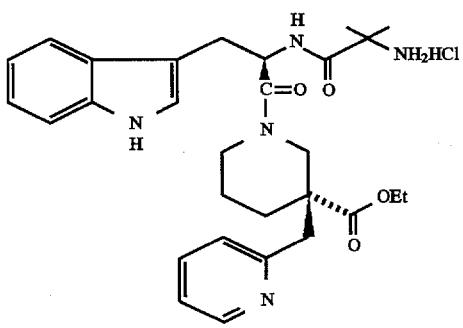

Prepared by the procedure described in Example 1, Step C from the intermediate from Step E (1.40 g, 2.26 mmol) in ethyl acetate (100 mL) and HCl gas at 0° C. for 1 hour (1.388 g, 100%). $^1$H NMR (CD$_3$OD, 400 MHz): 8.79–8.78 (M, 1H), 8.56–8.48 (M, 24), 8.0–7.96 (M, 1H), 7.72 (d, J=8.21 Hz, 1H) 7.53 (d, J=7.98, Hz, 1H) 7.25–7.22 (M, 2H) 6.89–6.86 (M, 1H) 5.48–5.43 (M, 1H) 3.89 (1, J=7.1 Hz, 2H) 2.30 (d, J=14.3 Hz, 1H) 1.85 (d, J=14.4 Hz, 1H) 1.01 (t, J=7.1 Hz, 3H) FAB-MS calc. for $C_{29}H_{37}N_5O_4$: 519; Found 520 (M+H)

EXAMPLE 9

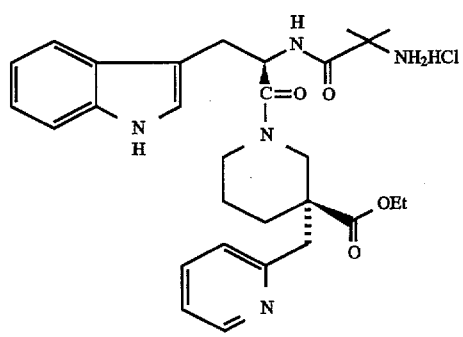

The title compound was similarly prepared from the intermediate d2 from Example 8, Step A. FAB-MS calc. for $C_{29}H_{37}N_5O_4$: 519; Found 520 (M+H)

EXAMPLE 10

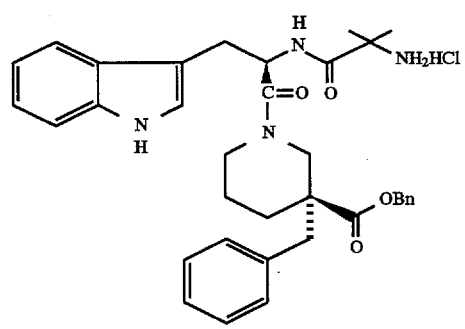

Step A:

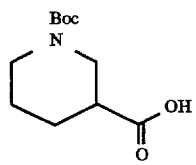

To a stirred solution of nipecotic acid (5 g, 38.7 mmol) in NaOH (2 eq.) in water was added di-tert-butyl dicarbonate (10 g, 46.44 mmol). The mixture was stirred at room temperature for 2 days. The mixture was then slowly acidified to pH=3 and stirred for two hours. The solution was extracted with ethyl acetate, dried, and concentrated to give white solid (6.25 g, 70%).

Step B:

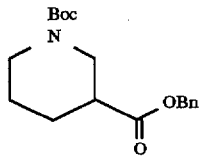

To a solution of the intermediate from the previous step (6.25 g, 27.3 mmol), benzyl alcohol (3.4 mL, 32.7 mmol) and DMAP (33 mg, 0.273 mmol) in dichloromethane at 0° C., was added EDC (6.9 g, 35.4 mmol). The reaction mixture was stirred at room temperature for 7 hours. It was washed with a mixture of brine and 3N HCl, dried over anhydrous magnesium sulfate, filtered and concentrated. Purification by silica gel flash column eluting with a gradient of 10–30% ethyl acetate in hexane provided the benzyl ester (7.41 g, 85%).

Step C:

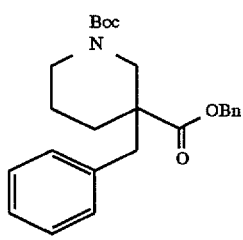

Prepared by the procedure described in Example 1, Step B from benzyl N-t-Boc-nipecotate (7.12 g, 22.2 mmol), LHMDS in THF (33.3 mL, 33.3 mmol) and benzyl bromide (4.0 g, 33.3 mmol). Purification by silica gel flash column chromatography eluting with 5–20% ethyl acetate in hexane provided the title compound. (9.10 g, 100%) $^1$H NMR (CDCl$_3$, 400 MHz) δ 7.33–7.28 (m, 3H), 7.23–7.17 (m, 5H), 7.01–6.98 (m, 2H), 5.00 (br. ABq, JAB=12 Hz, 2H), 4.00 (br. s, 1H), 3.55–3.50 (m, 1H), 3.18 (d, J=13 Hz) 3.14 (v. br. s, 1H), 2.92 (d, J=13.5 Hz), 2.74 (d, J=13.4 Hz), 2.03–1.99 (m, 1H), 1.63–1.50 (m, 3H), 1.39 (s, 9H).

Step D:

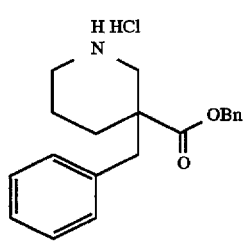

Prepared by the procedure described in Example 1, Step C from the intermediate from the previous step (3.08 g, 7.52 mmol) in ethyl acetate (40 mL) and HCl gas at 0° C. for 15 minutes (2.65 g, 100%).

FAB-MS calc. for C$_{20}$H$_{23}$NO$_2$: 309; Found 310 (M+H)

Step E:

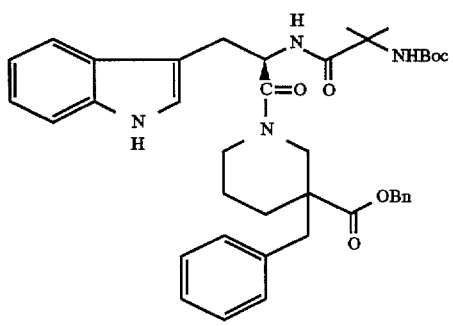

Prepared by the procedure described in Example 1, Step D from the intermediate prepared in the previous step (768 mg, 2.22 mmol), Intermediate 1 (720 mg, 1.85 mmol), HOBT (1 eq.), N-methyl morpholine (1 eq.), and EDC (2 eq.). Purification by MPLC, eluting with ethyl acetate in hexane, provided two diastereomers. The isomer which came out first was designated as d1 (504 mg, 40%) and the one which eluted second was designated as d2 (474 mg, 38%)

d1 FAB-MS calc. for C$_{40}$H$_{48}$N$_4$O$_6$: 680; Found 681 (M+H) d2 FAB-MS calc. for C$_{40}$H$_{48}$N$_4$O$_6$: 680; Found 681 (M+H)

Step F:

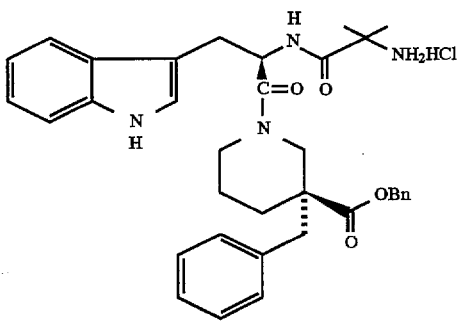

Prepared by the procedure described in Example 1, Step C from the intermediate d1 from Step E (25 mg, 0.036 mmol) in ethyl acetate (3 mL) and HCl gas at 0° C. for 10 minutes (20.2 mg, 91%).

FAB-MS calc. for C$_{35}$H$_{40}$N$_4$O$_4$: 580; Found 581 (M+H)

EXAMPLE 11

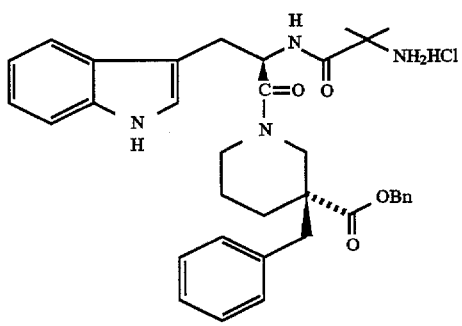

Prepared by the procedure described in Example 1, Step C from the intermediate d2 (20.1 mg, 0.03 mmol) of Example 10, Step E in ethyl acetate (3 mL) and HCl gas at 0° C. for 10 minutes (12.8 mg, 70%).

FAB-MS calc. for C$_{35}$H$_{40}$N$_4$O$_4$: 580; Found 581 (M+H)

EXAMPLE 12

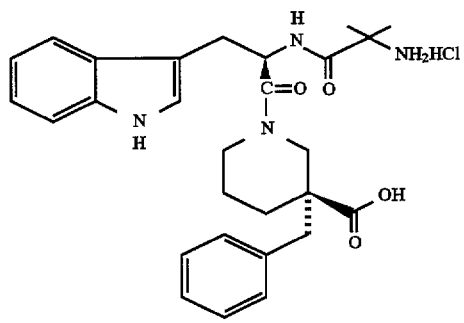

Step A:

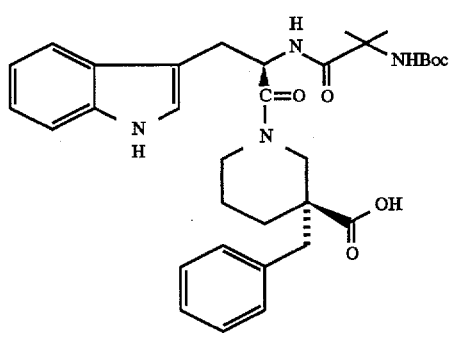

A suspension of 10% palladium on carbon (60 mg) and the intermediate (d1) from Example 10, Step E (442.6 mg, 0.65 mmol) in ethanol (20 mL) was vigorously stirred under a hydrogen atmosphere for 30 minutes. The reaction mixture was then filtered through celite and evaporated to give the product (376.0 mg, 98%).

d1 FAB-MS calc. for $C_{33}H_{42}N_4O_6$: 590; Found 591 (M+H)

Step B:

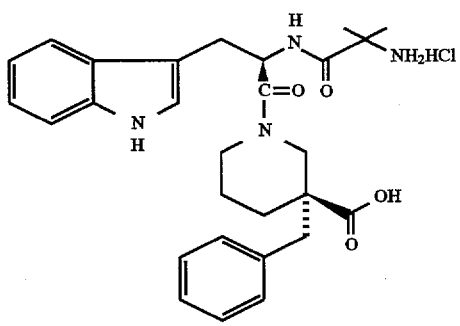

Prepared by the procedure described in Example 1, Step C from the intermediate from the previous step (211 mg, 0.357 mmol) and HCl gas in ethyl acetate (15 mL) at 0° C. for 10 minutes (175.6 mg, 93%). $^1$H NMR (CD$_3$OD, 400 MHz): The compound exists in two rotamers in approximately a 1:1 ratio. δ7.57–7.54 (m, 1H), 7.38 (d, J=8.2 Hz, 1/2H), 7.33 (d, J=8.2 Hz, 1/2H), 7.25–7.00 (m, 8H), 6.81–6.79 (m, 1H), 5.36 (dd, J=6 Hz, 8.5 Hz, 1/2H), 5.18 (app t, J=7.5 Hz, 1/2H), 4.32 (br. d, J=13 Hz, 1/2H), 4.00 (br. d, J=13 Hz, 1/2H), 3.78 (br. d, J=13 Hz, 1/2H), 3.26–3.02 (m, 11/2H), 2.86 (d, J=13.4 Hz, 1/2H), 2.80 (d, J=13.4 Hz, 1/2H), 2.53 (d, J=13.4 Hz, 1/2H), 2.46 (d, J=13.4 Hz, 1/2H), 2.29 (dt, 1/2H), 2.09 (d, J=12.7 Hz, 1/2H), 1.92–1.88 (m, 1/2H), 1.55, 1.50, 1.44 (3s, 6H), 1.40–1.25 (m, 1H), 1.20–1.12 (m, 1/2H). d1 FAB-MS calc. for $C_{28}H_{34}N_4O_4$: 490; Found 491 (M+H)

EXAMPLE 13

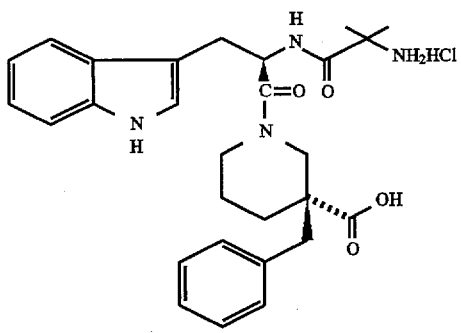

Step A:

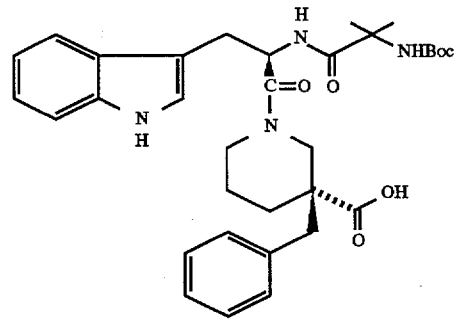

Prepared similarly from the intermediate d2 (224.2 mg, 0.33 mmol) from Example 10, Step E (169.3 mg, 87%). d2 FAB-MS calc. for $C_{33}H_{42}N_4O_6$: 590; Found 591 (M+H)

Step B:

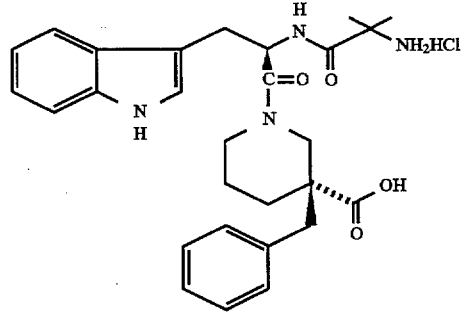

Prepared by the procedure described in Example 1, Step C from the intermediate from the previous step (139 mg, 0.235 mmol)) and HCl gas in ethyl acetate (15 mL) at 0° C. for 10 minutes (122.7 mg, 99%). $^1$H NMR (CD$_3$OD, 400 MHz): The compound exists as two rotamers in approximately a 1:1 ratio. δ8.21 (d, J=7.4 Hz, 1/2H), 7.91 (d, J=7.4 Hz, 1/2H), 7.62 (d, J=7.9 Hz, 1/2H), 7.50 (d, J=7.9 Hz, 1/2H), 7.34–6.90 (m, 9H), 5.40–5.34 (m, 1H), 4.40 (d, J=13.7 Hz, 1/2H), 4.13 (d, J=12.6 Hz, 1/2H), 3.63 (d, J=13.3 Hz, 1/2H), 3.50 (d, J=13.3 Hz, 1/2H), 3.30–3.10 (m, 7/2H), 2.93 (ABq, 1H), 2.88 (v. br. d, 1/2H), 2.60 (d, J=13 Hz, 1/2H), 2.40 (d, J=13 Hz, 1/2H), 2.19–2.16 (m, 1/2H), 1.78–1.75 (m, 1H), 1.60–1.40 (m, 3/2H), 1.20–1.10 (m, 1/2H), 1.58, 1.50, 1.47, 1.15 (4s, 6H), 1.00–0.90 (m, 1/2H).

d2 FAB-MS calc. for $C_{28}H_{34}N_4O_4$: 490; Found 491 (M+H)

The additional examples shown in Table V were prepared according to Examples 10 through 12 using Intermediate 3 and the intermediate obtained in Example 10 Step D.

TABLE V

ADDITIONAL EXAMPLES

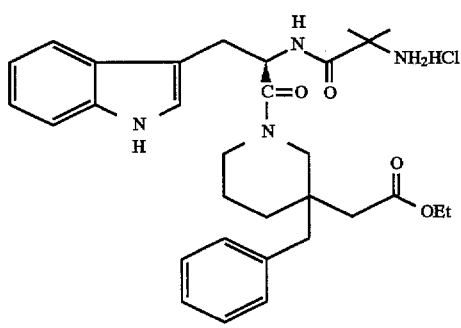

| entry | X | MF FAB-MS(M + 1) | isomer |
|---|---|---|---|
| 1 | CO2Bn | C35H43N3O4 570 | RS |
| 2 | CO2H | C28H37N3O4 480 | RS |

EXAMPLE 14

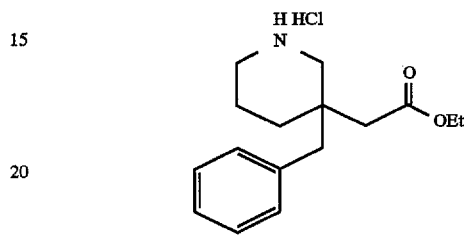

Step A:

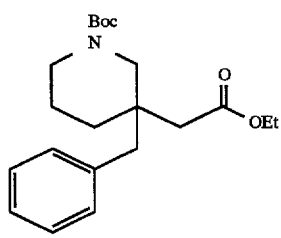

A solution of n-BuLi in hexane (4.9 mL, 12.36 mmol) was added to a stirred solution of 2,2,6,6-tetramethylpiperidine (TMP, 2.3 mL, 1.92 g, 13.5 mmol) in THF (25 mL) with ice-bath cooling. In a separate flask, a stirred mixture of ethyl N-t-Boc-3-benzyl-nipecotate (Example 1, Step B, 1.73 g, 5 mmol) and $CH_2Br_2$ (0.78 mL, 2.15 g, 12.4 mmol) in THF (20 mL) was cooled to −78° C., and the Lithium salt solution of TMP solution just prepared was then added over a 15 minute period at a temperature below −65° C. After 10 minute, a solution of LHMDS (11.2 mL, 11.2 mmol) was added over a 10 minutes period at −78° C. Following the addition, the cooling bath was removed and the mixture was allowed to warm gradually to 0° C. The mixture was cooled with an ice bath, and a solution of n-BuLi in hexane (13.5 mL, 33.7 mmol) was added at a temperature below 5° C. over a 15 minutes period. The mixture was warmed to room temperature and stirred for 45 minutes. The mixture was cooled to −78° C. and quenched over a 50 minute period by adding it into a stirred solution of acidic ethanol (30 mL) at 0° C. The mixture was evaporated to dryness and suspended in dichloromethane (100 mL), to which was added triethylamine (0.7 mL, 5.0 mmol) and di-tert-butyl dicarbonate (1.09 g, 5.0 mmol) while stirring. After 1 hour of stirring at room temperature, the material was washed with brine, dried, and concentrated. Purification by silica gel flash column chromatography, eluting with 10–30% ethyl acetate in hexane, provided the compound (1.44 g, 80%).

Step B:

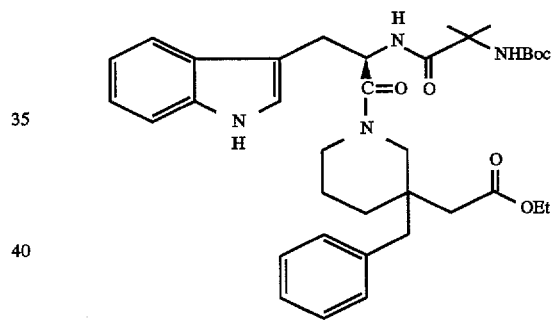

Prepared by the procedure described in Example 1, Step C, from the intermediate from the previous step (1.30 g, 3.56 mmol) and HCl gas in ethyl acetate (50 mL) at 0° C. for 45 minutes (975 mg, 91%).

FAB-MS calc. for $C_{16}H_{23}NO_2$: 261; Found 262 (M+H)

Step C:

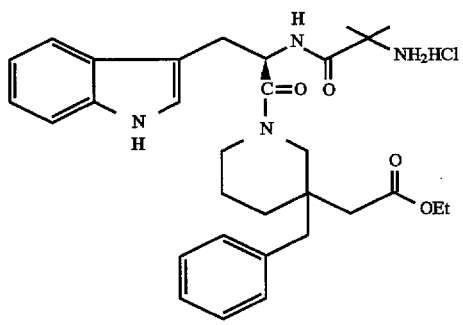

Prepared by the procedure described in Example 1, Step D from the intermediate prepared in the previous step (55 mg, 0.21 mmol), Intermediate 1 (1 eq.), HOBT (1 eq.), N-methyl morpholine (1 eq.), and EDC (80 mg, 0.42 mmol). Purification by MPLC eluting with 60% ethyl acetate in hexane provided the compound (77 mg, 61.5%).

Step E:

Prepared by the procedure described in Example 1, Step C from the intermediate from the previous step (77 mg, 0.13 mmol) and HCl gas in ethyl acetate (8 mL) at 0° C. for 15 minutes (59 mg, 85%).

FAB-MS calc. for $C_{31}H_{40}N_4O_4$: 532; Found 533 (M+H)

EXAMPLE 15

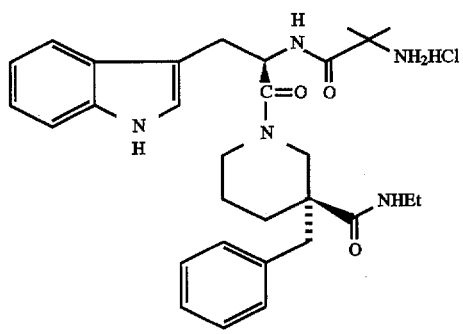

Step A:

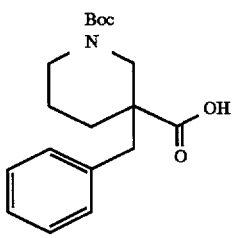

The intermediate from Example 10, Step C (1.85 g, 4.52 mmol) was hydrogenated over 1 atm of H2 and 10% palladium on carbon (150 mg) in ethanol (20 mL). Filtering through celite and evaporation yielded the acid (1.36 g, 94%). $^1$H NMR (CDCl$_3$, 400 MHz) δ 7.27–7.19 (m, 3H), 7.14–7.10 (m, 2H), 4.08–3.59 (br. m, 1H), 3.63–3.59 (m, 1H), 3.15–3.05 (br. m, 2H), 2.9. (d, J=13.5 Hz, 1H), 2.79 (d, J=13.5 Hz, 1H), 2.05–1.95 (br. m, 1H), 1.70–1.45 (m, 3H), 1.42 (s, 9H). EI-MS calc. for $C_{18}H_{25}NO_4$: 319; Found 319 (M+,)

Step B:

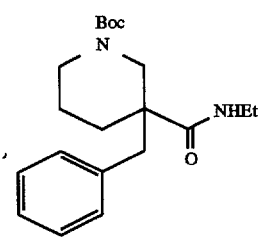

To a solution of the intermediate from the previous step (320.4 mg, 1.0 mmol) in dichloromethane containing ethyl amine hydrochloride (163 mg, 2.0 mmol), DMAP (1.0 eq.), and N-methyl morpholine (2 eq.), was added EDC (2 eq.). The reaction mixture was stirred at room temperature overnight. The solution was washed with 3N HCl and brine, dried over anhydrous magnesium sulfate, then filtered and concentrated. Purification by silica gel flash column eluting with a gradient of 60–100% ethyl acetate in hexane provided the title compound (262 mg, 76%). $^1$H NMR (CDCl$_3$, 400 MHz) δ 7.21–7.13 (m, 3H), 7.03 (d, 2H), 6.68 (br. s, 1H), 4.18 (br. d, 1H), 3.96 (br. d, 1H), 3.12–3.00 (m, 4H), 2.70–2.40 (br. m, 5H), 1.60–1.50 (m, 1H), 1.37 (s, 9H), 1.20–1.30 (m, 1H), 0.90 (q, J=7.3 Hz, 3H). EI-MS calc. for $C_{20}H_{30}N_2O_3$: 346; Found 346 (M+)

Step C:

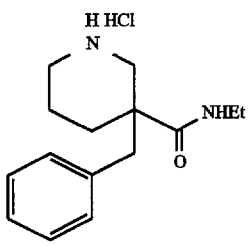

Prepared by the procedure described in Example 1, Step C from the intermediate from the previous step (262 mg, 0.76 mmol) and HCl gas in ethyl acetate (5 mL) at 0° C. for 1 hour (194 mg, 90%). $^1$H NMR (CD$_3$OD, 400 MHz) δ8.28 (br. s, 1H), 7.30–7.24 (m, 3H), 7.14–7.12 (m, 2H), 3.43 (d, J=12 Hz, 1H), 3.34–3.28 (m, 2H), 3.26–3.20(br. d, 1H), 3.11 (d, J=14 Hz, 1H), 2.88 (dt, J=3.2Hz, 13 Hz, 1H), 2.81 (d, J=12.5 Hz, 1H), 2.77 (d, J=14 Hz, 1H), 2.24 (d, J=13 Hz, 1H), 1.87 (td, J=2.8 Hz, 14 Hz, 1H), 1.75 (dt, J=3.3 Hz, 13.5 Hz, 1H), 1.64–1.55 (m, 1H), 1.17 (t, J=7 Hz, 3H).

Step D:

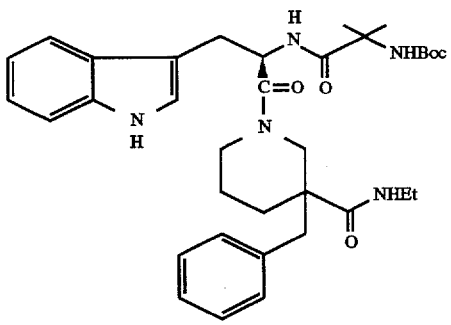

Prepared by the procedure described in Example 1, Step D from intermediate prepared in the previous step (62.2 mg, 0.22 mmol), Intermediate 1 (1 eq.), HOBT (1 eq.), N-methyl morpholine (1 eq.), and EDC (2 eq.). Purification by MPLC eluting with ethyl acetate provided two diastereomers, the one which was eluted out of the column first was designated as d1 (35.8 mg, 26%) and the one came out second was designated as d2 (43.8 mg, 31%).

d2. $^1$H NMR (CD$_3$OD, 400 MHz): The compound exists in two rotamers in approximately a 1:1 ratio. δ 8.16 (br. s, 1/2H), 7.53 (d, J=8.7 Hz, 1H), 7.32 (d, J=8.1 Hz, 1H), 7.25–6.96 (m, 8H), 6.69 (br. s, 1/2H), 5.28–5.12 (m, 1/2H), 4.94 (v. br. m, 1/2H), 4.31 (br. d, J=14.6 Hz, 1/2H), 3.49 (v. br. d, J=13 Hz, 1/2H), 3.22 (dd, J=4.7 Hz, 14.3 Hz, 1/2 H), 3.03–2.97 (m, 2H), 2.90 (d, J=13.4 Hz, 1/2H), 2.40 (br. d, 1/2H), 2.36 (d, J=13.3 Hz, 1/2H), 2.10 (d, J=13.5 Hz, 1/2H), 1.92–1.82 (br. m, 3/2H), 1.47 (s, 3H), 1.41 (s, 9H), 1.38 (s, 3H), 1.32–1.20 (m), 1.10–1.00 (dt, 1/2H), 0.85 (t, J=7.2 Hz, 3H).

d1 FAB-MS calc. for $C_{35}H_{47}N_5O_5$: 617; Found 618 (M+H) d2 FAB-MS calc. for $C_{35}H_{47}N_5O_5$: 617; Found 618 (M+H)

Step E:

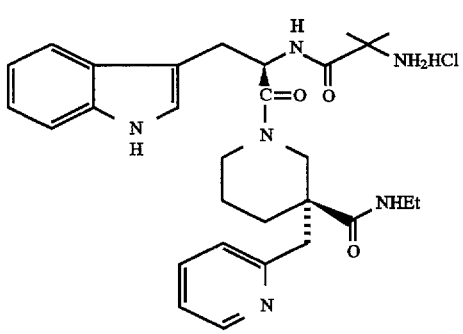

Prepared by the procedure described in Example 1, Step C from the Intermediate d1 from the previous step (35 mg, 0.057 mmol) and HCl gas in ethyl acetate (3 mL) at 0° C. for 30 minutes (32.5 mg, 100%). FAB-MS calc. for $C_{30}H_{39}N_5O_3$: 517; Found 518 (M+H)

EXAMPLE 16

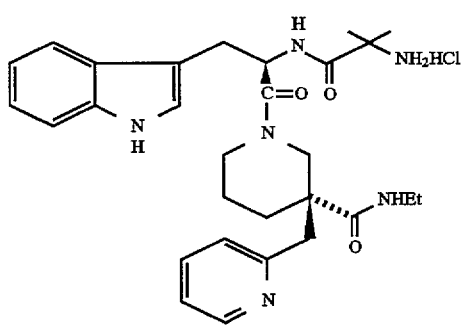

Prepared by the procedure described in Example 1, Step C from the intermediate d2 from Example 15, Step D (41 mg, 0.066 mmol) and HCl gas in ethyl acetate (3 mL) at 0° C. for 30 minutes (36.5 mg, 100%). $^1$H NMR ($CD_3OD$, 400 MHz): The compound exists in two rotamers in approximately a 4:1 ratio. δ 8.21 (d, J=7.4 Hz, 4/5H), 8.02 (d, J=7.4 Hz, 1/5H), 7.68 (d, J=7.8 Hz, 1/5H), 7.54 (d, J=7.8 Hz, 4/5H), 7.35 (d, J=7.1 Hz, 4/5H), 7.31 (d, J=7.1 Hz, 1/5H), 7.26–6.98 (m, 8H), 5.46–5.40 (m, 1/5H), 5.25–5.20 (m, 4/5H), 4.00 (br. d, 4/5H), 3.85 (br. d, 1/5H), 3.65 (br. d, J=13.2 Hz, 4/5H), 3.60–3.54 (m, 1/5H), 3.36 (br. d, 1/5H), 3.30–3.03 (m), 2.99–2.90 (m), 2.82–2.62 (m), 2.46 (d, J=13.3 Hz, 8/5H), 2.08 (br. d, 4/5H), 1.90–1.84 (m, 1/5H), 1.76–1.65 (m), 1.51, 1.49 (2s, 6H), 1.40–1.20 (m), 1.00 (t, J=7.2 Hz, 3/5H), 0.88 (t, J=7.2 Hz, 12/5H). FAB-MS calc. for $C_{30}H_{39}N_5O_3$: 517; Found 518 (M+H)

EXAMPLE 17

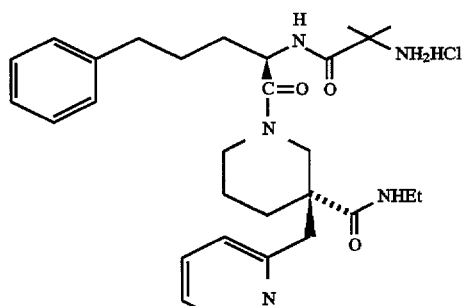

Step A

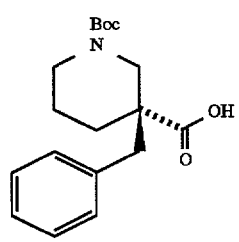

To a suspension of the S- isomer intermediate of Step A of Example 2 (27.3 g, 68.8 mmol) in 3N sodium hydroxide (25 mL), dichloromethane (200 mL) and water (100 mL), was slowly added di-t-butyl dicarbonate (18 g, 1.2 equiv.). The mixture was stirred for an additional 5 hours after the addition, it was acidified to pH 3 carefully and then extracted with ethyl acetate three times. The organic extracts were combined, dried, and concentrated to give a white solid (23.7 g). A solution of this intermediate (11.5 g, 33.1 mmol) and 3N NaOH (30 mL) in ethanol (200 mL) and water (10 mL) was refluxed for one day. The solution was evaporated to remove ethanol, and then acidified with 3N HCl to pH=3 and extracted with ethyl acetate. The extract was dried, evaporated and purified by a short silica gel column, initially eluting with 20% ethyl acetate in hexane, then with ethyl acetate to give the product (8.76 g, 83%). NMR and MS were identical to Example 15 step A.

Step B

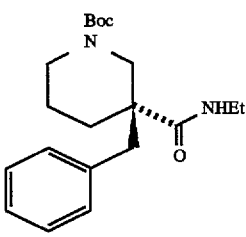

To a mixture of the intermediate from the previous step (660 mg, 2.07 mmol), ethylamine hydrochloride (251 mg, 1.5 equiv.), NMM (0.23 mL, 1 equiv.) and HOBT (1 eq) in dichloromethane and DMF (1:1, 10 mL) was added EDC. The mixture was stirred at room temperature for two days, heated at reflux for 2 hours, and was poured into a dilute HCl and brine mixture. It was extracted with ethyl acetate, and the organic layer was washed with dilute NaOH, dried and evaporated. Purification by flash column eluting with 20–80% ethyl acetate in hexane gave the product (540 mg, 75%). NMR and MS were identical to Example 15 Step B.
Step C

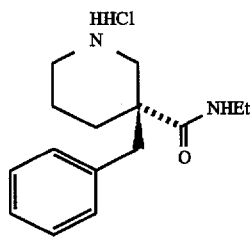

Prepared by the procedure described in Example 1, Step C from the intermediate from the previous step (0.33 g, 0.95 mmol) in ethyl acetate (5 mL) and HCl gas at 0° C. for 15 minutes (0.279 mg, 100%). FAB-MS calc. for $C_{15}H_{22}N_2O$: 246; Found 247 (M+H)
Step D

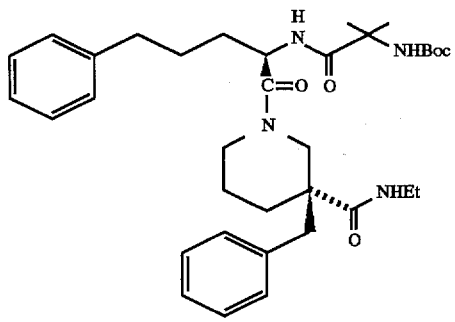

Prepared by the procedure described in Example 1, Step D from the intermediate prepared in the previous step (100 mg, 0.354 mmol), Intermediate 3 (134 mg, 0.354 mmol), HOBT (48 mg, 1 eq.), N-methyl morpholine (0.039 mL, 1 eq.), and EDC (102 mg, 1.5 eq.). Purification by MPLC, eluting with ethyl acetate, provided the intermediate (140 mg, 65%). FAB-MS calc. for $C_{35}H_{50}N_4O_5$: 606; Found 607 (M+H)

Step E

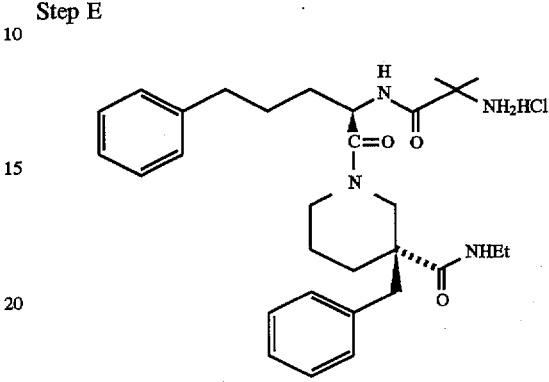

Prepared by the procedure described in Example 1, Step C from the intermediate from the previous step (132 mg, 0.217 mmol) and HCl gas in ethyl acetate (5 mL) at 0° C. for 10 minutes (113.3 mg, 96%). d1 FAB-MS calc. for $C_{30}H_{42}N_4O_3$: 506, Found: 507 (M+H)

The additional intermediates shown in Table VIa were prepared according to the above established procedure as exemplified in Example 15, and Example 17 steps A through C,. The final compounds were prepared according to Example 17 Steps D and E, using Intermediate 1.

TABLE VIa

ADDITIONAL EXAMPLES

| entry | Intermediate X | Intermediate MF FAB-MS(M + 1) | Product MF FAB-MS(M + 1) | isomer |
|---|---|---|---|---|
| 1 | —CO(morpholino) | $C_{17}H_{24}N_2O_2$ 288(M⁺,EI) | $C_{32}H_{41}N_5O_4$ 560 | S |
| 2 | —CONHCH₃ | $C_{14}H_{20}N_2O$ 233 | $C_{29}H_{37}N_5O_3$ 504 | S |
| 3 | —CONH—CH₂CO₂Et | $C_{17}H_{24}N_2O_3$ 304(M⁺,EI) | $C_{32}H_{41}N_5O_5$ 576 | S |
| 4 | —CO₂CH₂CO₂Et | $C_{17}H_{23}NO_4$ 306 | $C_{32}H_{40}N_4O_6$ 577 | R S |

TABLE VIa-continued

ADDITIONAL EXAMPLES

| | Intermediate | Product | |
|---|---|---|---|
| entry | X | Intermediate MF FAB-MS(M + 1) | Product MF FAB-MS(M + 1) | isomer |
| 5 | —CO₂(CH₂)₂SMe | C₁₆H₂₃NO₂S 294 | C₃₁H₄₀N₄O₄S 565 | R S |
| 6 | —CON(CH₃)₂ | C15H22N2O 247 | C30H39N5O3 518 | d1 d2 |
| 7 | —CONH— (CH₂)₂OH | C₁₅H₂₂N₂O₂ 263 | C₃₀H₃₉N₅O₄ 534 | S |

Likewise using 3-aminopropanol or 2-(ethylthio) ethylamine it is possible to prepare the compounds shown in Table VIb using Intermediate 1.

TABLE VIb

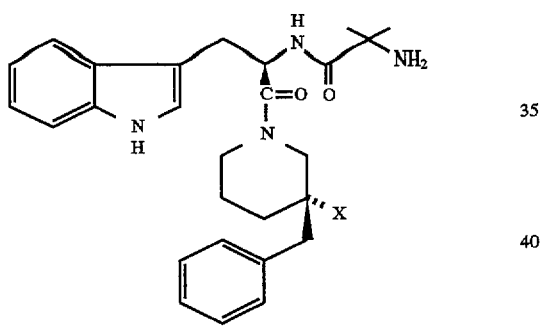

| entry | X |
|---|---|
| 1 | —CONH(CH₂)₃OH |
| 2 | —CONHCH₂CH₂SCH₃ |

The additional compounds shown in Table VIc were prepared according to Example17 Steps C and D, using some of the intermediates shown in Table VIa and Intermediate 3.

TABLE VIc

ADDITIONAL EXAMPLES

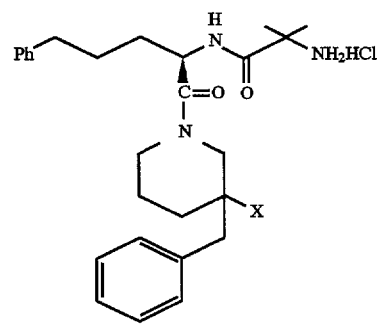

| entry | Y | MF FAB-MS(M + 1) | isomer |
|---|---|---|---|
| 1 | —CO(morpholino) | C₃₂H₄₄N₄O₄ 549 | S |
| 2 | —CONHCH₃ | C₂₉H₄₀N₄O₃ 493 | S |
| 3 | —CONH— CH₂CO₂Et | C₃₂H₄₄N₄O₅ 565 | S |
| 4 | —CONH— (CH₂)₂OH | C₃₀H₄₂N₄O₄ 523 | S |

Likewise using 3-aminopropanol and 2-(methylthio) ethylamine it is possible to prepare the compounds shown in Table VId.

TABLE VId

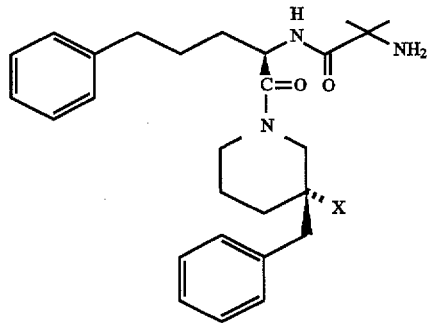

| entry | X |
|---|---|
| 1 | —CONH(CH₂)₃OH |
| 2 | —CONHCH₂CH₂SCH₃ |

The additional compounds shown in Table VIe were prepared according to Example17 Steps C and D, using some of the intermediates shown in Table VI and Intermediate 2.

TABLE VIe

ADDITIONAL EXAMPLES

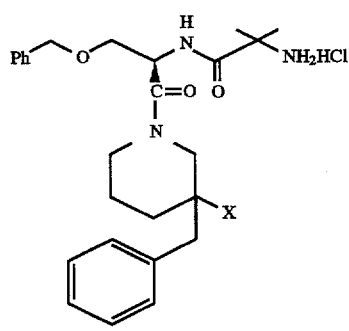

| entry | Y | MF FAB-MS(M + 1) | isomer |
|---|---|---|---|
| 1 | —CO(morpholino) | C₃₁H₄₂N₄O₅ 551 | S |
| 2 | —CONHCH₃ | C₂₈H₃₈N₄O₄ 495 | S |
| 3 | —CONH—CH₂CO₂Et | C₃₁H₄₂N₄O₆ 567 | S |

EXAMPLE 18

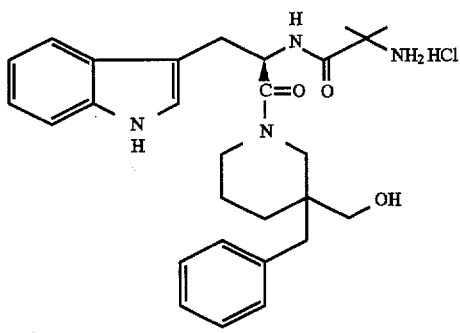

Step A:

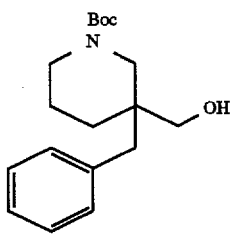

To a stirred solution of ethyl N-t-Boc-3-phenylmethyl nipecotate (10.4 g, 29.93 mmol) in dichloromethane (100 mL) at −78° C. was added DIBAL (1M, 45 mL). The reaction was stirred at −78° C. for 4 hours and quenched by the addition of methanol (5 mL). The reaction mixture was washed carefully with tartaric acid water solution and brine, dried over MgSO₄ and evaporated. Silica gel flash chromatography eluting with a gradient of 40–80% ethyl acetate in hexane yielded the product (6.81 g, 75%).

EI-MS calc. for $C_{18}H_{27}NO_3$: 305; Found 305 (M+)

Step B:

3-Phenylmethyl-3-piperidinemethanol hydrochloride

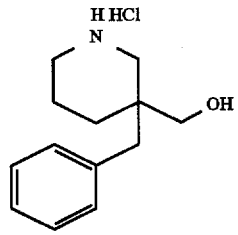

A solution of the intermediate from the previous step (770 mg, 2.52 mmol) in ethanol (20 mL) and concentrated HCl (1 mL) was refluxed for 3 hours. The reaction mixture was cooled to room temperature and evaporated to give the title compound as a white solid. (609.0 mg, 100%)

¹H NMR (CD₃OD, 400 MHz) δ 7.31–7.19 (m, 5H), 3.45 (ABq, J=11 Hz, 2H), 3.18 (d, J=13 Hz, 1H), 3.19–3.13 (m, 1H), 3.03–2.99 (m, 1H), 2.96 (d, J=13 Hz, 1H), 2.72 (s, 1H), 1.92–1.84 (m, 2H), 1.60–1.50 (m, 2H).

EI-MS calc. for $C_{12}H_{17}NO$: 191; Found 191 (M+,)

Step C:

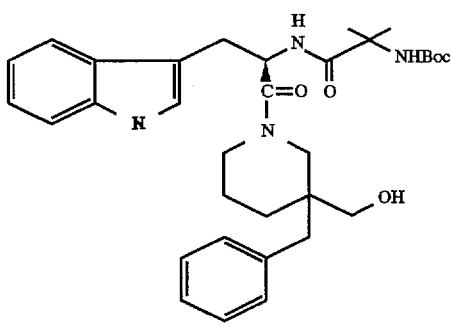

Prepared by the procedure described in Example 1, Step D from the intermediate prepared in the previous step (142 mg, 0.587 mmol), Intermediate 1 (0.8 eq.), HOBT (1 eq.), N-methyl morpholine (1 eq.), and EDC (2 eq.). Purification by MPLC eluting with ethyl acetate gave two compounds; the compound which came out of the column first is designated as d1 (98.5 mg, 58%) and the compound which came out of the column next as d2 (34.5 mg, 12%)

d1 FAB-MS calc. for $C_{32}H_{42}N_4O_5$: 562; Found 563 (M+H) d2 FAB-MS calc. for $C_{32}H_{42}N_4O_5$: 562; Found 563 (M+H)

Step D:

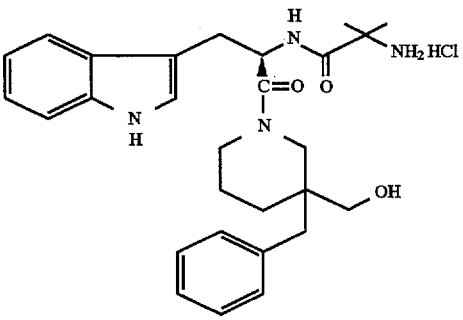

The intermediate (d1) from the previous step (60 mg, 0.104 mmol) was treated with HCl gas at 0° C. in ethyl acetate (3 mL) for five minutes. Evaporation gave the diastereomer 1 of the title compound.

d1 F/LB-MS calc. for $C_{28}H_{36}N_4O_3$: 476; Found 477 (M+H)

The intermediate (d2) from Step C (20 mg) was treated with HCl gas at 0° C. in ethyl acetate (3 mL) for five minutes. Evaporation gave the diastereomer 2 of the title compound.

d2 FAB-MS calc. for $C_{28}H_{36}N_4O_3$: 476; Found 477 (M+H)

EXAMPLE 19

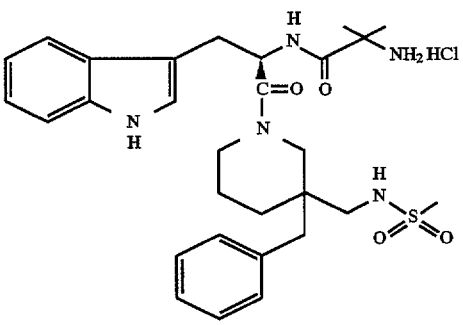

Step A:

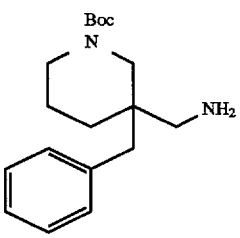

To a stirred solution of intermediate from Example 18, Step A (5.12 g, 16.8 mmol), and triethylamine (4.7 mL) in dichloromethane at 0° C. was added mesyl chloride (1.95 mL). The reaction mixture was stirred for 2 hours. The solution was poured into a mixture of brine and 3 N HCl and extracted with ethyl acetate. The organic layer was washed with saturated sodium bicarbonate, dried over magnesium sulfate and evaporated to yield the mesylate. The mesylate was heated with sodium azide (2.2 g, 33.6 mmol) in DMSO (20 mL) at 80° C. for two weeks. The mixture was poured into ice water and extracted with ethyl acetate. The organic layer was washed with saturated sodium bicarbonate and brine; it was dried, and evaporated. Purification by silica gel flash column chromatography provided the azide (4.14 g, 75%).

$^1$H NMR (CDCl$_3$, 200 MHz) δ 7.29–7.13 (m, 5H), 3.61–3.57 (br. m, 1H), 3.47 (d, J=12 Hz, 1H), 3.20–3.10 (v. br. s, 2H), 3.10–2.96 (v. br. d, 1H), 2.60–2.45 (br. m, 2H), 1.65–1.48 (m, 4H), 1.44 (s, 9H), 1.41–1.35 (m, 1H).

FAB-MS calc. for $C_{18}H_{26}N_4O_2$: 330; Found 331 (M+H)

Step C:

The azide from the previous step (1.60 g, 4.84 mmol) was hydrogenated over 10% palladium on carbon (160 mg) in ethanol (25 mL) under a 1 atm hydrogen balloon for 2 hours. The reaction mixture was filtered through celite and evaporated to give the amine (1.42 g, 96%). FAB-MS calc. for $C_{18}H_{28}N_2O_2$: 304; Found 305 (M+H)

Step D:

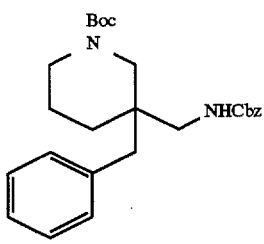

To a stirred solution of the amine from the previous step (1.30 g, 4.27 mmol) in dichloromethane (20 mL) which also contained DMAP (20 mg) and triethylamine (1 mL) at 0° C., was added CbzCl (0.73 mL, 5.12 mmol). The reaction mixture was stirred for 2 hours. The solution was poured into a mixture of brine and 3N HCl and extracted with ethyl acetate. The organic layer was washed with saturated sodium bicarbonate, dried over magnesium sulfate and evaporated to give a residue which was purified by flash chromatography, eluting with 20% ethyl acetate in hexane, to yield the product (1.52 g).

FAB-MS calc. for $C_{26}H_{34}N_2O_4$: 438; Found 439 (M+H)

Step E:

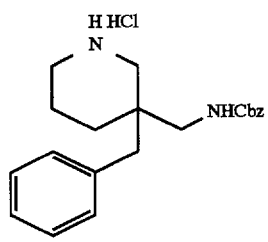

To a stirred solution of the intermediate from the previous step (1.50 g, 3.42 mmol) in ethyl acetate (50 mL) at 0° C. was bubbled HCl until it was saturated. The reaction mixture was stirred for one hour and evaporated to yield the salt (1.32 g, 100%).

$^1$H NMR (CD$_3$OD, 400 MHz) δ 7.40–7.18 (m, 10H), 5.14 (s, 2H), 3.43, 3.42 (2 d, J=14.8 Hz, 1H), 3.23 (td, J=4 Hz, 12.1 Hz, 1H), 3.00 (d, J=13 Hz, 1H), 2.94 (d, J=14.7 Hz, 1H), 2.83 (dt, J=3.4 Hz, 12 Hz, 1H), 2.74 (d, J=13 Hz, 1H), 2.68 (d, J=13.6 Hz, 1H), 2.62 (d, J=13.6 Hz, 1H), 2.00–1.90 (m, 1H), 1.92–1.88 (m, 1H), 1.59–1.52 (m, 1H), 1.47–1.44 (m, 1H).

FAB-MS calc. for $C_{21}H_{26}N_2O_2$: 338; Found 339 (M+H)

Step F:

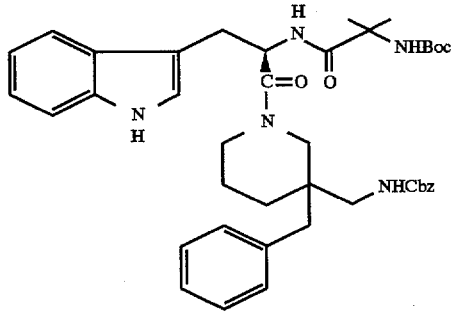

Prepared by the procedure described in Example 1, Step D from the intermediate prepared in the previous step (1.00 g, 2.67 mmol), Intermediate 1 (1.04 g, 1 eq.), HOBT (1 eq.), N-methyl morpholine (2 eq.), and EDC (820 mg, 4.27 mmol). Purification by MPLC, eluting with 60% ethyl acetate in hexane, provided the compound. (1.54 g, 81%)

Step G:

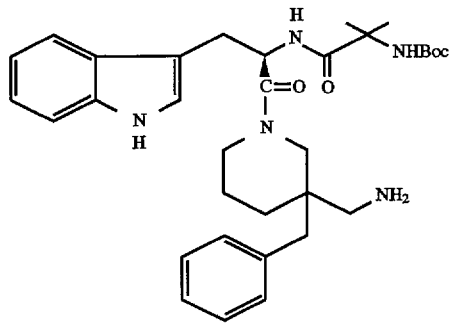

The intermediate from the previous step (1.30 g, 1.83 mmol) was hydrogenated over 10% palladium on carbon (100 mg) in ethanol (15 mL) under a hydrogen balloon. The reaction mixture was filtered through celite and evaporated to yield the amine (1.20 g, 100%).

FAB-MS calc. for $C_{33}H_{45}N_5O_4$: 575; Found 576 (M+H)

Step H:

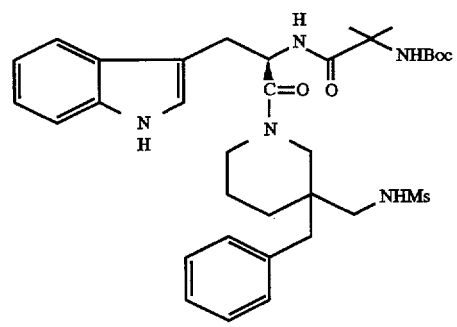

To a stirred solution of the intermediate prepared the previous step (286 mg, 0.497 mmol), DMAP (10 mg) and N-methyl morpholine (0.109 mL) in dichloromethane (10 mL) at 0° C. was added mesyl chloride (0.042 mL). The reaction mixture was stirred for 2 hours. The solution was poured into a mixture of brine and 3N HCl and extracted with ethyl acetate. The organic layer was washed with saturated sodium bicarbonate dried over magnesium sulfate and evaporated to give a residue which was purified by flash chromatography, eluting with 90% ethyl acetate in hexane, to give the product (285.9 mg, 88%). FAB-MS calc. for $C_{34}H_{47}N_5O_6S$: 653; Found 654 (M+H)

Step I:

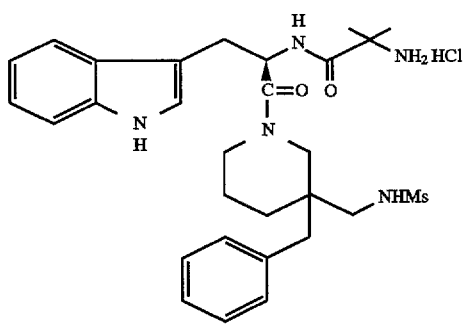

Prepared by the procedure described in Example 1, Step C from the intermediate from the previous step (265 mg, 0.405 mmol) and HCl gas in ethyl acetate (8 mL) at 0° C. for 30 minutes (189 mg, 79%)

FAB-MS calc. for $C_{29}H_{39}N_5O_4S$: 553; Found 554 (M+H)

EXAMPLE 20

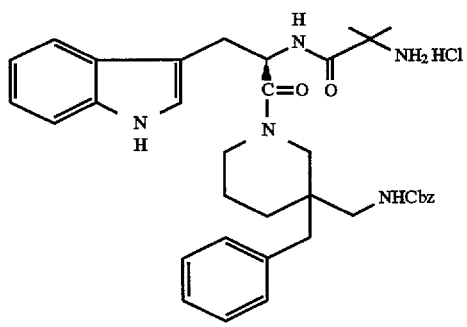

Prepared by the procedure described in Example 1, Step C from the intermediate from Example 19, Step F (109 mg, 0.154 mmol) and HCl gas in ethyl acetate (4 mL) at 0° C. for 30 minutes (90 mg, 90%).

FAB-MS calc. for $C_{36}H_{43}N_5O_4$: 609; Found 610 (M+H)

EXAMPLE 21

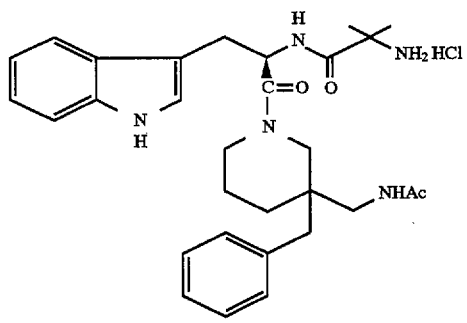

Step A:

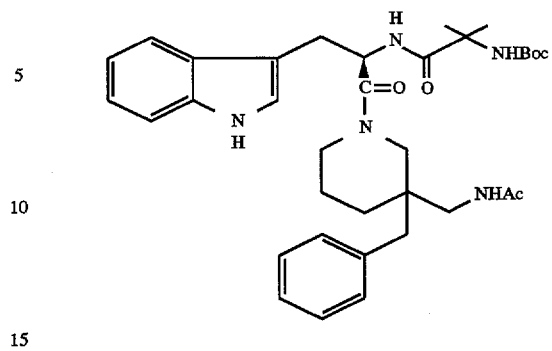

The mixture of the intermediates from Example 19, Step G (208 mg, 0.362 mmol) and pyridine (2 mL) and acetic anhydride (2 mL) was heated at 60° C. for 30 minutes. The mixture was then evaporated under vacuum. MPLC purification eluting with 80% ethyl acetate in hexane yielded the product (202 mg, 90%).

FAB-MS calc. for $C_{35}H_{47}N_5O_5$: 617; Found 618 (M+H)

Step B:

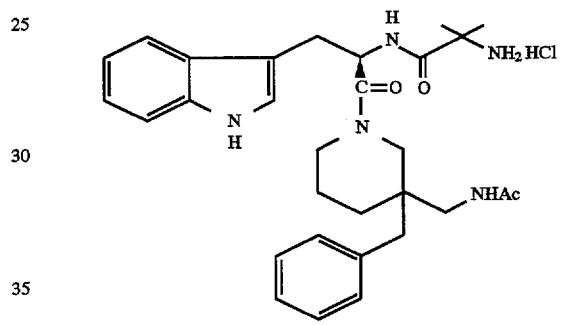

Prepared by the procedure described in Example 1, Step C from the intermediate from the previous step (192 mg, 0.311 mmol) and HCl gas in ethyl acetate (4 mL) at 0° C. for 30 minutes (168.1 mg, 98.5%).

FAB-MS calc. for $C_{30}H_{39}N_5O_3$: 517; Found 518 (M+H)

EXAMPLE 22

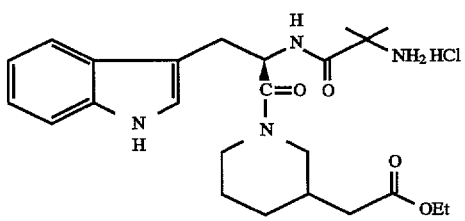

Step A:

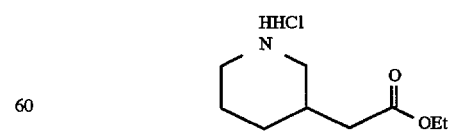

A suspension of platinum (IV) oxide (200 mg), ethyl 3-pyridylacetate (5.0 g, 30.3 mmol) and concetrated hydrochloric acid (10 mL) in ethanol (50 mL) was stirred under a hydrogen balloon overnight. The mixture was filtered through celite and evaporated to yield a residue, which was refluxed with anhydrous acidic ethanol for 30 minutes. Evaporation yielded the product (6.28 g, 100%).

¹H NMR (CD₃OD, 400 MHz) δ 4.13 (q, J=7.2 Hz, 2H), 3.40 (dd, J=3.5 Hz, 12 Hz, 1H), 3.35 (br. d, 1H), 2.90 (br. t, 1H), 2.73 (t, J=12 Hz, 1H), 2.35 (d, J=7.5 Hz, 2H), 2.26–2.17 (m 1H), 1.96–1.80 (br. m, 2H), 1.80–1.70 (m, 1H), 1.37–1.26 (m, 1H), 1.24 (t, J=7.1 Hz, 3H).

Step B:

Prepared by the procedure described in Example 1, Step D from the intermediate prepared in the previous step (128 mg, 0.617 mmol), Intermediate 1 (200 mg, 0.514 mmol), HOBT (1 eq.), N-methyl morpholine (1 eq.), and EDC (200 mg). Purification by MPLC eluting with 80% ethyl acetate in hexane provided the compound. (247 mg, 89%)

Step C:

Prepared by the procedure described in Example 1, Step C from the intermediate from the previous step (225 mg, 0.415 mmol) and HCl gas in ethyl acetate (5 mL) at 0° C. for 15 minutes (184 mg, 100%).

FAB-MS calc. for $C_{24}H_{34}N_4O_4$: 442; Found 443 (M+H)

EXAMPLE 23

Step A:

The less polar (d 1) intermediate from Example 8 step A (7.25 g, 17.08 mmol) was refluxed for 8 hours in ethanol (20 ml) and 10N NaOH (8.5 mL). The mixture was then cooled to room temperature and slowly treated with 3N HCl to pH=11. To this stirred solution was added di-tert-butyl dicarbonate in dioxane (20 mL) and stirred for two hours. The solution was acidified to pH 4 and then neutralized to pH 7 and extracted with ethyl acetate three times. The organic extracts were combined, dried, and concentrated to give white solid (6.80 g).

FAB-MS calc. for $C_{17}H_{24}N_2O_4$: 320, Found: 321 (M+H)

Step B:

To a solution of the intermediate from the last step (6.5 g), benzyl alcohol (2 equiv.), and DMAP (20 mg) in dichloromethane (100 mL), was added EDC (1.2 equiv.). The mixture was stirred at room temperature for three days, and was poured into dilute NaHCO3 solution. It was extracted with ethyl acetate three times, and dried over MgSO4. Evaporation and purification by a flash column eluting with 40% ethyl acetate in hexane gave the desired product.(6.53 g, 78%).

FAB-MS calc. for $C_{24}H_{30}N_2O_4$: 410; Found 411 (M+H); 311 (M⁺-Boc(100)).

Step C:

Prepared by the procedure described in Example 1, Step C from the intermediate from the previous step (1.0 g, 2.44 mmol) in ethyl acetate (40 mL) and HCl gas at 0° C. for 15 minutes (935 mg, 99%).

FAB-MS calc. for $C_{19}H_{22}N_2O_2$: 310; Found 311 (M+H)

Step D:

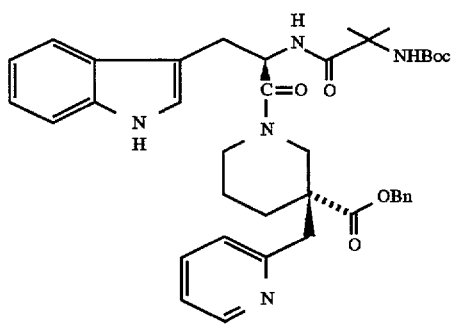

Prepared by the procedure described in Example 1, Step D from the intermediate prepared in the previous step (800 mg, 2.09 mmol), intermediate 1 (812 mg, 2.09 mmol), HOBT (1 eq.), N-methyl morpholine (1 eq.), and EDC (2 eq.). Purification by MPLC, eluting with 80% ethyl acetate in hexane, provided the Intermediate (1.10 g, 77%) d1 FAB-MS calc. for $C_{39}H_{47}N_5O_6$: 681; Found 682 (M+H)

Step E:

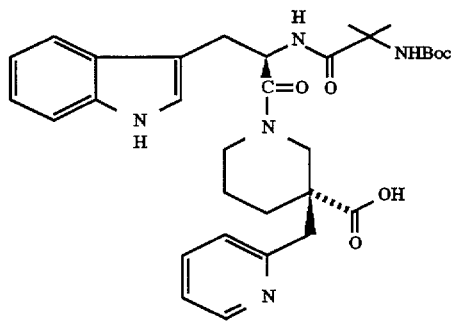

A suspension of 10% palladium on carbon (150 mg) and the intermediate from previous step (1.05 g, 1.54 mmol) in ethanol (20 mL) was vigorously stirred under a hydrogen atmosphere for 30 minutes. The reaction mixture was then filtered through celite and evaporated to give the product (828 mg, 91%). dl FAB-MS calc. for $C_{32}H_{41}N_5O_6$: 591; Found 592 (M+H)

Step F:

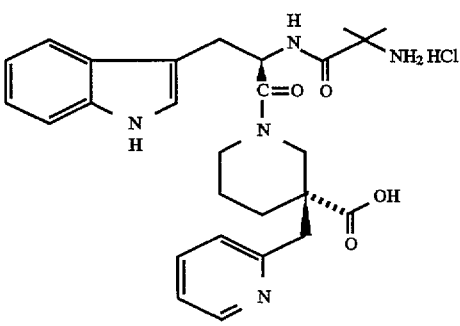

Prepared by the procedure described in Example 1, Step C from the intermediate from the previous step (211 mg, 0.357 mmol) and HCl gas in ethyl acetate (15 mL) at 0° C. for 10 minutes (175.6 mg, 93%). d1 FAB-MS calc. for $C_{27}H_{33}N_5O_4$: 491 Found 492 (M+H)

EXAMPLE 24

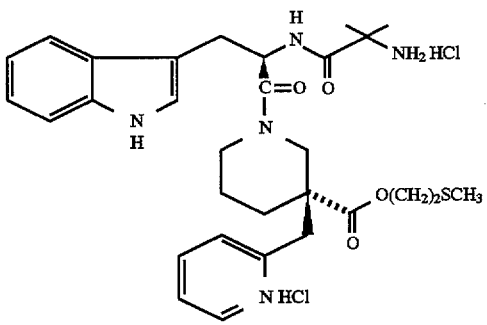

Step A:

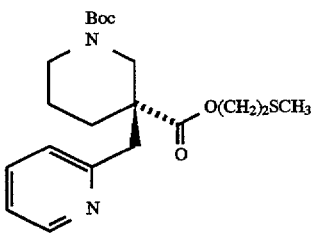

To a stirred solution of the product from Example 23, step A (5.79 g, 18.1 mmol), 2-(methylthio)ethanol (2.49 g, 27.1 mmol), DMAP (220 mg) in dichloromethane (100 mL) was added EDC and the mixture was stirred for one day. The reaction mixture was washed with brine, dried, evaporated, and purified on silica gel column eluting with 60% ethyl acetate in hexane to give the desired compound (6.64 g, 94%)

FAB-MS calc. for $C_{20}H_{30}N_2O_4S$: 394, Found: 395 (M+H)

Step B:

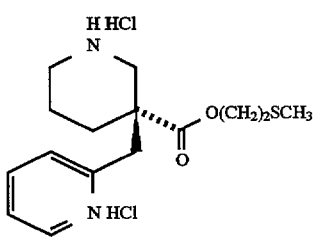

Prepared by the procedure described in Example 1, Step C from the intermediate from the previous step (6.12 g, 15.5 mmol) in ethyl acetate (30 mL) and HCl gas at 0° C. for 30 minutes (5.38 g, 95%).

FAB-MS calc. for $C_{15}H_{22}N_2O_2S$: 294; Found 295 (M+H)

Step C:

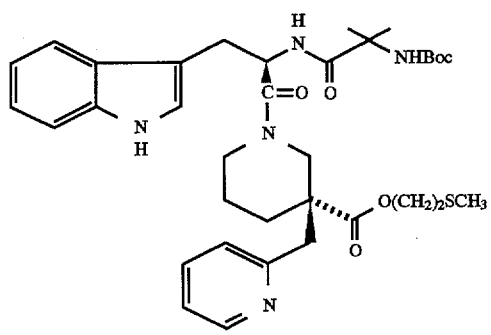

Step D:

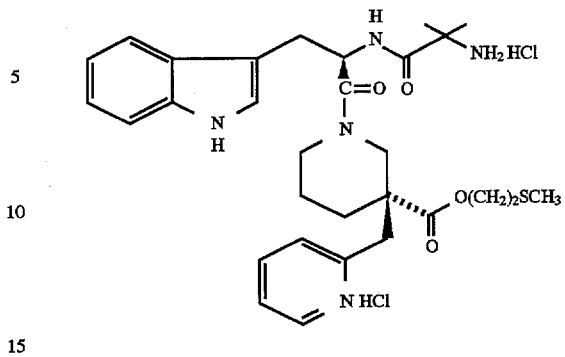

Prepared by the procedure described in Example 1, Step D from the intermediate prepared in the previous step (2.0 g, 5.44 mmol), Intermediate 1 (2.12, 5.44 mmol), HOBT (1 eq.), N-methyl morpholine (1 eq.), and EDC (1.5 eq.). Purification by MPLC, eluting with 80–100% ethyl acetate in hexane, provided the intermediate (3.44 g, 95%)

FAB-MS calc. for $C_{35}H_{47}N_5O_6S$: 665; Found 666(M+H)

Prepared by the procedure described in Example 1, Step C from the intermediate from the previous step (2.94 g, 4.42 mmol) in ethyl acetate (10 mL) and HCl gas at 0° C. for 20 minutes (2.80 g, 99%).

FAB-MS calc. for $C_{30}H_{39}N_5O_4S$: 565; Found 566(M+H)

The additional intermediates shown in Table VII were prepared according to the above established procedure as exemplified in Example 24, steps A and B,. The final compounds were prepared according to Example 17 Steps D and E, using Intermediate 1.

TABLE VII

| entry | Intermediate X | Intermediate MF FAB-MS(M + 1) | Final Product MF FAB-MS(M + 1) | isomer |
|---|---|---|---|---|
| 1 | $CO_2(CH_2)_2SMe$ | $C_{15}H_{22}N_2O_2S$ 295 | $C_{30}H_{39}N_5O_4S$ 566 | R |
| 2 | $CO_2Bn$ | $C_{19}H_{22}N_2O_2$ 311 | $C_{34}H_{39}N_5O_4$ 582 | R |
| 3 | $CO_2Bn$ | $C_{19}H_{22}N_2O_2$ 311 | $C_{34}H_{39}N_5O_4$ 582 | S |
| 4 | $CO_2(CH_2)_3CH_3$ | $C_{16}H_{24}N_2O_2$ 277 | $C_{31}H_{41}N_5O_4$ 548 | RS |
| 5 | $CO_2(CH_2)_2CH_3$ | $C_{15}H_{22}N_2O_2$ 263 | $C_{30}H_{39}N_5O_4$ 534 | RS |
| 6 | $CO_2CH(CH_3)_2$ | $C_{15}H_{22}N_2O_2$ 263 | $C_{30}H_{39}N_5O_4$ 534 | RS |
| 7 | $CONH(CH_2)_3CH_3$ | $C_{16}H_{25}N_3O$ 276 | $C_{31}H_{42}N_6O_3$ 547 | RS |
| 8 | $CONHCH(CH_3)_2$ | $C_{15}H_{23}N_3O$ 262 | $C_{30}H_{40}N_6O_3$ 533 | RS |
| 9 | $CO_2CH_2CO_2Et$ | $C_{16}H_{22}N_2O_4$ 306 | $C_{31}H_{39}N_5O_6$ 578 | RS |
| 10 | CONHEt | $C_{14}H_{21}N_3O$ 248 | $C_{29}H_{38}N_6O_3$ 519 | RS |
| 11 | $CONHCH_2CO_2Et$ | $C_{16}H_{23}N_3O_3$ 307 | $C_{31}H_{40}N_6O_5$ 577 | RS |

Note:
RS compounds were prepared by using racemic intermediates instead of chiral ones.

EXAMPLE 24A

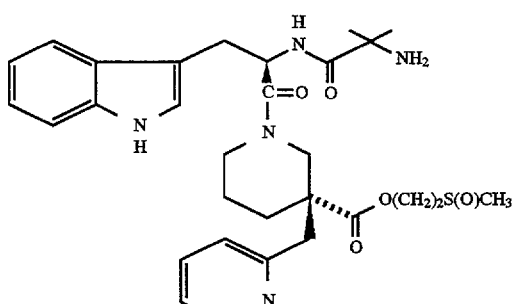

To a stirred solution of the final product from Example 24 (120 mg, 0.188 mmol) in ethanol/water (3/2 mL), was added sodium periodate (100 mg, 0.467 mmol) and the resulting mixture was stirred at room temperature for six hours. The reaction mixture was then poured into saturated sodium bicarbonate solution (10 mL) and extracted with dichloromethane (10 mL, 3 times). The organic extracts were combined and evaporated to give the desired compound (89 mg, 81%).

FAB-MS calc. for $C_{30}H_{39}N_5O_5S$: 581; Found 582(M+H)

EXAMPLE 25

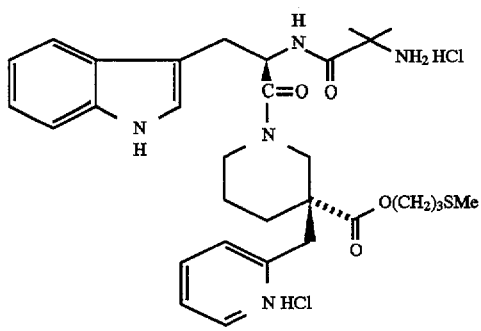

Step A:

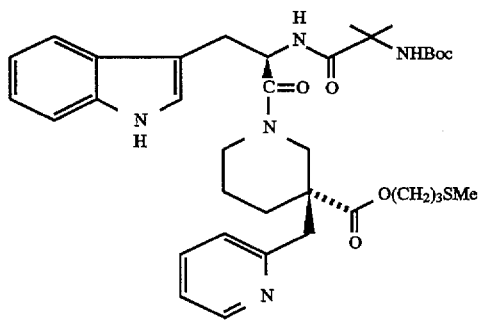

To a stirred solution of the intermediate from Example 23, step E (100 mg, 0.17 mmol), 3-(methylthio) propanol (18 mg, 0.17 mmol) and DMAP (3 mg) in dichloromethane (15 mL) was added EDC (1.5 equiv.), and the mixture was stirred at room temperature for one day. The reaction mixture was washed with water and brine, dried, evaporated and purified by MPLC eluting with 80% ethyl acetate in hexane to give the desired compound (88 mg). FAB-MS calc. for $C_{36}H_{49}N_5O_6S$: 679; Found 680(M+H)

Step B:

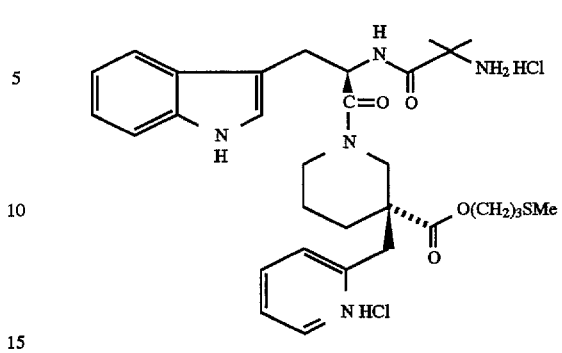

Prepared by the procedure described in Example 1, Step C from the intermediate from the previous step(85 mg, 0.125 mmol) in ethyl acetate (3 mL) and HCl gas at 0° C. for 20 minutes (74 mg, 95%).

FAB-MS calc. for $C_{31}H_{41}N_5O_4S$: 579; Found 580(M+H)

The compounds shown in Table VIII were prepared according to the above established procedure as exemplified in Example using appropriate amines and alcohols.

TABLE VIII

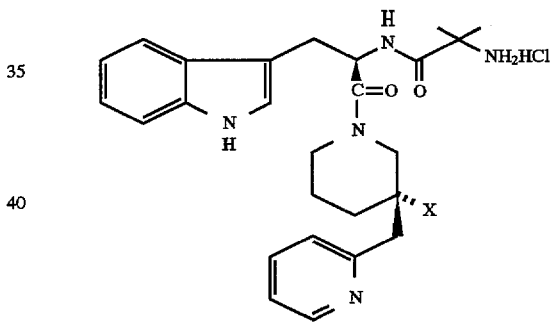

| entry | X | MF FAB-MS(M + 1) |
|---|---|---|
| 1 | CO(morpholine) | $C_{31}H_{40}N_6O_4$ 560(M+,EI MS) |
| 2 | $CO_2(CH_2)_4SMe$ | $C_{32}H_{43}N_5O_4S$ 594 |
| 3 | $CONH(CH_2)_2SMe$ | $C_{30}H_{40}N_6O_3S$ 565 |
| 4 | CONHEt | $C_{29}H_{38}N_6O_3$ 519 |
| 5 | $CONH(CH_2)_2OH$ | $C_{29}H_{38}N_6O_4$ 535 |

Likewise using the intermediate from Example 23, Step C and following the procedures described in Step D and E using Intermediate 3 instead of Intermediate 1, the compounds shown in Table VIIIa were prepared according to the established procedures as exemplified in Example 25 using appropriate amines.

TABLE VIIIa

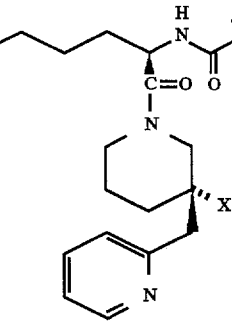

| entry | X | MF FAB-MS(M + 1) |
|---|---|---|
| 1 | CONHEt | $C_{29}H_{41}N_5O_3$ 508 |
| 2 | CONH(CH$_2$)$_2$OH | $C_{29}H_{41}N_5O_4$ 524 |

Likewise using the intermediate from Example 23, Step E and following the procedure described above; or the intermediate from Example 23, step A and following the procedure described in Example 24 steps A through D using Intermediate 1 or Intermediate 3 the compounds shown in Table VIIIb may be prepared.

TABLE VIIIb

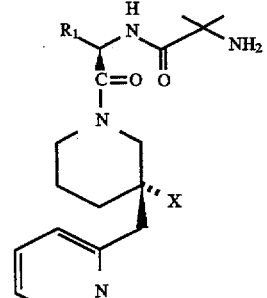

| entry | R1 | X |
|---|---|---|
| 1 | indol-3-yl-CH$_2$— | —CONHCH$_3$ |
| 2 | phenyl-(CH$_2$)$_3$— | —CONHCH$_3$ |
| 3 | indol-3-yl-CH$_2$— | —CONH(CH$_2$)$_3$OH |
| 4 | phenyl-(CH$_2$)$_3$— | —CONH(CH$_2$)$_3$OH |
| 5 | phenyl-(CH$_2$)$_3$— | —CONHCH$_2$CH$_2$SCH$_3$ |

EXAMPLE 26

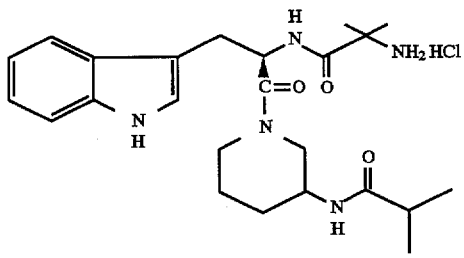

Step A:

3-Carbobenzyloxyaminopyridine

To a solution of 3-aminopyridine (10 g, 0.106 mol) and triethyl amine (16.3 mL, 0.117 mol) in dichloromethane (100 mL) at 0° C., was added benzyl chloroformate (15.2 mL, 0.106 mol) slowly. The reaction mixture was stirred overnight and was washed with water, saturated NaHCO3, dried over MgSO4, and evaporated. The residue was purified on a silica gel column to give the product (9.51 g)

FAB-MS calc. for $C_{13}H_{12}N_2O_2$: 228; Found 229(M+H)

Step B:

3-Carbobenzyloxyaminopiperidine

A solution of the intermediate from the previous step (9.51 g, 41.7 mmol) and hydrochloric acid (3.5 mL, 41.7 mmol) in ethanol (300 mL) was hydrogenated over PtO2 (0.9 g) and hydrogen (1 atm) overnight. Filtration and evaporation gave the product as a brown solid. FAB-MS calc. for $C_{13}H_{18}N_2O_2$: 234; Found 235(M+H)

Step C:

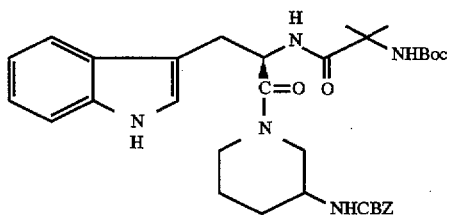

To a solution of the intermediate from the previous step (4.65 g, 17.2 mmol), Intermediate 1 (6.68 g, equiv.), HOBT (2.32 g, 1 equiv.) and NMM (2.1 mL, 1 equiv.) in dichloromethane (100 mL), was added EDC (3.94 g, 1.2 equiv.). The reaction mixture was stirred overnight and worked up by washing with water, saturated NaHCO3, dried over MgSO4 and evaporated. Purification on a $SiO_2$ column gave 2.5 g of the desired product.

FAB-MS calc. for $C_{33}H_{43}N_5O_6$: 605; Found 606(M+H)

Step D:

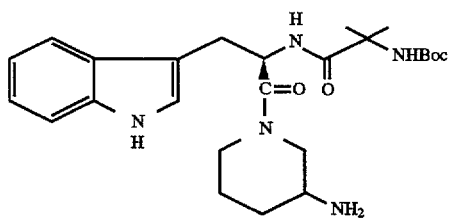

A suspension of the intermediate from the previous step (2.5 g) and Pd(OH)$_2$/C (250 mg, 10%) in methanol (60 mL) was stirred under H2 (1 atm) for three days. The reaction mixture was filtered through celite and evaporated to give the desired material.

FAB-MS calc. for $C_{25}H_{37}N_5O_4$: 471; Found 472(M+H)

Step E:

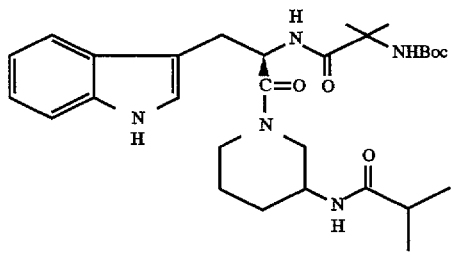

To a solution of the intermediate from the previous step (236 mg, 0.5 mmol) and N,N-diisopropylethylamine (0.11 mL, 0.6 mmol) in dichloromethane (10 mL), was added isobutyryl chloride (0.053 mL, 0.5 mmol) at 0°. The reaction mixture was stirred for 2 hours and was washed with water, brine, dried over MgSO4 and evaporated. SiO$_2$ flash column chromatography eluting with 90–100% ethyl acetate in hexane yielded the product.

FAB-MS calc. for $C_{29}H_{43}N_5O_5$: 541; Found 542(M+H)

Step F:

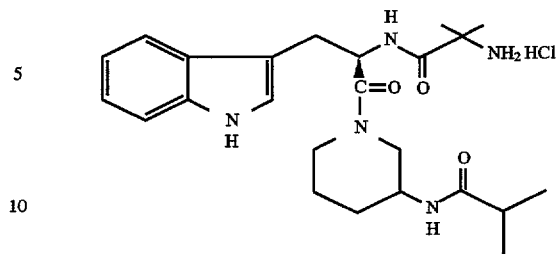

To a solution of the intermediate from the previous step in ethyl acetate (5 mL) at 0° C. was bubbled HCl until it was saturated. The mixture was stirred for 30 minutes and evaporated to dryness to give the product. FAB-MS calc. for $C_{24}H_{35}N_5O_3$: 441; Found 442(M+H)

Similarly the following compounds were prepared according to the same procedure as described above, but using different acylating reagents.

TABLE IX

| entry | Acylating agent | Y | MF FAB-MS(M + 1) |
|---|---|---|---|
| 1 | Ac$_2$O | AcNH | $C_{22}H_{31}N_5O_3$ 414 |
| 2 | ChxCOCl | ChxCONH | $C_{27}H_{39}N_5O_3$ 482 |
| 3 | ChxCH$_2$COCl | ChxCH2CONH | $C_{28}H_{41}N_5O_3$ 496 |
| 4 | BzCl | BzNH | $C_{27}H_{33}N_5O_3$ 476 |
| 5 | PhSO$_2$Cl | PhSO2NH | $C_{26}H_{33}N_5O_4S$ 512 |
| 6 | iso-PrNCO | iso-PrNHCONH | $C_{24}H_{36}N_6O_3$ 457 | note:
Chx: cyclohexyl, Bz: benzoyl

EXAMPLE 27

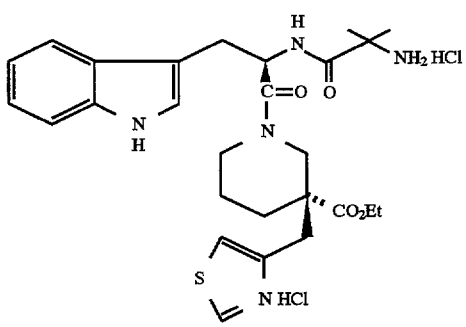

Step A:

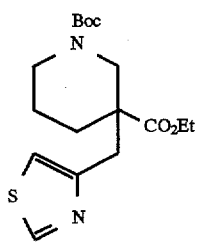

To a stirred solution of KHMDS (27.4 g, 0.138 mol) in THF (500 mL) at −78° C. under argon was added ethyl N-t-Boc nipecotate (28.3 g, 0.11 mol) in THF (100 mL) over a 20 minute period. The solution was allowed to stir an additional 30 minutes at −78° C. Then, a solution of 4-bromomethylthiazole or 4-chloromethylthiazole in THF (100 mL) was added slowly to the reaction mixture. 4-Bromomethylthiazole was prepared by refluxing 4-methylthiazole (10 mL, 0.11 mmol), N-bromosuccinimide (19.6 g, 0.11 mol) and AIBN (0.2 g) in $CCl_4$ (300 mL) for 2 hours, cooled to room temperature, filtered and evaporated; 4-chloromethylthiazole can be prepared as described by Hsiao, C.-H. et al, Synthetic Communications, 20 (22), 3507–3417 (1990) and Caldwell, W and Fox, S. M. J. Am. Chem. Soc. 73, 2935 (1955). The resulting black mixture was stirred overnight and allowed to warm to room temperature. The material was concentrated, then diluted with water, and extracted using ethyl acetate. The organic layer was dried over anhydrous magnesium sulfate, filtered, and concentrated. Purification by silica gel flash column chromatography eluting with a solvent gradient of 30–65% ethyl acetate in hexane provided the title compound. (7.58 g, 20%).

FAB-MS calc. for $C_{17}H_{26}N_2O_4S$ 354; Found 355 (M+H)

Step B:

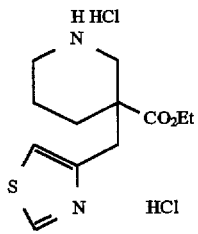

To a solution of the intermediate from the previous step (7.0 g, 19.8 mmol) in ethyl acetate (100 mL) at 0° C., was bubbled hydrogen chloride gas until saturation occurred. The reaction was stirred for 30 minutes, and then concentrated to remove the ethyl acetate to afford the product (5.3 g, 93%). $^1$H NMR ($CDCl_3$, 400 MHz) δ 9.67 (s, 1H), 7.75 (s, 1H), 4.34–4.15 (2 m, 2H), 3.67 (d, J=12.8 Hz, 1H), 3.34 (d, J=15 1H), 3.28 (d, J=12.5 Hz, 1H), 3.21 (d, J=15 Hz, 1H), 3.01 (dt, J=3.0, 2.5 Hz, 1H), 2.26 (br. d, J=13.7 Hz, 1H), 1.97–1.92 (m, 1H), 1.80 (dt, J=3.5, 13 Hz, 1H), 1.78–1.58 (m, 1H), 1.26 (t, J=7.2 Hz, 3H). FAB-MS calc. for $C_{12}H_{18}N_2O_2S$: 254; Found 255 (M+H)

Step C:

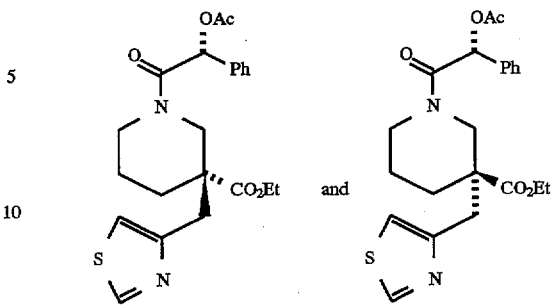

To a stirred solution of the intermediate (6 g, 18.67 mmol) prepared in Step B, (R)-(−)-(O)-acetyl mandelic acid (1 eq.), HOBT (1 eq.) and NMM (2 eq.) at 0° C. was added EDC (7.16 g, 37.34 mmol). The reaction mixture was stirred overnight during which time it was allowed to warm to room temperature. The solution was poured into brine and extracted with $CH_2Cl_2$. The organic layer was dried over $MgSO4$, evaporated and purified with a $SiO_2$ flash column eluting with 40–80% ethyl acetate in hexane to provided two enantiomerically pure compounds. The isomer which came out of the column first was designated as d1 (2.17 g, 30%) and the isomer which came out of the column second as d2 (0.87 g, 12%) and mixed fractions (700 mg). The stereochemistry assignment was made by NMR comparison of these compounds with the intermediates obtained in Example 8 Step A. The absolute stereochemistry of those intermediates was established by X-ray analysis. FAB-MS calc. for $C_{22}H_{26}N_2O_5S$: 430; Found 431(M+H) d1: $^1$H NMR ($CDCl_3$, 400 MHz) indicated the compound exists as a mixture of two conformers. δ 8.77, 8.65 (2 s, 1H), 7.46–7.34 (m, 5H), 7.07, 7.02 (2 s, 1H), 6.64, 6.23 (2s, 1H), 4.29 (br. d, J=13.9 Hz, 1/2H), 4.10–4.02 (m, 3/2H), 3.92–3.87 (m, 3/2H), 3.61 (d, J=13.5 Hz, 1/2H), 3.46 (d, J=14 Hz, 1/2H), 3.40–3.32 (m, 1/2H), 3.25–3.21 (m, 1/2H), 3.18 (d, J=14 Hz, 1/2H), 3.06 (d, J=14 Hz, 1/2H), 2.96 (d, J=14 Hz, 1/2H), 2.84 (d, J=14 Hz, 1/2H), 2.85–2.75 (br. m, 1/2H), 2.14,2.11 (2s, 3H), 1.90–1.82 (m, 11/2H), 1.80–1.75 (m, 1H), 1.61–1.55 (m, 1H), 1.50–1.40 (br. m, 1/2H), 1.14 (t, J=7 Hz, 3/2H), 1.03 (t, J=7 Hz, 3/2H). d2: $^1$H NMR ($CDCl_3$, 400 MHz) indicated the compound exists as a mixture of two conformers. δ 8.71, 8.68 (2d, J=1.8 Hz, 1H), 7.41–7.34 (m, 5H, 7.06, 6.83 (2 d, J=1.8 Hz, 1H), 6.41 6.20 (2s, 1H), 4.46 (br. d, J=13.4 Hz, 1/2H), 4.24–3.93 (m, 3H), 3.41 (d, J=13.5 Hz, 1/2H), 3.31–3.28 m, 1H), 3.13 (d, J=14.2 Hz, 1/2H), 3.04 (d, J=14.2 Hz, 1/2H), 3.04 (d, J=14.2 Hz, 1/2H), 2.92 (d, J=14 Hz, 1/2H), 2.73 (d, J=14 Hz, 1/2H), 2.54 (d, J=13.8 Hz, 1H), 2.30 (br. d, J=13 Hz), 2.15, 2.09 (2 s, 3H), 2.00–1.95 (m, 1/2H), 1.65–1.49 (m, 2H), 1.37 (dt, J=4, 12.8 Hz, 1/2H), 1.17–1.10 (m, 3H).

Step D:

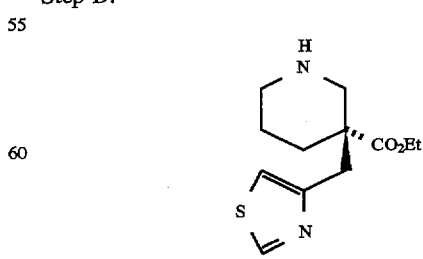

A solution of the intermediate d1 from the previous step (2.0 g, 4.65 mmol) concentrated hydrochloric acid (25 mL)

and ethanol (25 mL) was refluxed for 3 hours and was evaporated to dryness. The residue was neutralized by ammonium hydroxide and extracted by dichloromethane, and then was purified by SiO2 flash column eluting with 1:10:90 NH4OH:MeOH:CHCl3 to yield the product (0.72 g, 61%). $^1$H NMR (CD$_3$OD, 400 MHz) δ 8.88 (d, J=2 Hz, 1H), 7.21 (d, J=2 Hz, 1H), 4.20–4.07 (m, 2H), 3.28 (br. d, 1H), 3.06 (d, JAB=14 Hz, 1H), 2.97 (d, JBA=14 Hz, 1H), 2.92–2.80 (md, 1H), 2.61–2.57 (m, 2H), 2.21–2.16 (br. d, 1H), 1.66–1.40 (m, 3H), 1.20 (t, J=7.3 Hz, 3H).

FAB-MS calc. for $C_{12}H_{18}N_2O_2S$: 254; Found 255 (M+H)

Step E:

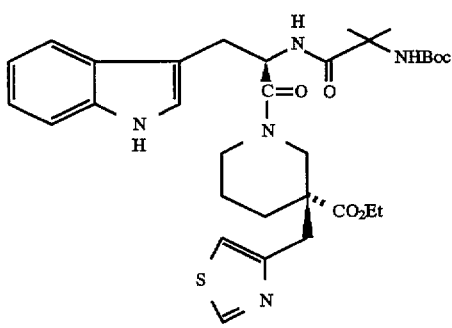

To a stirred solution of the intermediate from the previous step (163 mg, 0.642 mmol), Intermediate 1 (250 mg, 0.642 mmol) and HOBT (87 mg, 0.642 mmol) in dichlormethane (20 mL) was added EDC (247 mg, 1.28 mmol) at 0° C. The reaction mixture was stirred overnight and allowed to warm to room temperature. The solution was washed with saturated sodium chloride, dried over anhydrous magnesium sulfate; then filtered and concentrated. Purification by MPLC eluting with 60% ethyl acetate in hexane provided the desired compound (285 mg, 71%). FAB-MS calc. for $C_{32}H_{43}N_5O_6S$: 625; Found 626 (M+H); 526 (M±Boc(100)).

Step F:

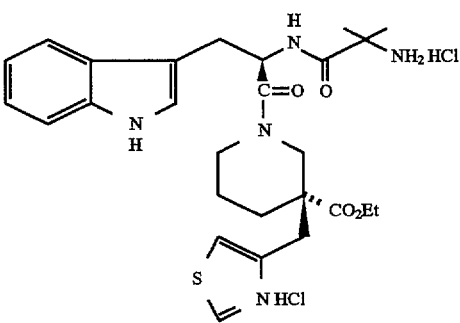

Hydrogen chloride gas was bubbled into a solution of the intermediate from the previous step (270 mg, 0.43 mmol) in ethyl acetate (10 mL) at 0° C. until it was saturated. The reaction was stirred for 30 minutes, and evaporated to remove the ethyl acetate to afford the product (226 mg, 93%). $^1$H NMR (CD3OD, 400 MHz): 9.90 (d, J=2.2Hz, 4/5H), 9.5 (d, J=2.2 Hz, 1/5H), 8.48 (d, J=7.15, 4/5H), 8.15 (d, 7.15, 1/5H), 7.70 (d, J=2.2 Hz, 4/5H), 7.68 (d, J=2.2, 1/5H), 7.55 (d, J=7.89 Hz, 1H), 7.27 (d, J=8.0 Hz, 1H), 7.06–6.95 (M, 1H), 3.94 (q, J=7.1 Hz, 2H), 3.94 (q, J=7.1 Hz, 2H), 2.37 (d, J=14.9, 1H), 1.90 (d, J=14.9, 1H), 1.60(s, 6H), 1.07 (t, J=7.1 Hz, 3H), FAB-MS calc. for $C_{27}H_{35}N_5O_4S$: 525; Found 526 (M+H)

EXAMPLE 27A

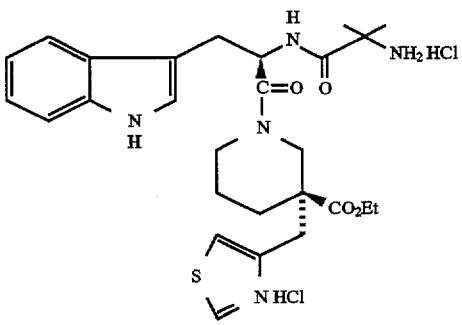

Following the same procedures as in Example 27 and using product d2 from step C, the title coumarine was prepped.

FAB-MS calc. for $C_{27}H_{35}N_5O_4S$: 525; Found 526 (M+H)

The additional intermediates shown in Table X were prepared with the corresponding alkylating agents according to the above established procedure as exemplified in Example 27 steps A and B. The final compounds were prepared according to Example 1 Steps D and E, using Intermediate 1.

TABLE X

| entry | Y | Intermediate MF FAB-MS(M + 1) | Product MF FAB-MS(M + 1) | isomer |
|---|---|---|---|---|
| 1 | H3C isoxazole-CH2— (3-methyl-5-methylisoxazol-4-yl)methyl | $C_{14}H_{22}N_2O_3$ 267 | $C_{29}H_{39}N_5O_5$ 538 | RS |
| 2 | 2-thiazolylmethyl | $C_{12}H_{18}N_2O_2S$ 255 | $C_{27}H_{35}N_5O_4S$ 526 | RS |
| 3 | 4-thiazolylmethyl | $C_{12}H_{18}N_2O_2S$ 255 | $C_{27}H_{35}N_5O_4S$ 526 | RS |
| 4 | 5-thiazolylmethyl | $C_{12}H_{18}N_2O_2S$ 255 | $C_{27}H_{35}N_5O_4S$ 526 | RS |
| 5 | (4-methyl-2-thiazolyl)methyl | $C_{13}H_{20}N_2O_2S$ 269 | $C_{28}H_{37}N_5O_4S$ 540 | RS |
| 6 | (2-methyl-4-thiazolyl)methyl | $C_{13}H_{20}N_2O_2S$ 269 | $C_{28}H_{37}N_5O_4S$ 540 | RS |
| 7 | (4-methyl-5-thiazolyl)methyl | $C_{13}H_{20}N_2O_2S$ 269 | $C_{28}H_{37}N_5O_4S$ 540 | RS |
| 8 | (5-methyl-4-thiazolyl)methyl | $C_{13}H_{20}N_2O_2S$ 269 | $C_{28}H_{37}N_5O_4S$ 540 | RS |

EXAMPLE 28

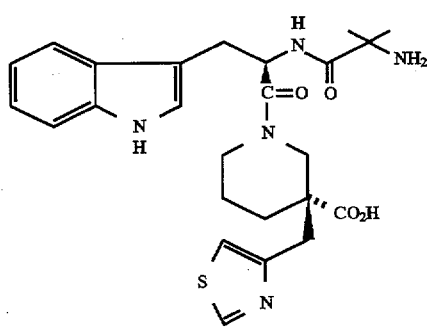

A solution of the final product of Example 27 (50 mg), NaOH (3N, 5 equiv.) in an mixture of ethanol/water (3:1, 5 mg) was stirred at 60° C. for two days. The reaction mixture as then evaporated in vacuo to remove ethanol. The residue was acidified by hydrochloric acid to pH=1 and evaporated to dryness. The white residue was purified by silica gel column eluting with 3/30/70 NH4OH/MeOH/CHCl3 to give the desired product (25 mg). FAB-MS calc. for $C_{25}H_{31}N_5O_4S$: 497; Found 498 (M+H)

EXAMPLE 29

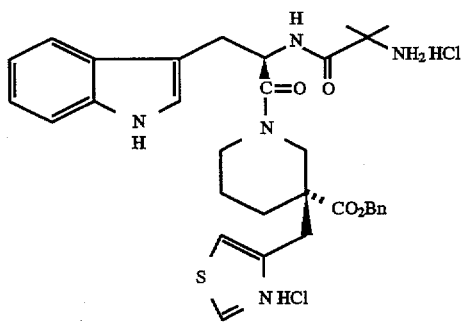

Step A:

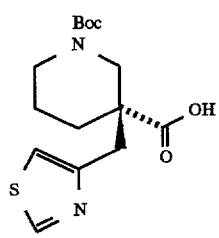

The less polar (d1) intermediate from Example 27 step C (1.5 g, 3.48 mmol) was refluxed for 2 hours in ethanol (10 ml) and 5N NaOH (3.5 mL). The mixture was then cooled to room temperature and slowly treated with 3N HCl to pH=11. To this stirred solution was added di-tert-butyl dicarbonate (1.52 g, 7 mmol) and stirred for two hours. The solution was acidified to pH 4 and then neutralized to pH 7 and extracted with ethyl acetate three times. The organic extracts were combined, dried, and concentrated to give white solid (810 mg).

Step B:

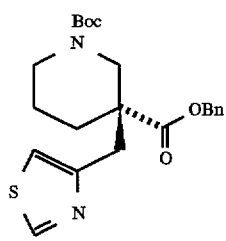

To a solution of the intermediate from the last step (800 mg), benzyl alcohol (1.27 mL), and DMAP (30 mg) in dichloromethane (40 mL), was added EDC (935 mg, 4.9 mmol). The mixture was stirred at room temperature for three days, and was poured into dilute NaHCO₃ solution. It was extracted with ethyl acetate three times, and dried over MgSO4. Evaporation and purification by a flash column eluting with 20–40% ethyl acetate in hexane gave the desired product.(145 mg).

Step C:

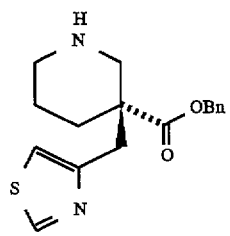

Prepared by the procedure described in Example 1, Step C from the intermediate from the previous step (140 mg) in ethyl acetate (20 mL) and HCl gas at 0° C. for 15 minutes. After evaporation, the residue was dissolved in dichloromethane and the solution was washed with NH4OH. The organic layer was dried evaporated to give the product.

Step D:

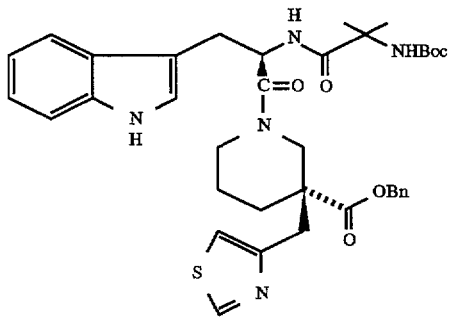

Prepared by the procedure described in Example 1, Step D from the intermediate prepared in the previous step (140 mg, 0.443 mmol), Intermediate 1 (172 mg, 0.443 mmol), HOBT (60 mg.) and EDC (170 mg). Purification by MPLC, eluting with 80% ethyl acetate in hexane, provided the intermediate (210 mg).

Step E:

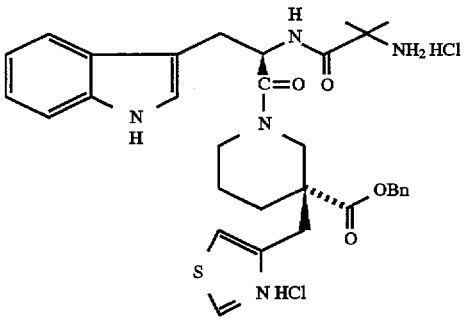

Prepared by the procedure described in Example 1, Step C from the intermediate from the previous step (12 mg, 0,018 mmol) and HCl gas in ethyl acetate (3 mL) at 0° C. for 10 minutes.

Likewise it is possible to prepare the compounds shown in Table Xa according to this example by reacting the intermediate from Example 29, Step A, with methylamine, ethylamine, ethanolamine, 3-aminopropanol or 2-(methylthio)ethylamine instead of benzyl alcohol in Step B, and using Intermediate 1 or Intermediate 3 in Step D.

TABLE Xa

| entry | R1 | X |
|---|---|---|
| 1 | indol-3-yl-CH₂— | —CONHCH₃ |
| 2 | phenyl-(CH₂)₃— | —CONHCH₃ |
| 3 | indol-3-yl-CH₂— | —CONHCH₂CH₃ |
| 4 | phenyl-(CH₂)₃— | —CONHCH₂CH₃ |

TABLE Xa-continued

| entry | R1 | X |
|---|---|---|
| 5 | indole-CH₂— | —CONHCH₂CH₂OH |
| 6 | phenyl-(CH₂)₃— | —CONHCH₂CH₂OH |
| 7 | indole-CH₂— | —CONH(CH₂)₃OH |
| 8 | phenyl-(CH₂)₃— | —CONH(CH₂)₃OH |
| 9 | indole-CH₂— | —CONH(CH₂)₂SCH₃ |
| 10 | phenyl-(CH₂)₃— | —CONH(CH₂)₂SCH₃ |

EXAMPLE 30

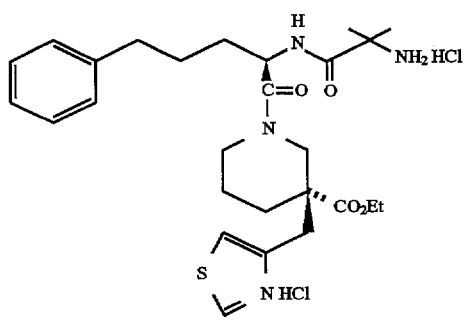

Step A:

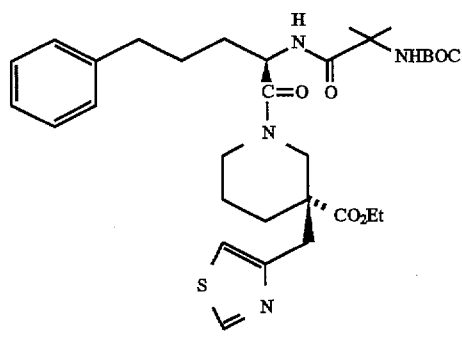

Prepared by the procedure described in Example 1, Step D from the intermediate prepared in Example 27 Step D (134 mg, 0.528 mmol), Intermediate 3 (200 mg, 0.528 mmol), HOBT (71 mg, 1 eq.), and EDC (200 mg, 2 eq.). Purification by MPLC, eluting with 60% ethyl acetate in hexane provided the intermediate (160 mg, 49%) FAB-MS calc. for $C_{32}H_{46}N_4O_6S$: 606; Found 607 (M+H)

Step B:

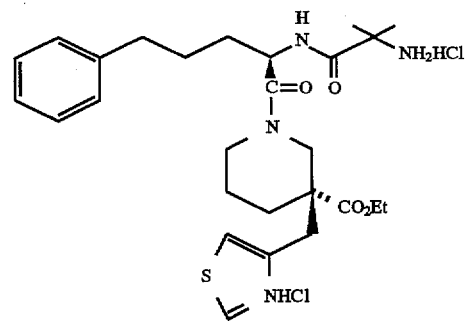

Prepared by the procedure described in Example 1, Step C from the intermediate from the previous step (155 mg, 0.252 mmol) and HCl gas in ethyl acetate (5 mL) at 0° C. for 10 minutes (142 mg, 96%). FAB-MS calc. for $C_{27}H_{38}N_4O_4S$: 506; Found 507 (M+H)

EXAMPLE 31

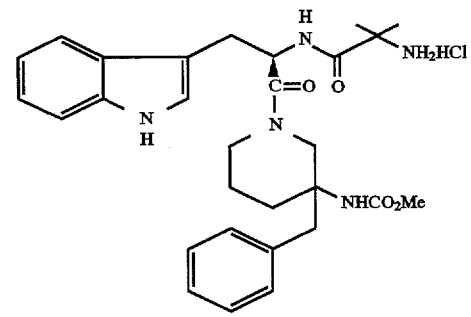

Step A:

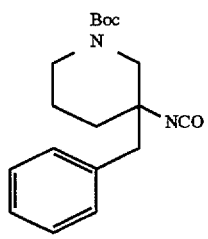

To a stirred solution of the product from example 15 step A (2.00 g, 6..26 mmol) and DMF (3 drops) in benzene (20 mL) at 0° C., was added oxalyl chloride (0.89 g, 6.89 mmol) slowly. The reaction was stirred at 0° C. for 10 minutes and another 20 minutes at room temperature. The reaction mixture was evaporated in vacuo to give the acyl chloride and it was used for the next reaction without further purification. To a stirred solution of the residue in acetone (20 mL) at 5° C., was added sodium azide (1.22 g, 18.8 mmol) in water (3 mL) and the resulting mixture was stirred at room temperature for 30 minutes. The reaction mixture was evaporated to remove acetone, and was diluted with water and extracted with ether. The ether extracts were combined and dried over MgSO4. Filtration and evaporation gave the crude azide and it was used without further purification. The resulting material was dissolved in toluene (70 mL) and was refluxed overnight to give the isocyanate toluene solution. FAB-MS calc. for $C_{18}H_{24}N_2O_3$: 316; Found 217 (M+H-BOC(100)).

Step B:

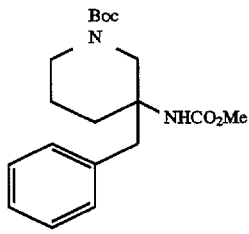

A solution of methanol (5 mL) and the solution obtained from the last step (15 mL out of 70 mL total, 1.3 mmol) was refluxed overnight. The reaction mixture was evaporated to give a white solid (331 mg). FAB-MS calc. for $C_{19}H_{28}N_2O_4$: 348; Found 349 (M+H).

Step C:

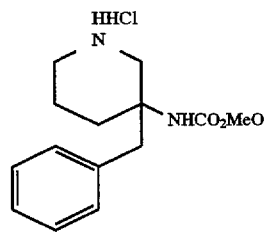

To a solution of the intermediate from the previous step (271 mg) in ethyl acetate (15 mL) at 0° C., was bubbled hydrogen chloride gas until saturation occurred. The reaction was stirred for 30 minutes, until TLC analysis indicated that the reaction was complete. The solution was then concentrated to remove the ethyl acetate to afford the product (284 mg). FAB-MS calc. for $C_{14}H_{20}N_2O_2$: 248; Found 249 (M+H)

Step D:

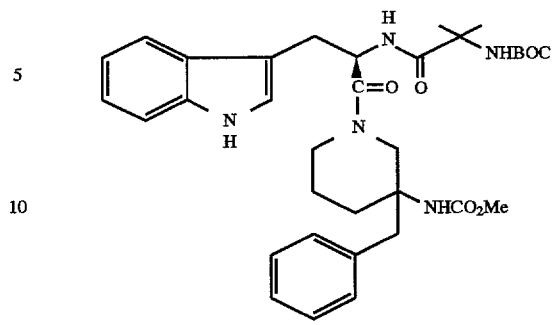

Prepared by the procedure described in Example 1, Step D from the intermediate prepared in the previous step (0.284 g, 1 mmol), Intermediate 1 (0.388 g, 1 mmol), HOBT (1 eq.), N-methyl morpholine (1 eq.), and EDC (1.5 eq.). Purification by MPLC, eluting with 60% ethyl acetate in hexane, provided the intermediate (0.35 g).

FAB-MS calc. for $C_{34}H_{45}N_5O_6$: 619; Found 620 (M+H)

Step E:

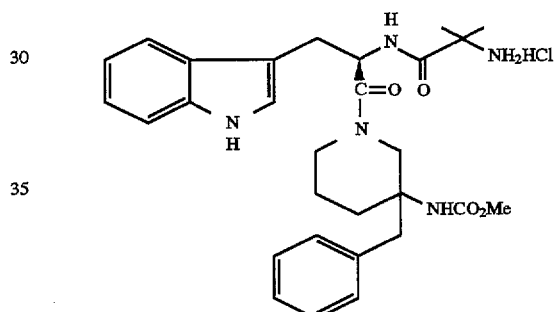

To a solution of the intermediate from the previous step (200 mg, mmol) in ethyl acetate (10 mL) at 0° C., was bubbled hydrogen chloride gas until saturation occurred. The reaction was stirred for 30 minutes, and then concentrated to remove the ethyl acetate to afford the product (158mg). FAB-MS calc. for $C_{29}H_{37}N_5O_4$: 519; Found 520 (M+H)

EXAMPLE 32

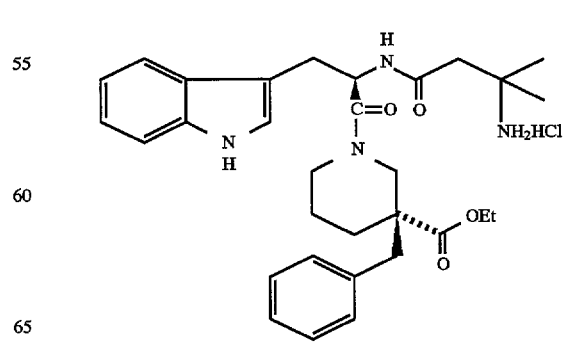

Step A:

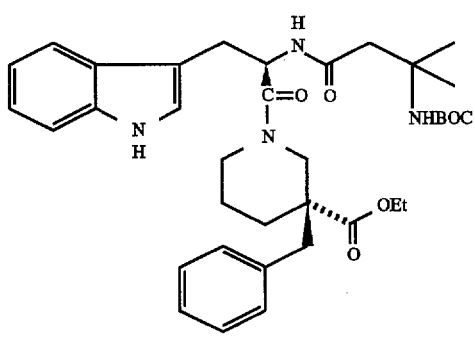

To a stirred suspension of the intermediate obtained in Example 2, step C (HCl salt, 2.51 g, 5.34 mmol), N-Boc-β-amino-β-Me-butyric acid (1.16 g, 1 equiv.), NMM (0.6 mL, 1 equiv.) and DMAP (33 mg,0.05 equiv.) in dichloromethane (30 mL), was added EDC (1.55 g, 1.5 equiv.) in several portions. The reaction mixture quickly became clear and it was stirred for 3 hours and was worked up by diluting it with dichloromethane and washing with 3N HCl, brine, and saturated sodium bicarbonate solution. The organic layer was dried over MgSO4, evaporated and purified by silica gel column chromatography, eluting with 60% ethyl acetate in hexane to give the desired compound (3.40 g, 100%). FAB-MS calc. for $C_{36}H_{48}N_4O_6$: 632; Found 633 (M+H)

Step B:

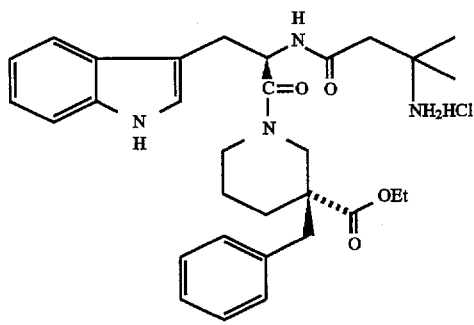

To a stirred solution of the intermediate from the previous step (3.28 g, 5.18 mmol) in ethyl acetate (30 mL) at 0° C., was bubbled HCl gas until it was saturated. The reaction was stirred for 10 minutes, and was evaporated to dryness. The residue was dissolved in dichloromethane, and to which ether was added. The solid which formed was collected by filtration, and it was air dried and left under high vacuum overnight to give the product (2.44 g, 83%).

FAB-MS calc. for $C_{31}H_{40}N_4O_4$: 532; Found 533 (M+H)

Similarly the following compounds were prepared according to the same procedure as described above, but using different Boc protected amino acids which were subsequently deprotected as described above.

TABLE XI

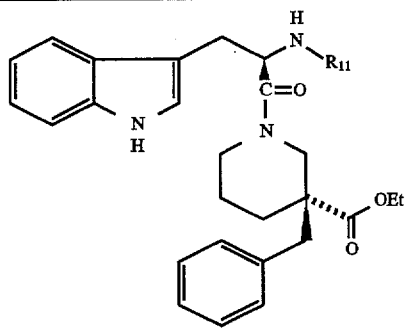

| entry | $R_{11}$ | MF FAB-MS(M + 1) |
|---|---|---|
| 1 | D-Ala— | $C_{29}H_{36}N_4O_4$ 505 |
| 2 | L-Ala— | $C_{29}H_{36}N_4O_4$ 505 |
| 3 | β-Ala— | $C_{29}H_{36}N_4O_4$ 505 |
| 4 | DL-α-Me—Ser— | $C_{30}H_{38}N_4O_5$ 535 |
| 5 | ![cyclopropyl-NH2 ketone] | $C_{30}H_{36}N_4O_4$ 517 |
| 6 | ![cyclohexyl-NH2 ketone] | $C_{33}H_{42}N_4O_4$ 559 |
| 7 | D-Pro— | $C_{31}H_{38}N_4O_4$ 531 |
| 8 | N—Me—Aib— | $C_{31}H_{40}N_4O_4$ 533 |
| 9 | ![piperidinyl ketone] | $C_{32}H_{40}N_4O_4$ 545 |
| 10 | ![methylpiperidinyl ketone] | $C_{33}H_{42}N_4O_4$ 559 |
| 11 | ![quinuclidinyl ketone] | $C_{34}H_{42}N_4O_4$ 571 |
| 12 | L-Pro— | $C_{31}H_{38}N_4O_4$ 531 |
| 13 | ![piperidinyl ketone] | $C_{32}H_{40}N_4O_4$ 545 |

TABLE XI-continued

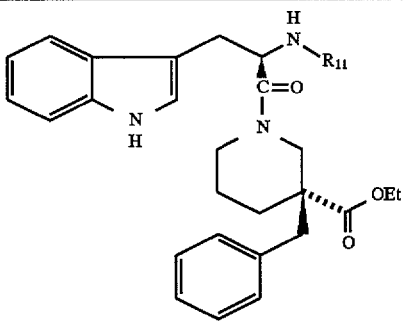

| entry | R$_{11}$ | MF FAB-MS(M + 1) |
|---|---|---|
| 14 | (3-methylpiperidin-3-yl carbonyl group) | C$_{33}$H$_{42}$N$_4$O$_4$ 559 |
| 15 | (2-amino-2-methylpropanoyl) | C$_{31}$H$_{40}$N$_4$O$_4$ 533 |
| 16 | (1-aminocyclopentanecarbonyl) | C$_{32}$H$_{40}$N$_4$O$_4$ 545 |
| 17 | (imidazolyl-methylpropanoyl) | C$_{29}$H$_{32}$N$_6$O$_4$ 529 |
| 18 | (pyridyl-methylpropenoyl) | C$_{30}$H$_{33}$N$_5$O$_4$ 528 |
| 19 | Gly— | C$_{28}$H$_{34}$N$_4$O$_4$ 491 |
| 20 | D-Phe— | C$_{35}$H$_{40}$N$_4$O$_4$ 581 |
| 21 | L-Phe— | C$_{35}$H$_{40}$N$_4$O$_4$ 581 |
| 22 | D-Val— | C$_{31}$H$_{40}$N$_4$O$_4$ 533 |
| 23 | L-Val— | C$_{31}$H$_{40}$N$_4$O$_4$ 533 |
| 24 | D-Leu— | C$_{32}$H$_{42}$N$_4$O$_4$ 547 |
| 25 | L-Leu— | C$_{32}$H$_{42}$N$_4$O$_4$ 547 |
| 26 | D-Ile— | C$_{32}$H$_{42}$N$_4$O$_4$ 547 |
| 27 | L-Ile— | C$_{32}$H$_{42}$N$_4$O$_4$ 547 |
| 28 | D-Nle— | C$_{32}$H$_{42}$N$_4$O$_4$ 547 |
| 29 | L-Nle— | C$_{32}$H$_{42}$N$_4$O$_4$ 547 |

EXAMPLE 33

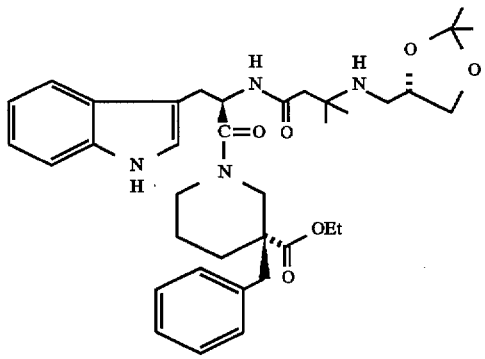

To a stirred solution of the product from Example 32 (808 mg, 1.42 mmol), (R)-glyceraldehyde acetonide (923 mg, 5 equiv.) and sodium acetate (582 mg, 5 equiv.) in methanol (15 mL) at 0° C., was slowly added sodium cyanoborohydride (134 mg, 1.5 equiv.) and the resulting mixture was stirred at room temperate overnight. The mixture was evaporated to remove methanol and partitioned between sodium bicarbonate solution and dichloromethane. The organic layer was separated and the aqueous layer was extacted two more times with dichloromethane. The combined organic extacts were dried over magnesium sulfate and purified by a silica gel column, eluting with 5–10% methanol in dichloromethane to give the product (835 mg, 91%) FAB-MS calc. for C$_{37}$H$_{50}$N$_4$O$_6$: 646; Found 647 (M+H)

EXAMPLE 34

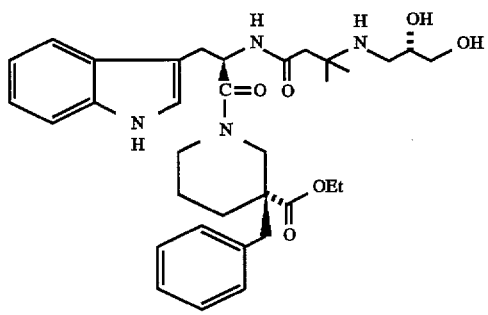

To a solution of the product from Example 33 (367 mg, 0.566 mmol) in methanol (10 mL) was added hydrochloric acid (3N, 1 mL) and the resulting mixture was stirred at room temperature for one day. The reaction mixture was evaporated in vacuo, and toluene was added and evaporated in vacuo again to remove the residual water to give the product (350 mg, 99%). FAB-MS calc. for C$_{34}$H$_{46}$N$_4$O$_6$: 606; Found 607 (M+H)

EXAMPLE 35

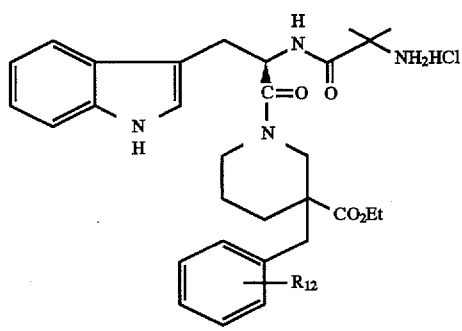

Additional benzyl substituted intermediates and products as shown in Table XII were prepared according to procedures described in Example 1 Steps A and B using appropriately substituted benzyl halides in the alkylation step. Functional groups changes as needed were made at the intermediate Step B stage to convert as needed cyano groups to carboxamides, esters and tetrazoles, nitro groups to amines and acetylamines and esters to acids (at step D) according to standard literature procedures.

TABLE XII
ADDITIONAL EXAMPLES

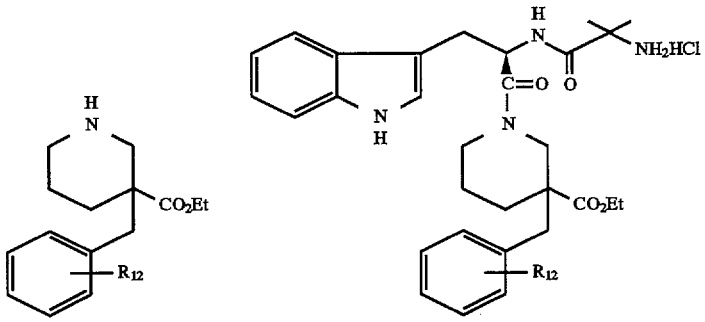

| entry | $R_{12}$ | Intermediate MF FAB-MS(M + 1) | Product MF FAB-MS(M + 1) | isomer |
|---|---|---|---|---|
| 1 | o-cyano- | $C_{16}H_{20}N_2O_2$ 273 | $C_{31}H_{37}N_5O_4$ 544 | d1 d2 |
| 2 | m-cyano- | $C_{16}H_{20}N_2O_2$ 273 | $C_{31}H_{37}N_5O_4$ 544 | d1 d2 |
| 3 | p-cyano- | $C_{16}H_{20}N_2O_2$ 273 | $C_{31}H_{37}N_5O_4$ 544 | d1 d2 |
| 4 | p-$NH_2OC-$ | $C_{16}H_{22}N_2O_3$ 291 | $C_{31}H_{37}N_5O_4$ 562 | RS |
| 5 | p-$EtO_2C-$ | $C_{18}H_{25}NO_4$ 320 | $C_{33}H_{42}N_4O_6$ 591 | d1 d2 |
| 6 | p-$HO_2C-$ |  | $C_{31}H_{38}N_4O_6$ 563 | d1 d2 |
| 7 | p-(1H-tetrazole-5-yl) | $C_{16}H_{21}N_5O_2$ 316 | $C_{31}H_{38}N_8O_4$ 587 | RS |
| 8 | m-$NH_2OC-$ | $C_{16}H_{22}N_2O_3$ 291 | $C_{31}H_{37}N_5O_4$ 562 | RS |
| 9 | m-$EtO_2C-$ | $C_{18}H_{25}NO_4$ 320 | $C_{33}H_{42}N_4O_6$ 591 | d1 d2 |
| 10 | m-$HO_2C-$ |  | $C_{31}H_{38}N_4O_6$ 563 | d1 d2 |
| 11 | m-(1H-tetrazole-5-yl) | $C_{16}H_{21}N_5O_2$ 316 | $C_{31}H_{38}N_8O_4$ 587 | RS |
| 12 | o-$NH_2OC-$ | $C_{16}H_{22}N_2O_3$ 291 | $C_{31}H_{37}N_5O_4$ 562 | RS |
| 13 | o-$EtO_2C-$ | $C_{18}H_{25}NO_4$ 320 | $C_{33}H_{42}N_4O_6$ 591 | d1 d2 |
| 14 | o-$HO_2C-$ |  | $C_{31}H_{38}N_4O_6$ 563 | d1 d2 |
| 15 | o-(1H-tetrazole-5-yl | $C_{16}H_{21}N_5O_2$ 316 | $C_{31}H_{38}N_8O_4$ 587 | RS |
| 16 | p-AcNH- | $C_{17}H_{24}N_2O_3$ 305 | $C_{32}H_{41}N_5O_5$ 576 | RS |
| 17 | m-AcNH- | $C_{17}H_{24}N_2O_3$ 305 | $C_{32}H_{41}N_5O_5$ 576 | RS |

EXAMPLE 36

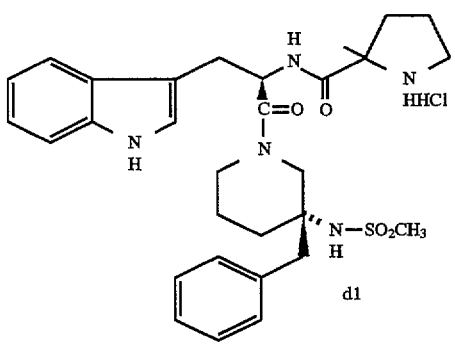

and

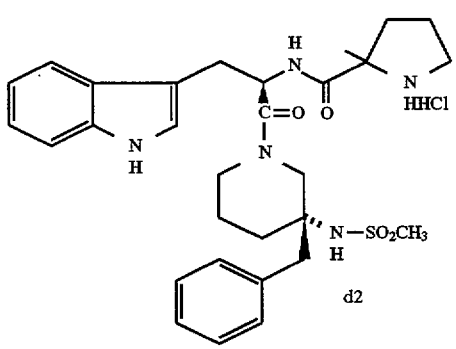

Step A:

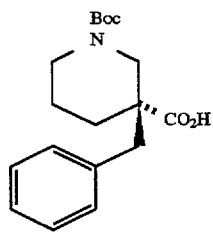

A solution of the S- isomer intermediate of Step A of Example 2 (as the L-tartaric acid salt, 20 g, 50 mmol) and NaOH (5N, 80 mL) in ethanol (80 mL) was heated to 60° C. for one day. The resulting solution was cooled to room temperature and to which was slowly added di-t-butyl dicarbonate (12.5 g, 58 mmol). The reaction mixture was stirred for one hour, and evaporated in vacuo to remove most of the ethanol. Ice was added to the reaction mixture, and the solution was acidified to pH-4 with 3N hydrochloric acid. The white solid formed was filtered and dried in vacuum oven to give the desired acid as a white solid.

Step B:

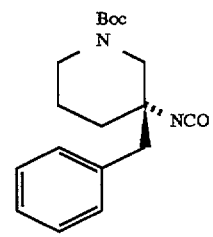

A solution of the acid obtained from the previous step (6 g, 18.8 mmol), diphenylphosphoryl azide (DPPA, 5.1 mL, 23.5 mmol) and triethyl amine (3.28 mL, 23.5 mmol) in toluene (75 mL) was refluxed for 1 hour. The reaction mixture was cooled to room temperature and the resulting isocyanate solution was used as is without further treatment.

Step C:

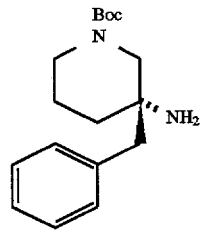

A solution of the isocyanate in toluene from the previous step (50 mL out of 75 mL total, 12.5 mmol) and benzyl alcohol (2.6 mL, 25 mmol) was stirred at room temperature overnight and then refluxed for two hours. The solution was evaporated and purified by flash column eluting with 20–100% ethyl acetate in hexane to give the CBZ protected amine. A solution of the CBZ protected amine (3 g, 7.1 mmol) and palladium on carbon (10%, 300 mg) was stirred under a H2 balloon overnight. The catalyst was filtered off through a pad of celite and the amine was obtained in quantitative yield after removal of the ethanol. FAB-MS calc. for $C_{17}H_{26}N_2O_2$: 290; Found 291 (M+H)

Step D:

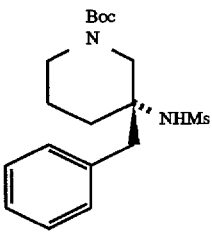

To a solution of the intermediate amine from the previous step (350 mg, 1.2 mmol) and NMM (0.2 mL, 1.57 mmol) in dichloromethane (15 mL) was added methanesulfonyl chloride (122 mL, 1.57 mmol) at 0° C. The reaction was stirred for 25 minutes and TLC analysis indicated that the reaction was complete. The reaction mixture was poured in to dilute HCl solution and extracted with dichloromethane. The organic layer was washed with brine, dried over MgSO4, filtered and evaporated. The residue was purified by MPLC eluting with 70% ethyl acetate in hexane to give the mesylate material (258 mg, 59%).

Step D:

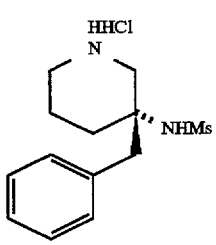

To a solution of the intermediate from the previous step (258 mg, 0.7 mmol) in ethyl acetate (10 mL) at 0° C., was bubbled HCl gas until it was saturated. The reaction mixture was stirred at 0° C. for 15 minutes and was evaporated to remove excess HCl and ethyl acetate to give the salt as white foam (209 mg, 98%)

Using procedures essentially as described above, the following intermediates were prepared.

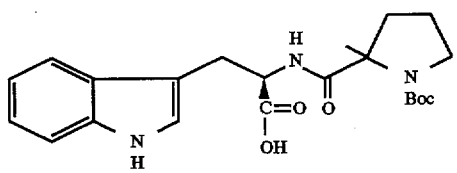

| entry | X | acylating reagent | MF FAB-MS(M + 1) |
|---|---|---|---|
| 1 | NHCONMe$_2$ | dimethylcarbamyl chloride | C$_{15}$H$_{23}$N$_3$O 262 |
| 2 | NHCOCHMe$_2$ | isobutyryl chloride | C$_{16}$H$_{26}$N$_2$O 261 |

Step D:

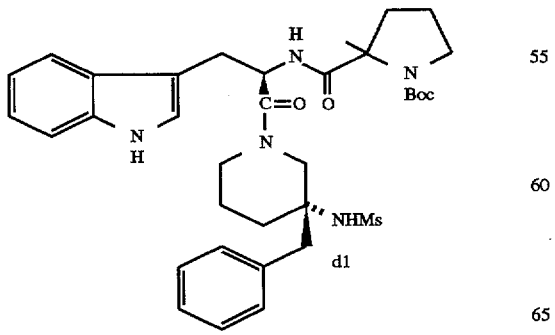

To a solution of the D-tryptophan benzyl ester (1.5 g, 4.5 mmol), HOBT (0.61 g, 1 equiv.) and N-BOC-α-methyl proline (1.04 g, 1 equiv.) in 50 mL of dichloromethane was added EDC (1.14 g, 1.3 equiv.) in several portions at 0° C. After stirring at room temperature overnight, the reaction mixture was poured into 200 mL of water and the organic layer was separated. The organic solution was washed with brine, and with a brine and saturated sodium bicarbonate solution, dried over anhydrous magnesium sulfate, filtered and concentrated to give a thick oil, which was purified by flash chromatography eluting with 10–40% ethyl acetate in hexane to give the benzyl ester (1.77 g).

A solution of the benzyl ester from above (1.77 g) in 500 mL of ethanol was stirred at room temperature under a H2 balloon for 20 minutes in the presence of 10% palladium on carbon (0.17 g). The catalyst was filtered off through a pad of celite and washed with ethyl acetate. The solution was concentrated to give the acid Boc-α-Me-Pro-D-TrpOH as a slightly pink foam (1.33 g).

Step E:

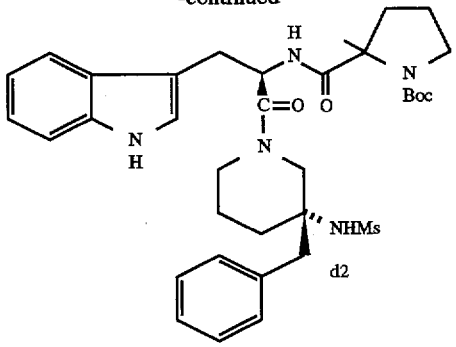

To a solution of the intermediate prepared in Step D of this example (110 mg, 0.36 mmol), and Boc-α-Me-Pro-D-TrpOH (1 eq.), HOBT (1 eq.), and N-methyl morpholine (1 eq.) in dichloromethane was added EDC (1.5 eq.) at 0° C. The reaction mixture was stirred at 0° C. overnight. The solution was washed with saturated sodium chloride, dried over anhydrous magnesium sulfate; then filtered and concentrated. Purification by MPLC separated the two diastereomers. The compound which came out first from the column was designated as d1; and the compound which came out of the column second was designated as d2

Step F:

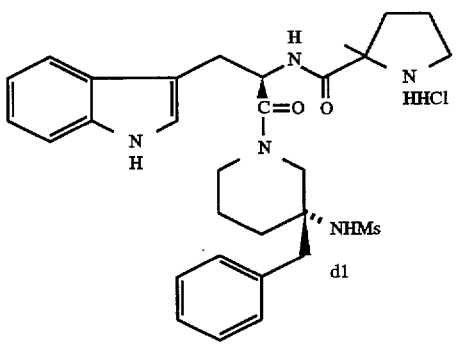

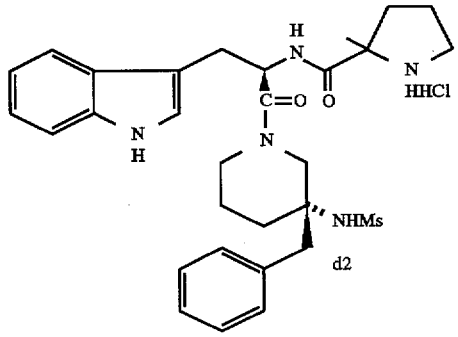

To a solution of the intermediates from the previous step (d 1 and d2) in ethyl acetate (5 mL each) at 0° C., was bubbled HCl gas until saturated. The reaction mixtures were stirred at 0° C. for 15 minutes and were evaporated to remove excess HCl and ethyl acetate to give the salts as white foams. FAB-MS for both d1 and d2: calc. for C$_{30}$H39N5O4S: Found 566 (M+H)

EXAMPLE 37

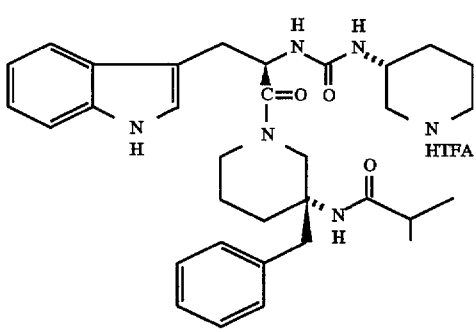

Step A:

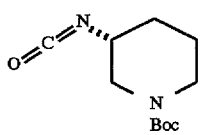

A solution of the N-Boc-(R)-isonipecotic acid (1.3 g, 5.9 mmol), DPPA (1.6 mL, 7.41 mmol) and triethylamine (1.03, 7.41 mmol) in toluene (23 mL) was refluxed for 1 hour. The reaction mixture was cooled to room temperature and the isocyanate solution was used as is without purification.

Step B:

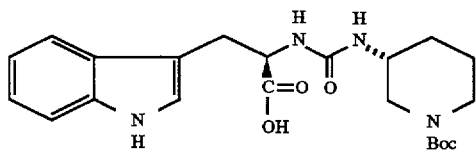

To a solution of the D-tryptophan benzyl ester (1.96 g, 5.93 mmol) and NMM (0.652 mL, 5.93 mmol) in dichloromethane (40 mL), was added the isocyanate obtained in Step A (5.93 mmol). After stirring at room temperature for two hours, the reaction mixture was washed with brine, and with a brine and saturated sodium bicarbonate solution, dried over anhydrous magnesium sulfate, filtered and concentrated to give a thick oil, which was purified by flash chromatography eluting with 80% ethyl acetate in hexane to give the benzyl ester (2.81 g).

A solution of the benzyl ester from above (2.6 g) in 50 mL of ethanol was stirred at RT under a $H_2$ balloon for 20 minutes in the presence of 10% palladium on carbon (0.26 g). The catalyst was filtered off through a pad of celite and washed with ethyl acetate. The solution was evaporated to give the acid as a slightly pink foam (2.05 g).

Step C:

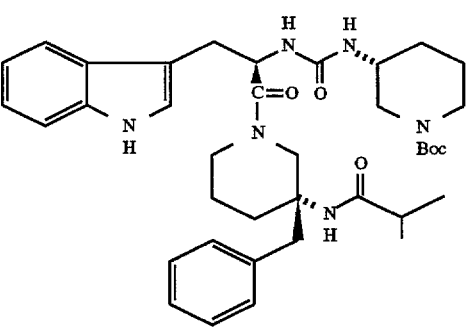

To a solution of an intermediate prepared in Step D (entry 2) of Example 36 (69 mg, 0.23 mmol), and the intermediate prepared from the previous step (100 mg), HOBT (31 mg), and N-methyl morpholine (26 gL) in dichloromethane was added EDC (89 mg) at 0° C. The reaction mixture was stirred at 0° C. overnight. The solution was washed with saturated sodium chloride, dried over anhydrous magnesium sulfate; then filtered and concentrated. Purification by MPLC gave the desired Boc intermediate (120 mg).

Step E:

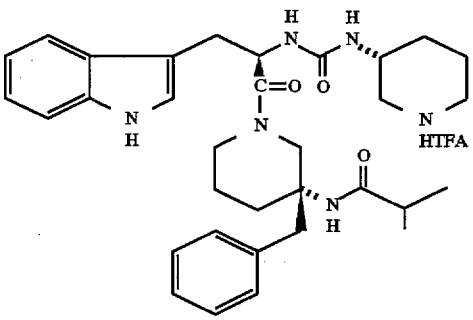

To a solution of the intermediate from the previous step (40 mg) in dichloromethane (2 mL) was added TFA (2 mL). The reaction mixture was stirred room temperature for 1 hour and was evaporated to give the salts as white foam. FAB-MS calc. for $C_{33}H_{44}N_6O_3$: 572; Found 573 (M+H).

EXAMPLE 38

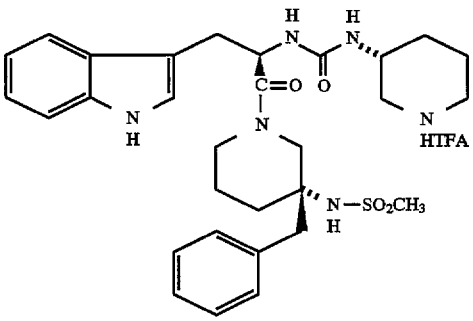

and

-continued

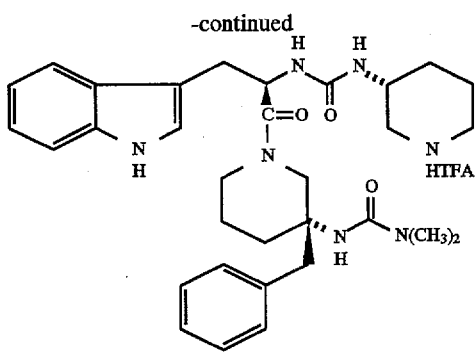

Using procedures essentially as described in Example 37, the following compounds were prepared from the intermediates listed in Example 36, Step D.

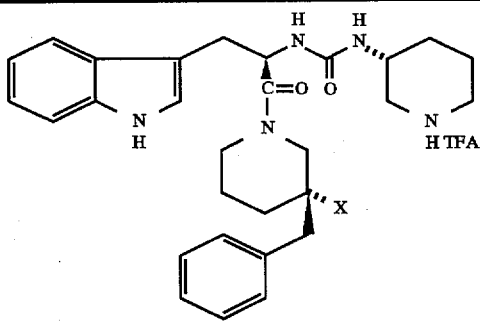

| entry | X | MF FAB-MS(M + 1) |
|---|---|---|
| 1 | NHMs | $C_{30}H_{40}N_6O_4S$ 581 |
| 2 | NHCONMe2 | $C_{32}H_{43}N_7O_3$ 574 |

EXAMPLE 39

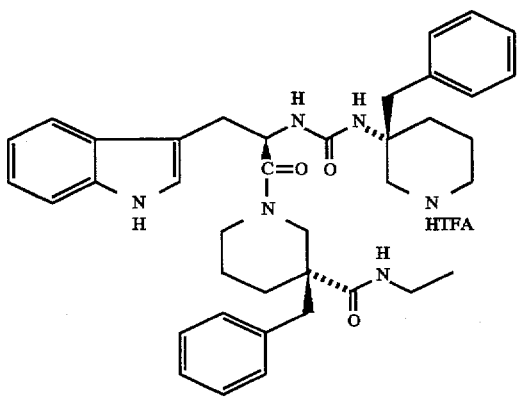

Step A:

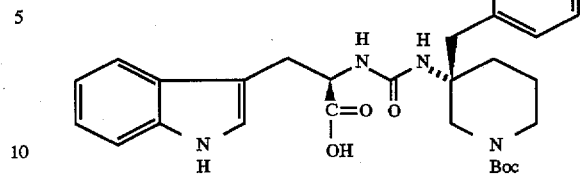

To a solution of the D-tryptophan benzyl ester (1.5 g, 4.53 mmol) and NMM (0.5 mL, 4.53 mmol) in dichloromethane (40 mL), was added the isocyanate obtained in Example 36 step B (4.53 mmol). After stirring at room temperature overnight, the reaction mixture was washed with brine, and with a brine and saturated sodium bicarbonate solution, dried over anhydrous magnesium sulfate, filtered and concentrated to give a thick oil, which was purified by flash chromatography eluting with 60% ethyl acetate in hexane to give the benzyl ester (2.3 g, 91%).

A solution of the benzyl ester from above (2.10 g) in 75 mL of ethanol was stirred at RT under a $H_2$ balloon overnight in the presence of 10% palladium on carbon (0.26 g). The catalyst was filtered off through a pad of celite and washed with ethyl acetate. The filtrate was concentrated to give the acid as a slightly pink foam (1.6 g, 90%).

Step B:

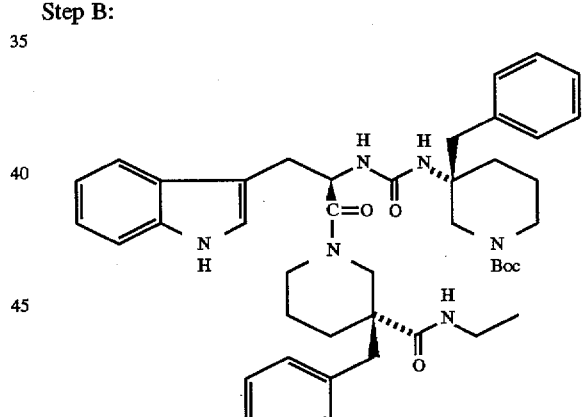

To a solution of the intermediate prepared in Step C of Example 17 (46.1 mg, 0.163 mmol), and the intermediate prepared from the previous step (85 mg), HOBT (23 mg), and N-methyl morpholine (18 µL) in dichloromethane was added EDC (63 mg) at 0° C. The reaction mixture was stirred at 0° C. overnight. The solution was washed with saturated sodium chloride, dried over anhydrous magnesium sulfate; then filtered and concentrated. Purification by MPLC eluting with 70% ethyl acetate in hexane gave the desired Boc intermediate (69 mg).

Step E:

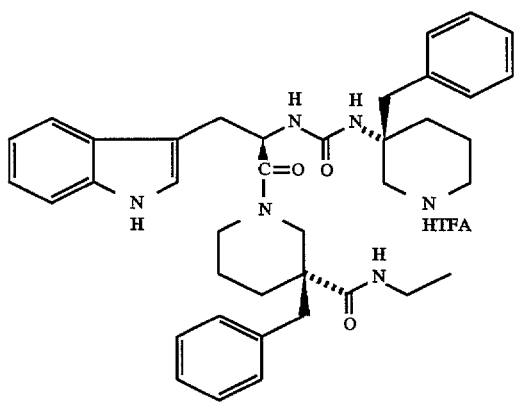

To a solution of the intermediate from the previous step (69 mg) in dichloromethane (2 mL) was added TFA (2 mL). The reaction mixture was stirred room temperature for 1 hour and was evaporated to give the salts as white foam. FAB-MS cat. for C39H48N6O3: 648; Found 649 (M+H)

EXAMPLE 40

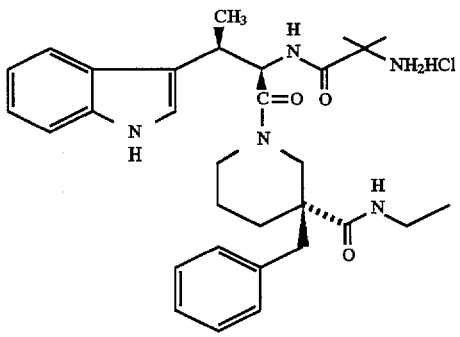

Step A:

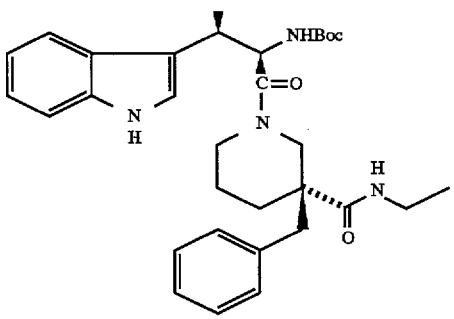

To a solution of the intermediate prepared in Step C of Example 17 (444 mg, 1.57 mmol), and Boc-(2R,3R)-β-Me-TrpOH (500 mg, 1.57 mmol), HOBT (212 mg, 1.57 mmol), and N-methyl morpholine (172 μL, 1.57 mmol) in dichloromethane was added EDC (602 mg, 3.14 mmol) at 0° C. The reaction mixture was stirred at 0° C. overnight. The solution was washed with saturated sodium chloride, dried over anhydrous magnesium sulfate; then filtered and concentrated. Purification by MPLC eluting with 80% ethyl acetate in hexane gave the desired Boc intermediate (1.8 g).

Step B:

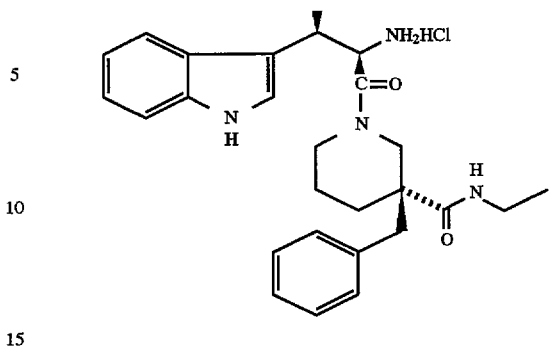

To a solution of the intermediate from the previous step (1.8 g, 3.29 mmol) in ethyl acetate (12 mL) at 0° C., was bubbled HCl gas until saturated. The reaction mixture was stirred at 0° C. for 15 minutes and was evaporated to remove excess HCl and ethyl acetate to give the salts as white solid (1.34 g). FAB-MS calc. for C27H34N4O2: 446; Found 447 (M+H).

Step C:

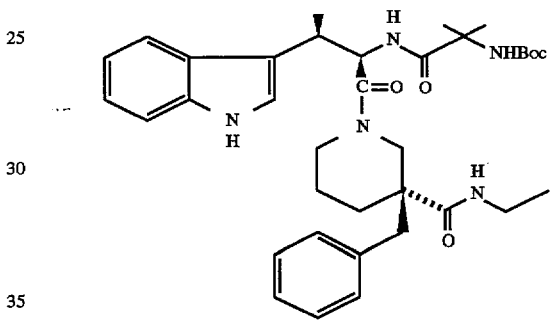

To a solution of the intermediate from the previous step (100 mg, 0.207 mmol), and Boc-AibOH (42 mg, 0.207 mmol), HOBT (28 mg, 0.207 mmol), and N-methyl morpholine (23 μL, 0.207 mmol) in dichloromethane was added EDC (80 mg, 0.414 mmol) at 0° C. The reaction mixture was stirred at 0° C. overnight. The solution was washed with saturated sodium chloride, dried over anhydrous magnesium sulfate; then filtered and concentrated. Purification by MPLC eluting with 2% methanol in ethyl acetate gave the desired Boc intermediate (110 mg).

Step D:

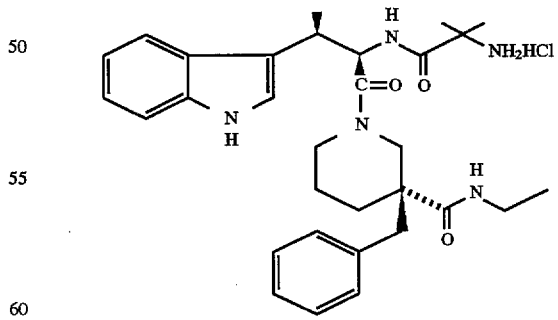

To a solution of the intermediate from the previous step (110 mg) in ethyl acetate (5 mL) at 0° C., was bubbled HCl gas until saturated. The reaction mixture was stirred at 0° C. for 15 minutes and was evaporated to remove excess HCl and ethyl acetate to give the salts as white solid. FAB-MS calc. for C31H41N5O3: 531; Found 532 (M+H).

EXAMPLE 41
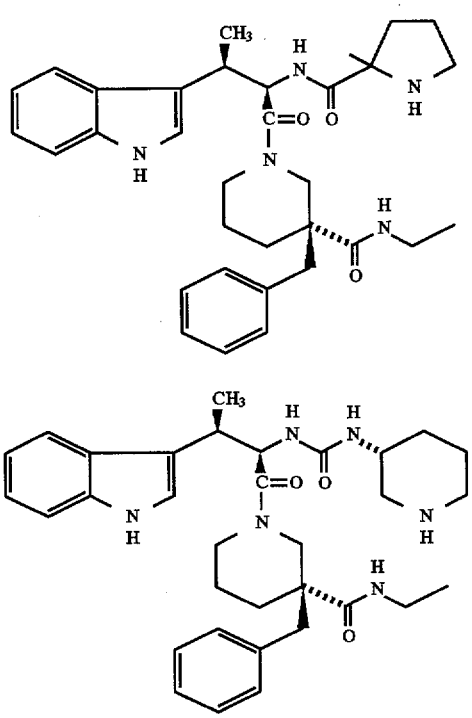
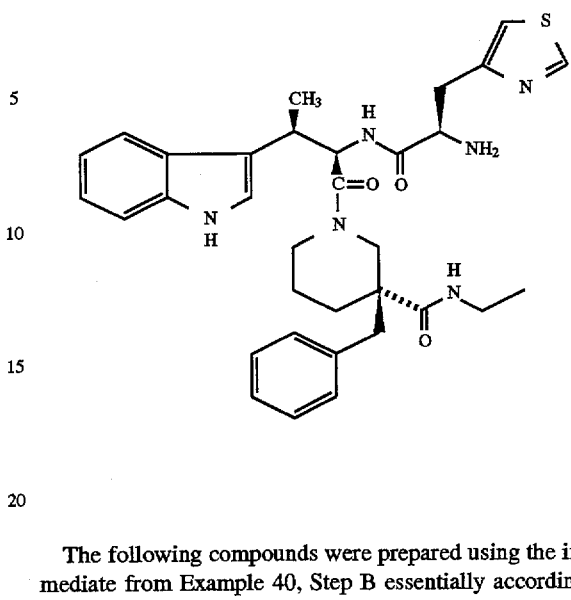
The following compounds were prepared using the intermediate from Example 40, Step B essentially according to the above procedures.
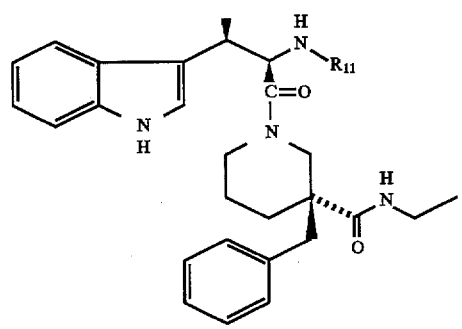
| entry | R$_{11}$ | acylation reagent | isomer | MF FAB-MS(M + 1) |
|---|---|---|---|---|
| 1 | (2-methylpyrrolidine-2-carbonyl group) | Boc—α-Me—Pro—OH | d1 + d2 | C33H43N5O3 Calc.: 557 Found: 558 |
| 2 | (3-piperidinylcarbamoyl group) | (3-isocyanato-N-Boc-piperidine) | — | C33H44N6O3 Calc.: 572 Found: 573 |

-continued
| entry | $R_{11}$ | acylation reagent | isomer | MF FAB-MS(M + 1) |
|---|---|---|---|---|
| 3 | (structure) | (structure) | S D | C33H40N6O3S Calc.: 600 Found: 601 |
EXAMPLE 42
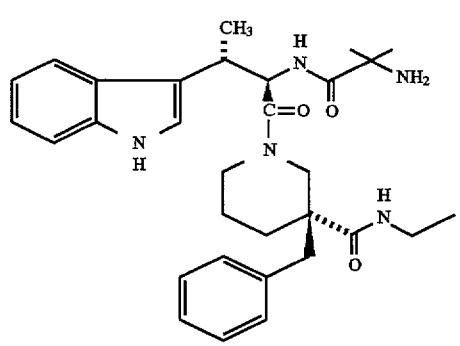
-continued
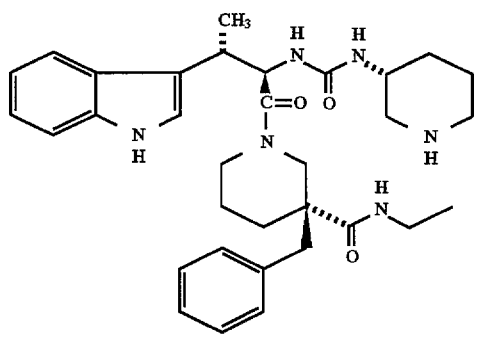
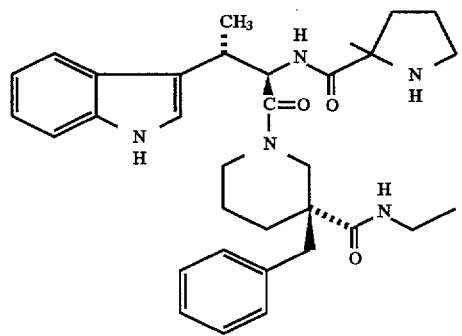
Similarly, the following compounds were prepared essentially according to the procedure described above, but using Boc-(2R,3S)-β-Me-TrpOH which were subsequently deprotected as described above.

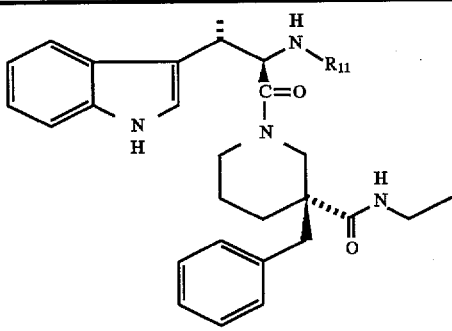

| entry | R$_{11}$ | acylation reagent | isomer | MF<br>FAB-MS(M + 1) |
|---|---|---|---|---|
| 1 | (structure with NH$_2$) | Boc—AibOH | — | C31H41N5O3<br>Calc.: 531<br>Found: 532 |
| 2 | (structure with pyrrolidine NH) | Boc—α-Me—Pro—OH | d1<br>d2 | C33H43N5O3<br>Calc.: 557<br>Found: 558 |
| 3 | (structure with piperidine NH) | (isocyanate with N-Boc piperidine) | — | C33H44N6O3<br>Calc.: 572<br>Found: 573 |

EXAMPLE 43

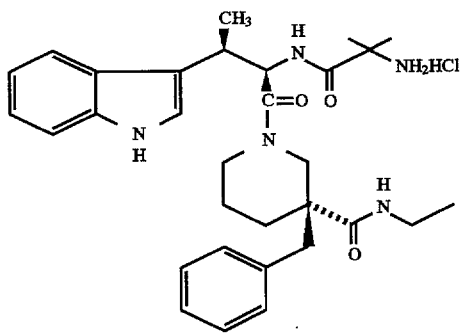

The title compound was prepared according to the same procedure as described Example 40, but using Boc-(2S,3R)-β-Me-TrpOH which were subsequently deprotected as described above. FAB-MS calc. for C$_{31}$H$_{41}$N$_5$O$_3$: 531; Found 532 (M+H)

EXAMPLE 44

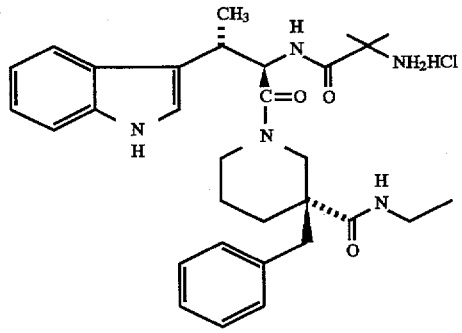

The title compound was prepared according to the same procedure as described Example 40, but using Boc-(2S,3S)-β-Me-TrpOH which were subsequently deprotected as described above. FAB-MS calc. for C$_{31}$H$_{41}$N$_5$O$_3$: 531; Found 532 (M+H)

EXAMPLE 45

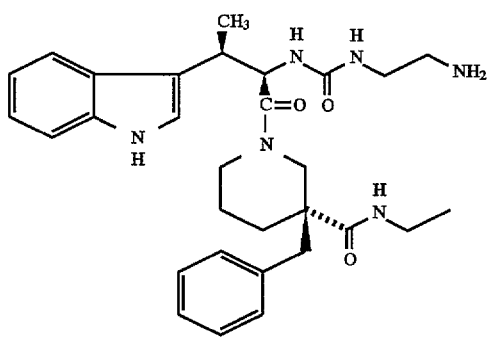

Step A:

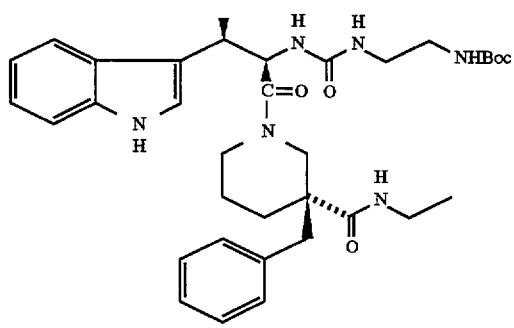

To a solution of the intermediate prepared in Step B of Example 40 (50 mg, 0.103 mmol) and N,N-diisopropylethylamine (54 μL, 0.315 mmol) in dichloromethane (10 mL) was added N,N'-disuccinin-imidyl carbonate (27 mg, 0.103 mmol) at room temperature. The reaction mixture was stirred for one hour, and then N-t-butyloxycarbonyl ethylenediamine (17 mg, 0.103 mmol) was added and the resulting mixture was stirred overnight. The solution was washed with saturated sodium chloride, dried over anhydrous magnesium sulfate; then filtered and concentrated. Purification by MPLC eluting with 5% methanol in ethyl acetate gave the desired Boc intermediate (31 mg).

FAB-MS calc. for $C_{35}H_{48}N_6O_5$: 632; Found 633 (M+H)

Step B:

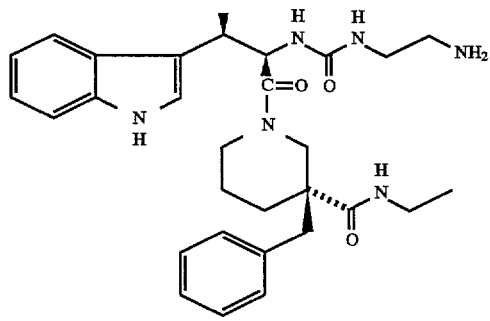

To a solution of the intermediate from the previous step (31 mg) in dichloromethane (2 mL) was added TFA (2 mL). The reaction mixture was stirred room temperature for 1 hour and was evaporated to give the salts as white foam. FAB-MS calc. for $C_{30}H_{40}N_6O_3$: 532 Found 533 (M+H)

EXAMPLE 46

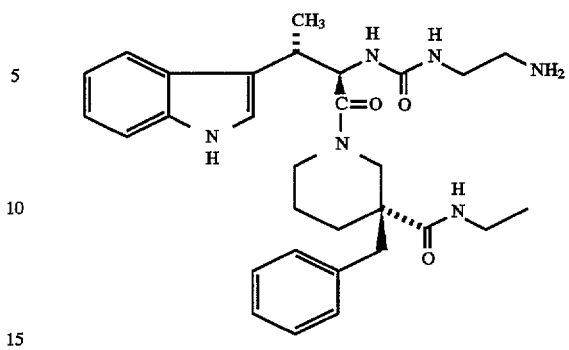

The title compound was prepared essentially according to the same procedure as described Example 45, but using intermediates derived from Boc-(2R,3S)-β-Me-TrpOH which were subsequently deprotected as described above. FAB-MS calc. for $C_{30}H_{40}N_6O_3$: 532; Found 533 (M+H).

The compounds shown in the following table were prepared according to Example 45, but using intermediates from Example 2, Step C and the requisite mono Boc protected diamines which were subsequently deprotected or converted to salt form as described above.

| entry | $R_{12}$ | MF FAB-MS(M + 1) |
|---|---|---|
| 1 | —NH(CH$_2$)$_2$NH$_2$ | $C_{29}H_{37}N_5O_4$ 520 |
| 2 | —NH(CH$_2$)$_3$NH$_2$ | $C_{30}H_{39}N_5O_4$ 534 |
| 3 | —NH(CH$_2$)$_4$NH$_2$ | $C_{31}H_{41}N_5O_4$ 548 |
| 4 | —NH(CH$_2$)$_5$NH$_2$ | $C_{32}H_{43}N_5O_4$ 562 |
| 5 | —NH(CH$_2$)$_6$NH$_2$ | $C_{33}H_{45}N_5O_4$ 576 |
| 6 | —NH(CH$_2$)$_7$NH$_2$ | $C_{34}H_{47}N_5O_4$ 590 |
| 7* | —NH(CH$_2$)$_2$N(CH$_3$)$_2$ | $C_{31}H_{41}N_5O_4$ 548 |
| 8 | piperazine-NH | $C_{31}H_{39}N_5O_4$ 546 |
| 9* | N-methylpiperazine-NCH$_3$ | $C_{32}H_{41}N_5O_4$ 560 |

-continued

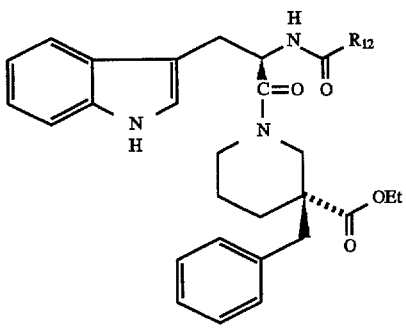

| entry | R₁₂ | MF FAB-MS(M + 1) |
|---|---|---|
| 10ᵃ | (6-methylamino-2-aminopyridine) | $C_{32}H_{36}N_6O_4$ 569 |
| 11ᵇ | (N-methyl-3-aminopiperidine) | $C_{32}H_{41}N_5O_4$ 560 |
| 12ᵇ | (N-methyl-3-aminopiperidine, other stereo) | $C_{32}H_{41}N_5O_4$ 560 |
| 13ᵃ | (N-methyl-quinuclidinyl) | $C_{34}H_{43}N_5O_4$ 586 |
| 14ᶜ | (3-quinuclidinyloxy) | $C_{34}H_{42}N_4O_5$ 585 |
| 15ᵇ | (N-methyl-3-methyl-3-aminopiperidine) | $C_{33}H_{43}N_5O_4$ 574 |
| 16ᵇ | (N-methyl-4-methyl-4-aminopiperidine) | $C_{33}H_{43}N_5O_4$ 574 |

ᵃThe compounds were prepared from the diamine directly without protection, in which case excess diamine was used and the product was purified after the reaction and converted to HCl salt by reaction with 1 equivalent of concentrated hydrochloric acid.
ᵇThe compounds were prepared from the corresponding isocyanate and the product from Step C of Example 2 as similarly described in Example 37 steps A and B, followed by Boc removal.
ᶜprepared from 3-quinuclidinyl chloroformate and the intermediate from Step C of Example 2.

EXAMPLE 47

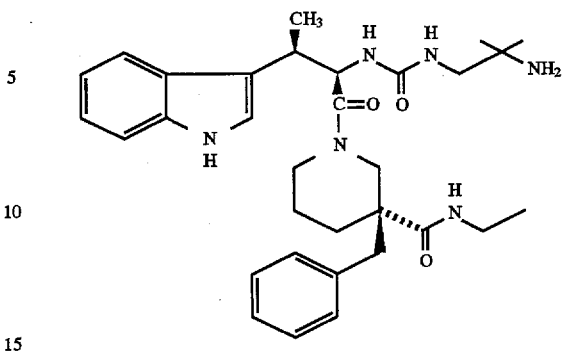

Step A:

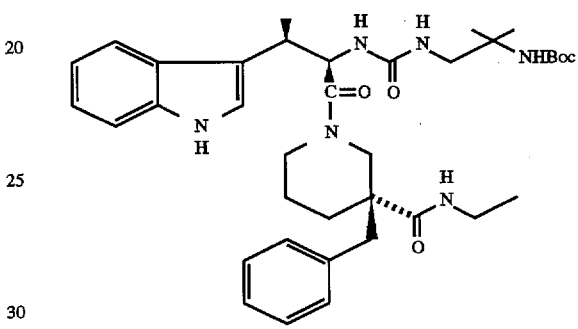

To a solution of the intermediate prepared in Step B of Example 40 (50 mg, 0.103 mmol) and N,N-diisopropylethylamine (54 μL, 0.315 mmol) in dichloromethane (10 mL) was added 2-methyl-2-(t-butyloxycarbonylamino)ethyl isocyanate (prepared by refluxing N-Boc-βB-dimethyl-β-alanine, and DPPA; see Example 36 Step B; 1.1 equivalents), and the resulting mixture was stirred overnight and then heated at 60° C. for two hours. The solution was washed with saturated sodium chloride and 3N HCl, dried over anhydrous magnesium sulfate; then filtered and concentrated. Purification by MPLC eluting with 5% methanol in ethyl acetate gave the desired Boc intermediate (38 mg).

FAB-MS calc. for $C_{37}H_{52}N_6O_5$: 660; Found 661 (M+H)

Step B:

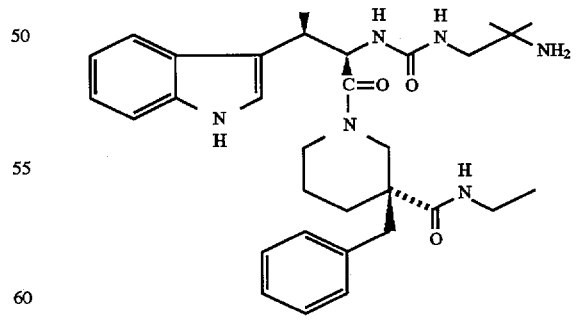

To a solution of the intermediate from the previous step (38 mg) in dichloromethane (2 mL) was added TFA (2 mL). The reaction mixture was stirred room temperature for 1 hour and was evaporated to give the salts as white foam.

FAB-MS calc. for $C_{32}H_{44}N_6O_5$: 560; Found 561 (M+H)

EXAMPLE 48

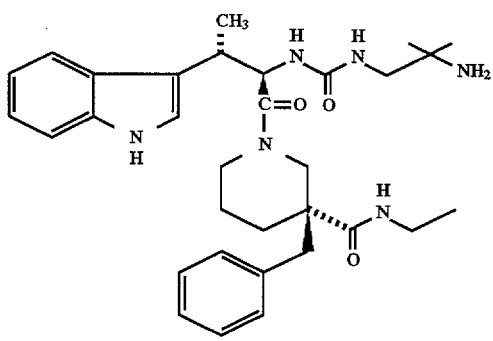

The title compound was prepared essentially according to the same procedure as described Example 45, but using intermediates prepared from Boc-(2R,3S)-β-Me-TrpOH which were subsequently deprotected as described above. FAB-MS calc. for $C_{32}H_{44}N_6O_5$: 560; Found 561 (M+H)

EXAMPLE 49

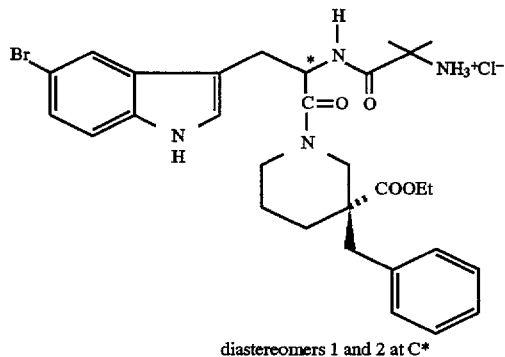

diastereomers 1 and 2 at C*

Step A:

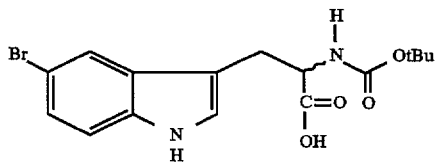

5-Bromo-(DL)-tryptophan (1 g) that was purchased from commercial sources was dissolved in aqueous 1N NaOH and a solution of 0.92 g of di-t-butylcarbonate in 1 mL of dioxane was added and stirred for 2 days. The white precipitate that formed was collected by filtration and acidified with 1N HCl solution till pH=4 and extracted with ethyl acetate. The combined organics were washed with brine, dried over MgSO4 and concentrated to 1.3 g of N-t-BOC-5-bromo-(DL)-tryptophan as a white solid.

Step B:

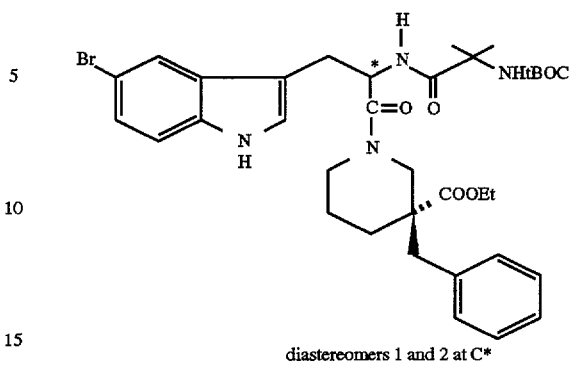

diastereomers 1 and 2 at C*

To a solution of 0.50 g of the compound from Step A in dichloromethane was added 0.445 g of the piperidine hydrochloride (prepared as described in Example 2, Step B), 0.17mL of N-methylmorpholine, 0.254 g of HOBT and 0.36 g of EDC and stirred at room temperature for 16 h. The reaction mixture washed with 1H HCl, saturated aqueous NaHCO3, brine and dried over MgSO4 and concentrated to 1.05 g of the coupled product. A solution of 0.20 g of the above N-Boc compound in ethyl acetate was treated with HCl(gas) for 1 min. and then stirred at rt for 30 min. Ether was added and the precipitate was collected by filtration and used without purification. To a solution of the amine hydrochloride salt in dichloromethane was added 0.07 mL of N-methylmorpholine, 0.065 g of N-BOC-amino isobutyric acid, 0.052 g of HOBT and 0.075 g of EDC and stirred at rt overnight. The reaction was worked-up as described above to give a thick oily residue. Analytical TLC analysis of this material with 50% ethyl acetate-hexane indicated two compounds with $R_f$ of 0.28 and 0.36 respectively. These compounds were separated by radial PLC (chromatotron) with hexane-ethyl acetate (1:3 to 2:1) as the eluent to give 66 mg of the less polar compound (diastereomer 1) and 29 mg of the more polar compound (diastereomer 2).

Step C:

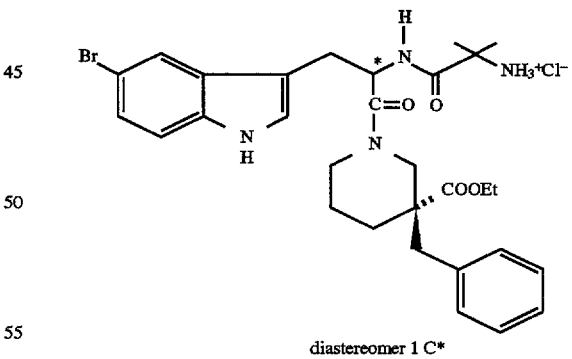

diastereomer 1 C*

Aproximately 60 mg of diastereomer 1 (prepared as described in Step B) was treated with HCl(gas) in ethyl acetate and the precipitate was collected after filtration to give the title compound as a pinkish solid. Key $^1$H NMR resonances (400 MHz; CD$_3$OD; mixture of rotamers) 7.80 and 7.70 (2d, 1H), 7.35–7.00 (m, 7H), 6.80 (d, 1H), 5.35–5.10 (m, 1H), 4.40 (bd, 1H), 4.10–3.95 (2q, 2H), 3.80 (d, 1H), 3.30–300 (m, 3H), 2.83 and 2.52 (2q, 2H), 1.58 (s, 3H)and 1.53 (s, 3H), 1.18 and 1.11 (2t, 3H). FABMS m/e calcd. for $C_{30}H_{36}N_4O_4Br$ 596; found 597.2 (m+1).

Step D:

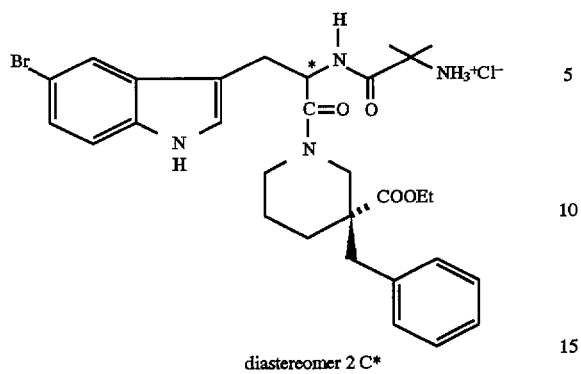

diastereomer 2 C*

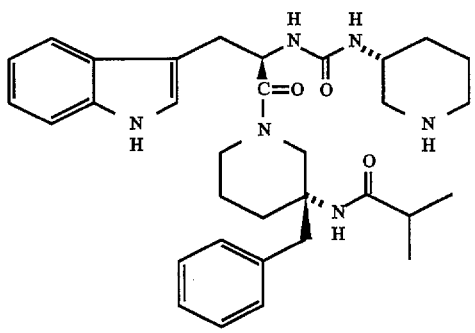

Aproximately 25 mg of diastereomer 2 (prepared as described in Step B) was treated with HCl(gas) in ethyl acetate and the precipitate was collected after filtration to give the title compound as a pinkish solid. Key $^1$H NMR resonances (400 MHz; $CD_3OD$; mixture of rotamers) 7.92 and 7.72(2d, 1H), 7.35–6.95 (m, 8H), 5.40–5.20 (m, 1H), 4.45–3.85 (m, 4H), 3.45–3.00 (m, 4H), 3.00–2.80 (m, 2H), 2.53 (ABq, 2H), 1.58, 1.55, 1.50 and 1.36 (4s, 6H), 1.20–1.00 (2t, 3H). FABMS m/e calcd. for $C_{30}H_{36}N_4O_4Br$ 596; found 597.2 (m+1).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound which is selected from the group consisting of:

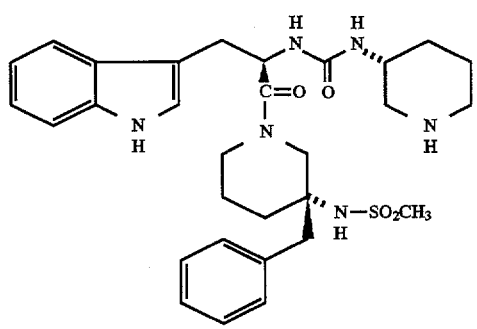

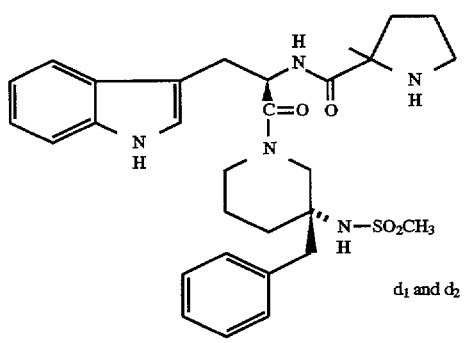

d₁ and d₂

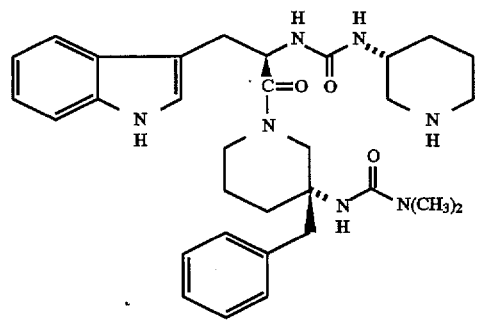

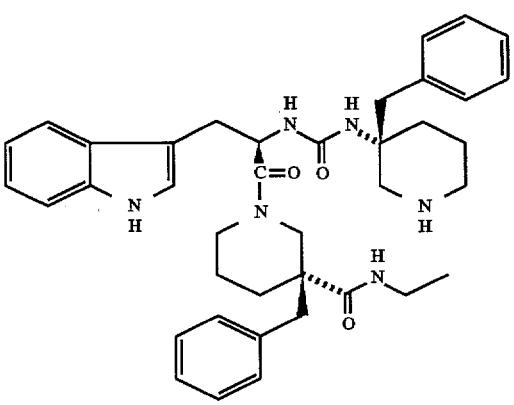

155
-continued
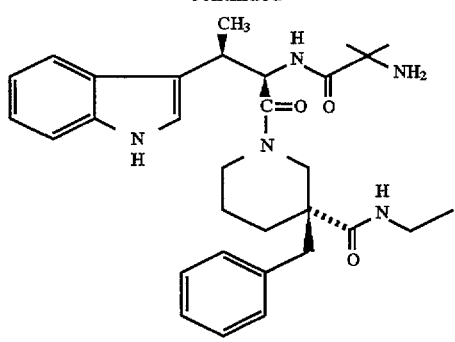
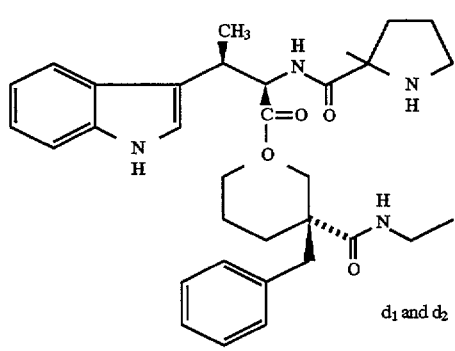
d₁ and d₂
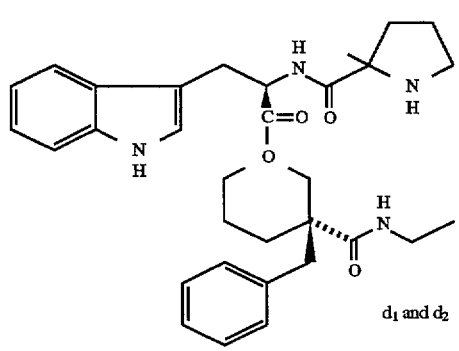
d₁ and d₂
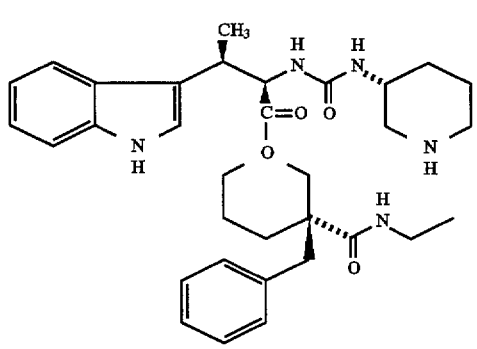
156
-continued
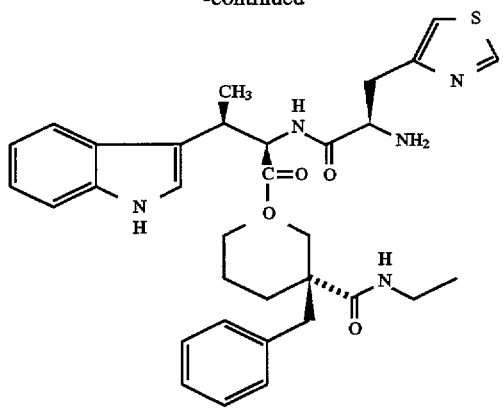
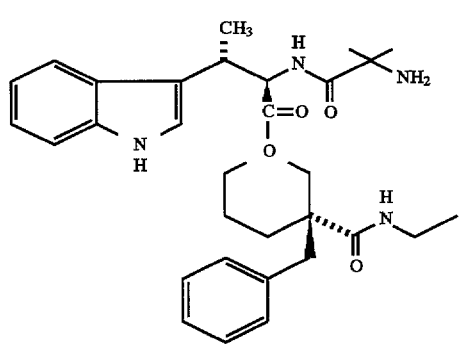
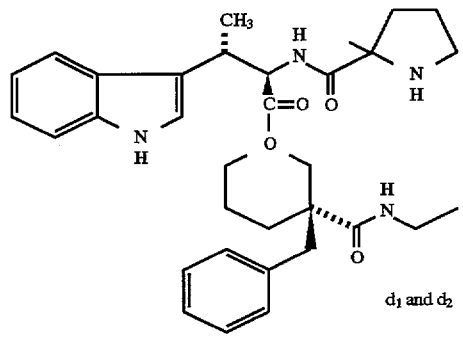
d₁ and d₂
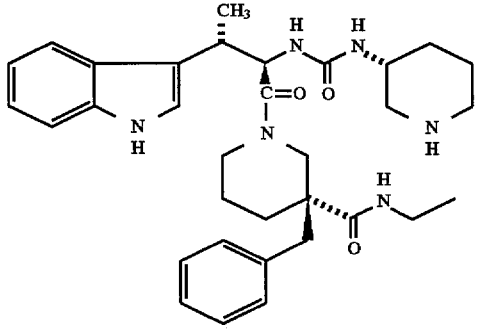

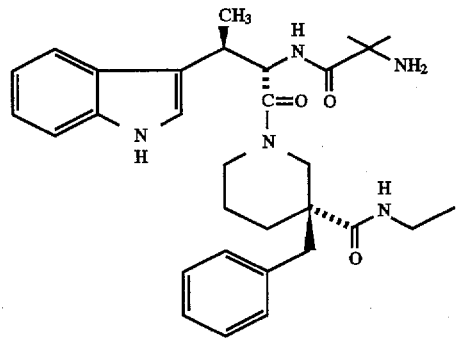
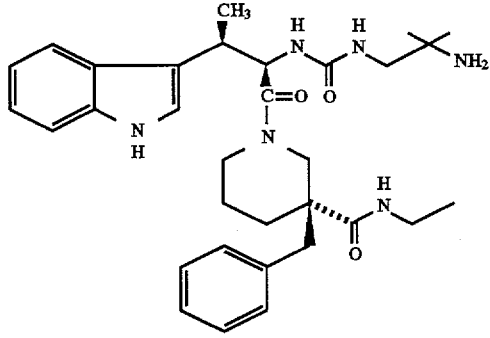
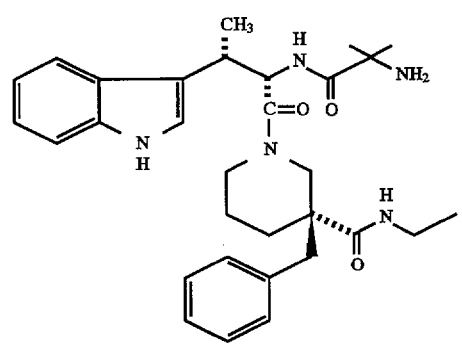
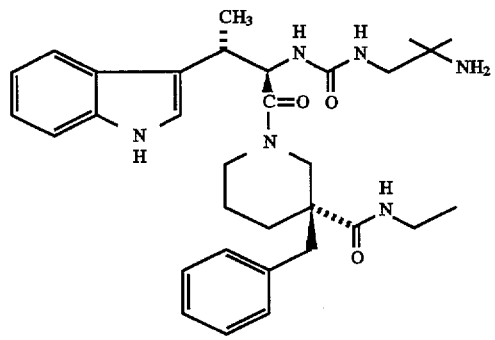
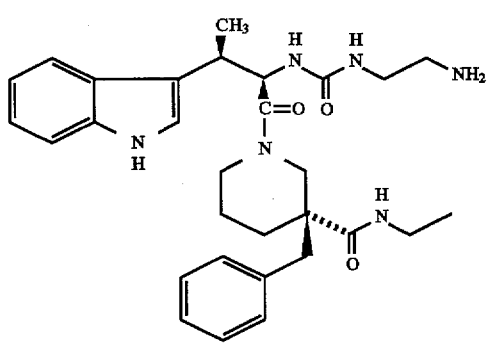
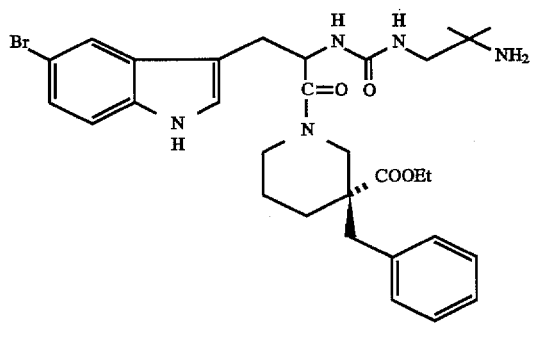
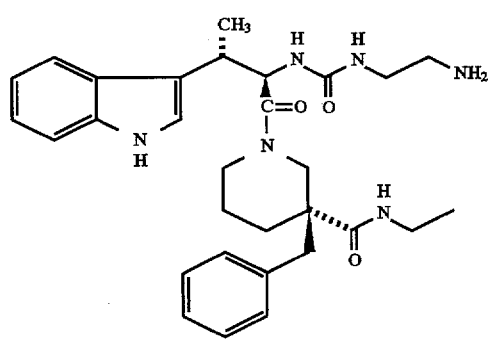
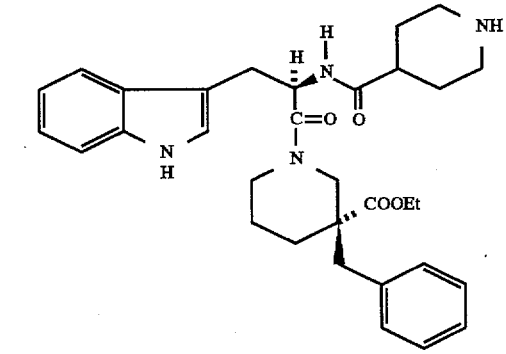

159
-continued

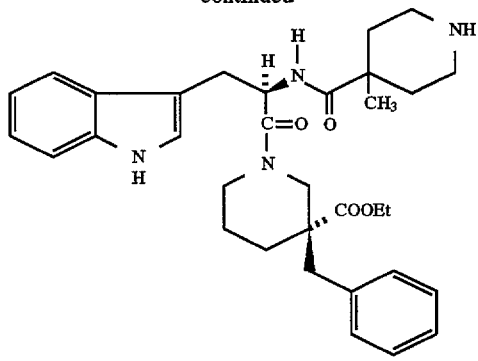

160
-continued

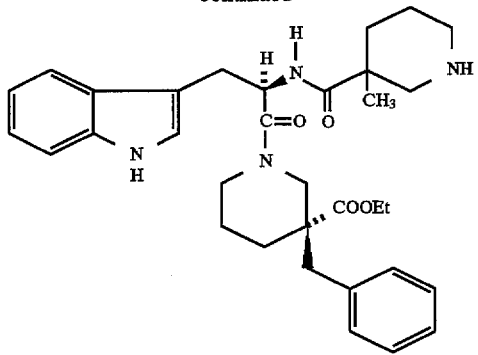

and pharmaceutically acceptable salts and individual diastereomers thereof where not otherwise specified.

2. A pharmaceutical composition which comprises a pharmaceutically acceptable carrier and a compound of claim 1.

3. A method for increasing levels of endogenous growth hormone in a human or an animal which comprises administering to such human or animal an effective amount of a compound of claim 1.

* * * * *